United States Patent
Dewal

(10) Patent No.: US 12,228,481 B2
(45) Date of Patent: Feb. 18, 2025

(54) EXPANSION MICROSCOPY COMPATIBLE ANCHORABLE HANDE STAINING FOR HISTOPATHOLOGY

(71) Applicant: EXPANSION TECHNOLOGIES, Boston, MA (US)

(72) Inventor: Mahender Babu Dewal, Arlington, MA (US)

(73) Assignee: EXPANSION TECHNOLOGIES, Cambridge, MA (US)

( * ) Notice: Subject to any disclaimer, the term of this patent is extended or adjusted under 35 U.S.C. 154(b) by 571 days.

(21) Appl. No.: 17/419,545

(22) PCT Filed: Dec. 31, 2019

(86) PCT No.: PCT/US2019/069065
§ 371 (c)(1),
(2) Date: Jun. 29, 2021

(87) PCT Pub. No.: WO2020/142490
PCT Pub. Date: Jul. 9, 2020

(65) Prior Publication Data
US 2022/0074827 A1    Mar. 10, 2022

Related U.S. Application Data

(60) Provisional application No. 62/786,994, filed on Dec. 31, 2018.

(51) Int. Cl.
*G01N 1/30*   (2006.01)
*C09B 11/08*  (2006.01)
(Continued)

(52) U.S. Cl.
CPC ............... *G01N 1/30* (2013.01); *C09B 11/08* (2013.01); *C09B 61/00* (2013.01); *G01N 33/582* (2013.01);
(Continued)

(58) Field of Classification Search
CPC ........ G02B 21/06; G02B 21/36; G02B 21/00; G02B 21/0004; G02B 21/0076;
(Continued)

(56) References Cited

U.S. PATENT DOCUMENTS

| 4,213,904 A | 7/1980 | Haugland |
| 10,059,999 B2 | 8/2018 | Jia et al. |

(Continued)

FOREIGN PATENT DOCUMENTS

| WO | WO2015127183 | 8/2015 |
| WO | WO2017027367 | 2/2017 |

(Continued)

OTHER PUBLICATIONS

International Search Report and Written Opinion, mailed Mar. 19, 2020, from corresponding International Application No. PCT/US19/69065.

(Continued)

*Primary Examiner* — Arnel C Lavarias
(74) *Attorney, Agent, or Firm* — Mark S. Cohen; PEARL COHEN ZEDEK LATZER BARATZ LLP

(57) ABSTRACT

A technique for expansion microscopy (ExM) utilizing anchorable derivatives of hematoxylin and eosin (H&E) stained tissue specimens within tissue samples, in order to achieve high resolution detection of biomolecules with precise morphological features of cells and nuclei, which in turn, allows for effective for accurate early stage disease diagnosis including various cancers. Staining with H&E employs anchorable derivatives that can be cross-linked into the ExM hydrogel matrix.

21 Claims, 2 Drawing Sheets

(51) Int. Cl.
*C09B 61/00* (2006.01)
*G01N 33/58* (2006.01)
*G02B 21/06* (2006.01)
*G02B 21/36* (2006.01)

(52) U.S. Cl.
CPC ........ *G01N 2001/302* (2013.01); *G02B 21/06* (2013.01); *G02B 21/36* (2013.01)

(58) Field of Classification Search
CPC .. G01N 1/30; G01N 33/582; G01N 2001/302; G01N 33/58; G01N 21/6456; G01N 21/6458; G01N 21/6486; C09B 11/08; C09B 61/00; C09B 11/00; C09B 11/02; C09B 11/04; C09B 11/06
USPC .......................... 359/385, 362, 363, 368, 369
See application file for complete search history.

(56) References Cited

U.S. PATENT DOCUMENTS

| | | | |
|---|---|---|---|
| 2001/0046668 A1* | 11/2001 | Levine | C07K 14/005 435/7.1 |
| 2015/0004712 A1 | 1/2015 | Keillor et al. | |
| 2016/0116384 A1 | 4/2016 | Chen et al. | |
| 2016/0305856 A1 | 10/2016 | Boyden et al. | |
| 2017/0089811 A1 | 3/2017 | Tillberg et al. | |
| 2017/0253918 A1 | 9/2017 | Kohman | |
| 2018/0052081 A1 | 2/2018 | Kohman | |
| 2018/0119219 A1 | 5/2018 | Chen et al. | |
| 2020/0316226 A1* | 10/2020 | Marban | A61K 47/60 |

FOREIGN PATENT DOCUMENTS

| | | |
|---|---|---|
| WO | WO2017027368 | 2/2017 |
| WO | WO2017147435 | 8/2017 |
| WO | WO2018136856 | 7/2018 |
| WO | WO2018157048 | 8/2018 |
| WO | WO2018157074 | 8/2018 |
| WO | WO2019055242 | 3/2019 |
| WO | WO2019075091 | 4/2019 |
| WO | WO2019103996 | 5/2019 |

OTHER PUBLICATIONS

Pubchem, CID 11048, Eosin, Aug. 1, 2005, pp. 1-33; retrieved from Internet: https://pubchem.ncbi.nlm.nih.gov/compound/11048.

Pubchem, CID 442514, Hematoxyline, Jun. 24, 2005, pp. 1-30; retrieved from Internet: https://pubchem.ncbi.nlm.nih.gov/compound/442514.

Chen et al., "Expansion microscopy", Science, Jan. 30, 2015, 347(6221):543-548.

Tillberg et al., "Protein-retention expansion microscopy of cells and tissues labeled using standard fluorescent proteins and antibodies", Nature Biotechnology, Jul. 4, 2016, 34(9):987-996; doi:10.1038/nbt.3625.

Chen et al., "Nanoscale imaging of RNA with expansion microscopy", Nature Methods, Jul. 4, 2016, 13:679-684; https://doi.org/10.1038/nmeth.3899.

* cited by examiner

EXPANSION MICROSCOPY COMPATIBLE ANCHORABLE HANDE STAINING FOR HISTOPATHOLOGY

CROSS-REFERENCE TO RELATED APPLICATIONS

This application claims the benefit of U.S. Provisional Application No. 62/786,994, filed Dec. 31, 2018, the contents of which are incorporated herein by reference in its entirety.

BACKGROUND

Histopathology is the gold standard for clinical evaluation of many diseases including various cancers. In histopathology, chemically fixed surgical biopsy/autopsy tissue sections either embedded in paraffin or frozen will be stained with molecularly-specific absorptive dyes and then visualized using in a bright-field light microscope. The most commonly used dyes in this method are hematoxylin and eosin (H&E) that work well with a variety of fixatives and displays a broad range of cytoplasmic, extracellular matrix features in pink and cell nuclei in purple. Multiple specialized pathologists analyze abundance and morphological features of cells and nuclei of these specimens for disease diagnosis including various cancers. However, a number of recent studies indicated that this method often leads to only 50% agreement between pathologists for accurate cancer diagnosis. Because information visualized from these specimens is limited by the diffraction limit of the light microscope, this leads to misinterpretation, false positives and false negatives. The lack of improved resolution of these methods in pathology may necessitate a second surgery or biopsy procedure in the event that the resection or sampling proves insufficient. Repeat procedures pose additional risk to patients, may delay adjuvant therapy, reduce cosmetic outcomes, and impose an additional financial burden on the healthcare system.

Electron microscopy (EM) has become an essential tool in histopathology to analyze the pathogenesis of diseases. Though EM overcomes the resolution issues and provides accurate diagnosis pathology, facilities for EM are scarce in community hospitals because they are expensive to establish and maintain and sample submission, processing, and analysis is time-consuming (several weeks to months). Thus, EM analysis represents a major bottleneck and often delays disease diagnoses and timely intervention. Alternatively, other super-resolution microscopy techniques such as structured illumination microscopy (SIM), stochastic optical reconstruction microscopy (STORM), stimulated emission depletion microscopy (STED), and photoactivated localization microscopy (PALM) may address the resolution issues. However, these techniques also encounter the same issues that EM has. Moreover, they are not suitable to scan H&E stained specimens but only compatible with specialized fluorescence dyes and immunofluorescence methods which are uncommon in most of the hospital settings and pathological centers.

Expansion microscopy (ExM) a novel, super-resolution technique that physically expands the sample 100 to 1000 fold while maintaining the relative spatial integrity of the components of the specimen, allowing nano-scale resolution of subcellular structures using light microscopic methods. The ExM method involves synthesizing a swellable polymer network within a specimen, then physically expanding it. By covalently anchoring specific labels located within the specimen directly to the polymer network, labels located closer than the optical diffraction limit can be isotropically expanded and resolved.

It is towards the improvement of the ExM method by incorporating light microscopy labels that the invention is directed.

BRIEF DESCRIPTION OF THE INVENTION

In one embodiment, a method is provided for the high resolution detection of biomolecules in a biological sample comprising the steps of:
  a. labeling biomolecules in the sample with hematoxylin, eosin, or the combination thereof;
  b. anchoring biomolecules in the sample using a cross-linker, wherein the cross-linker comprises an anchor capable of polymerization;
  c. permeating the sample with a swellable, polymerizable material and polymerizing the material, wherein the polymerizing results in covalent crosslinking of the anchor to the swellable material to form a sample-swellable material complex;
  d. digesting the sample-swellable material complex;
  e. enlarging the sample-swellable material complex by adding an aqueous solvent or liquid to cause the sample to swell, thereby physically expanding the sample-swellable material complex resulting in an enlarged biological sample; and
  f. detecting the biomolecules in the biological sample under high resolution using conventional diffraction limited light microscopy.

In one embodiment a protein cross-linker and a nucleic acid cross-linker are used for anchoring in step (b). In one embodiment, a protein cross-linker is used for anchoring in step (b) but a nucleic acid cross-linker is not used. In one embodiment the protein cross-linker is glutaraldehyde or AcX. In one embodiment the nucleic acid cross-linker is NucliX. In one embodiment, when both cross-linkers are used, they may be used simultaneously or successively. In one embodiment, the sample is isotropically expanded.

In another embodiment, a method is provided for the high resolution detection of biomolecules in a biological sample comprising the steps of:
  a. labeling biomolecules in the sample with an anchorable hematoxylin, an anchorable eosin, or the combination thereof, wherein the anchorable hematoxylin, anchorable eosin, or combination thereof comprise an anchor moiety capable of polymerization;
  b. permeating the sample with a swellable, polymerizable material and polymerizing the material, wherein the polymerizing of the sample results in covalent cross-linking of the anchor of the anchorable hematoxylin or anchorable eosin to the polymerizable material to form a sample-swellable material complex;
  c. digesting the sample-swellable material complex;
  d. enlarging the sample-swellable material complex by adding an aqueous solvent or liquid to cause the sample to swell, thereby physically expanding the sample-swellable material complex resulting in an enlarged biological sample; and
  e. detecting the biomolecules in the sample under high resolution using conventional diffraction limited light microscopy.

In one embodiment of any of the foregoing methods, the labeling step using hematoxylin and eosin, or labeling step using anchorable hematoxylin and anchorable eosin, are performed simultaneously or successively. In one embodiment, hematoxylin and an anchorable eosin are used; in one embodiment, an anchorable hematoxylin and eosin are used. In one embodiment, the sample is isotropically expanded.

In one embodiment, a protein cross-linker or a nucleic acid cross-linker may be used for anchoring in step (b) if an anchorable eosin or anchorable hematoxylin is not used, respectively. In one embodiment, if only an anchorable hematoxylin is used (which binds to nucleic acids), then a protein cross-linking agent such as but not limited to AcX is also used, such that nucleic acids in the specimen are stained and cross-linked into the hydrogel via the anchorable hematoxylin, and proteins in the sample are cross-linked into the hydrogel matrix via AcX. In one embodiment the proteins may be stained with a non-anchorable dye. In one embodiment, if only an anchorable eosin is used (which binds to proteins), then a nucleic acid cross-linking agent such as but not limited to NucliX is also used, such that proteins in the specimen are stained and cross-linked into the hydrogel via the anchorable eosin, and nucleic acids in the sample are cross-linked into the hydrogel matrix via NucliX. In one embodiment, the nucleic acids may be stained with a non-anchorable dye. In another embodiment, non-anchorable dyes such as hematoxylin or eosin or their combination are also used in any of the foregoing embodiments.

In one embodiment, a protein cross-linker is used for anchoring in step (b) but a nucleic acid cross-linker is not used. In one embodiment the protein cross-linker is glutaraldehyde or AcX. In one embodiment the nucleic acid cross-linker is NucliX. In one embodiment, when both cross-linkers are used, they may be used simultaneously or successively.

In one embodiment, the protein cross-linking agent is used before or after the anchorable eosin is used. In one embodiment, the nucleic acid cross-linking agent is used before or after the anchorable hematoxylin is used. In one embodiment, the protein cross-linking agent is used before or after the anchorable hematoxylin, anchorable eosin, or both are used. In one embodiment, the nucleic acid cross-linking agent is used before or after the anchorable hematoxylin, anchorable eosin, or both are used. In one embodiment, the protein cross-linking agent and the nucleic cross-linking agent are used before, simultaneously, or after the anchorable or non-anchorable dyes are used in any combination and in any order. In another embodiment, the protein cross-linking agent, the nucleic acid cross-linking agent, the anchorable hematoxylin, the anchorable eosin, hematoxylin and eosin may be used in any combination and in any order.

In one embodiment, the sample is isotropically expanded.

In one embodiment of any of the foregoing methods, high resolution is nanoscale resolution. In one embodiment of either of the foregoing methods, the sample if attached to a substrate is detached before swelling. In one embodiment, the sample-swellable material complex is swelled isotropically when the aqueous solvent or liquid is added, thereby maintaining the relative spatial relationship of the labeled biomolecules.

In one embodiment of either of the foregoing methods, permeating the sample with a swellable, polymerizable material comprises permeating the sample with a composition comprising precursors of a swellable polymer and forming a swellable polymer in situ. In one embodiment of either of the foregoing methods, the polymerizable material comprises sodium acrylate, acrylamide and N,N-methylenebisacrylamide or dimethylacrylamide. In one embodiment of either of the foregoing methods, an initiator and accelerator or polymerization are added to the polymerizable material to initiate and accelerate polymerization thereof.

In one embodiment, the anchorable hematoxylin comprises a moiety capable of anchoring to the polymer. In one embodiment, the anchorable hematoxylin is a compound of formula (II)

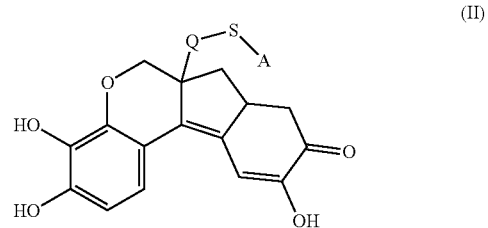

(II)

wherein Q is O or NH, S is a spacer or a bond, and A is an anchorable moiety capable of being polymerized into a hydrogel matrix.

In one embodiment, S is selected from

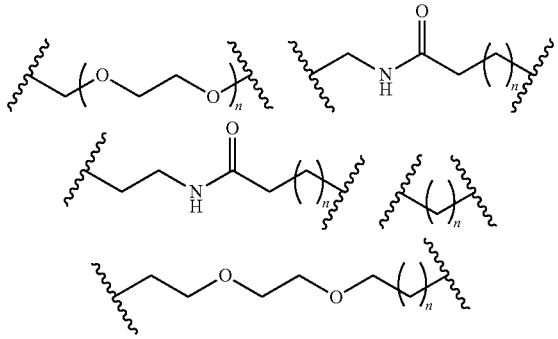

wherein n is an integer from 1 to 10.

In one embodiment, A is selected from a methacrylate, an acrylate, an acrylamide, a monoalkylacrylamide, a vinylalcohol, a vinylamine, an allylamine or an allylalcohol moiety.

In one embodiment, A is selected from:

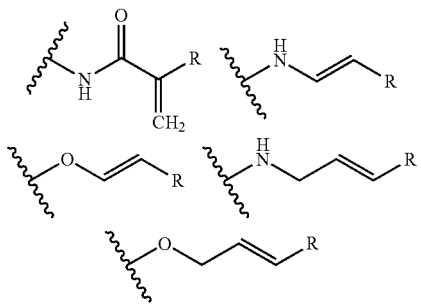

wherein R is H, alkyl, acyl, or nitrile.

In one embodiment, the alkyl is a $C_{1-6}$alkyl group, such as but not limited to methyl, ethyl, n-propyl, isopropyl, allyl, n-butyl, sec-butyl, isobutyl, tert-butyl, n-pentyl, sec-pentyl, isopentyl, tert-pentyl, n-hexyl or sec-hexyl. In one embodiment, the acyl is selected from methanoyl, ethanoyl, propanoyl, isopropanoyl, butanoyl, isobutanoyl, t-butanoyl, pentanoyl, isopentanoyl, neopentanoyl or benzoyl.

In one embodiment, the anchorable hematoxylin has the structure IIA, IIB, IIC, IID or IE:

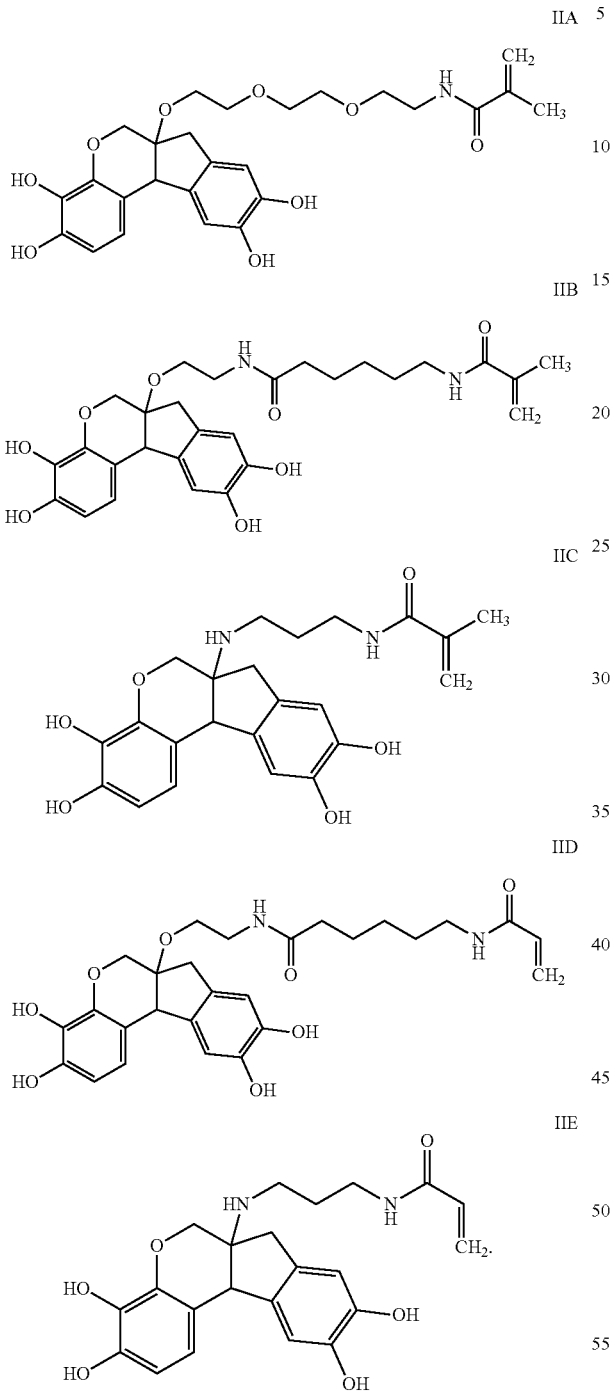

In one embodiment, the structure of any of the hematoxylin structures herein and the anchorable derivatives thereof comprise the oxidized form of hematoxylin, called hematein.

In one embodiment, the anchorable cosin comprises eosin with a moiety capable of anchoring to the polymer. In one embodiment the anchorable cosin is a compound of formula (III) or (IV)

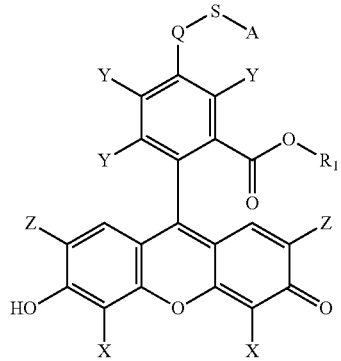

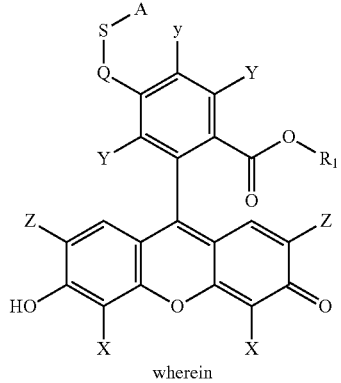

wherein

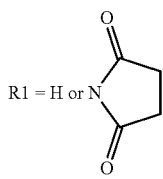

R1 = H or

| | |
|---|---|
| X = Z = Br, Y = H | Eosin Y |
| X = Br = NO₂, Y = H | Eosin B |
| X = Z = I, Y = H | Erythroosine B |
| X = Z = Br, Y = Cl | Phloxine B | and wherein Q is O or NH, S is a spacer or a bond, and A is an anchorable moiety capable of being polymerized into a hydrogel matrix.

In one embodiment, S is selected from

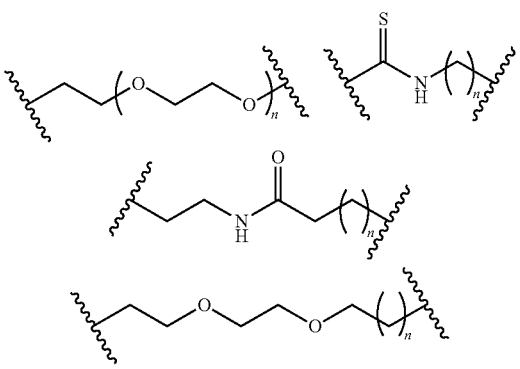

wherein n is an integer from 1 to 10.

In one embodiment, A is selected from a methacrylate, an acrylate, an acrylamide, a monoalkylacrylamide, a vinylalcohol, a vinylamine, an allylamine or an allylalcohol moiety.

In one embodiment, A is selected from:

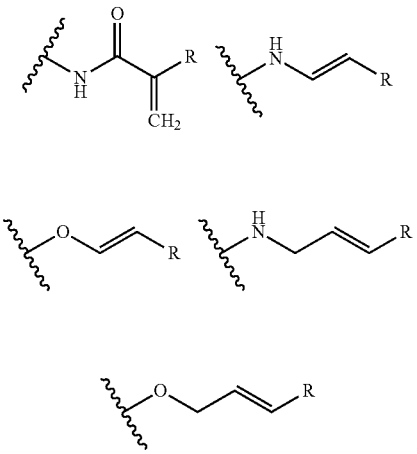

wherein R is H, alkyl, acyl, or nitrile.

In one embodiment, the alkyl is a $C_{1-6}$ alkyl group, such as but not limited to methyl, ethyl, n-propyl, isopropyl, allyl, n-butyl, sec-butyl, isobutyl, tert-butyl, n pentyl, sec-pentyl, isopentyl, tert-pentyl, n-hexyl or sec-hexyl. In one embodiment, the acyl is selected from methanoyl, ethanoyl, propanoyl, isopropanoyl, butanoyl, isobutanoyl, t-butanoyl, pentanoyl, isopentanoyl, neopentanoyl or benzoyl.

In one embodiment, the anchorable eosin has formula IIIA, IIIB, IIIC, IVA or IVB:

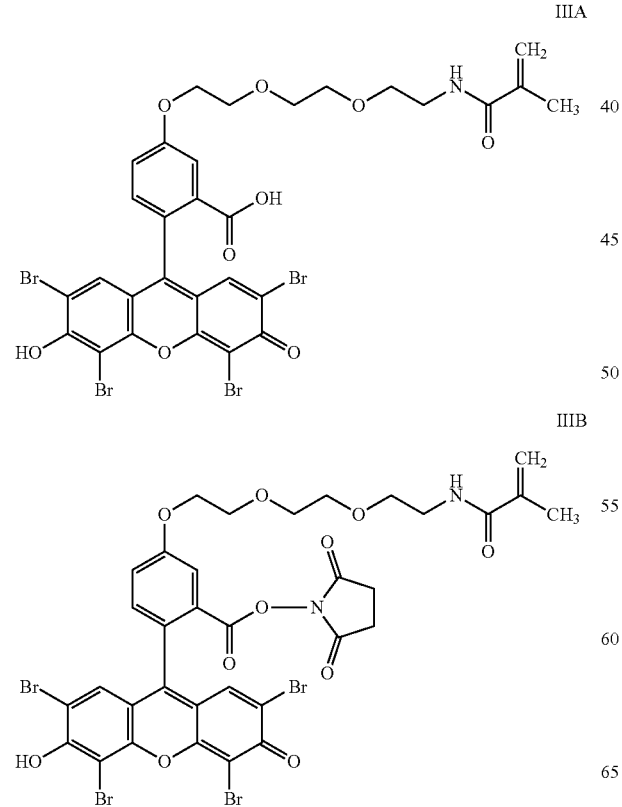

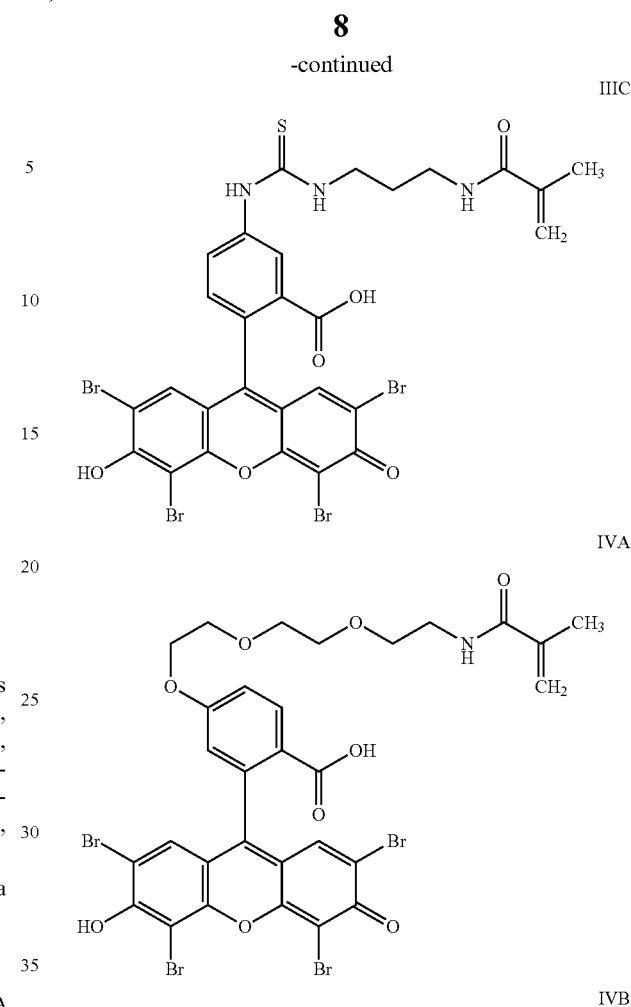

In any one of the foregoing embodiments, the biological sample is a fresh frozen sample. In any one of the foregoing embodiments, the biological sample is a formalin-fixed, paraffin embedded sample, and the sample is deparaffinized before step (a). In any of the foregoing embodiments, the sample is swelled isotropically by adding water or low ionic strength salt solution, resulting in an enlarged sample.

In another embodiment, a microscopy method is provided for producing a high-resolution image of a sample, the method comprising enlarging a sample of interest in accordance with any of the foregoing embodiments, and viewing the enlarged sample under a light microscope. In one embodiment, enlarging the sample of interest comprises embedding a sample of interest in a swellable material and swelling the material.

In another embodiment, a method is provided for optical imaging using light microscopy of a sample of interest with resolution better than the classical light microscopy diffraction limit based on physically expanding the sample itself, the method comprising the steps of the foregoing embodiments, and viewing the sample under a microscope.

In another embodiment, a method is provided for the high resolution detection of biomolecules in a biological sample comprising the steps of:

labeling biomolecules in the sample with an anchorable hematoxylin as depicted in formula (II), an anchorable eosin as depicted in formula (III) or/and (IV), or any combination thereof, in succession or simultaneously:

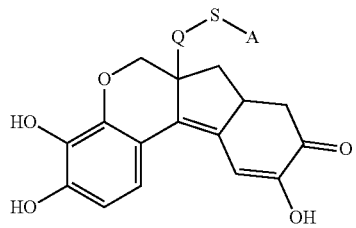

(II)

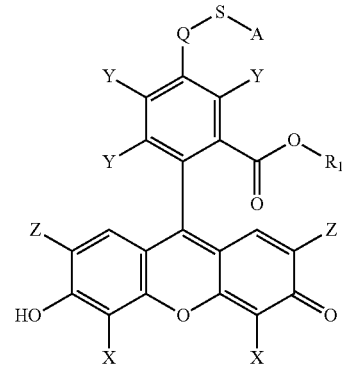

III

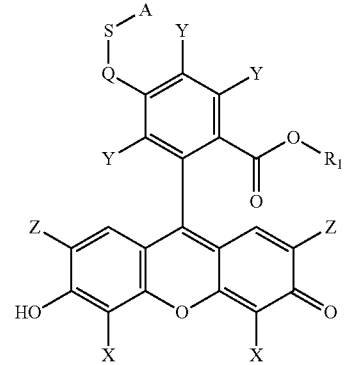

IV

X = Z = Br, Y = H       Eosin Y
X = Br = NO₂, Y = H    Eosin B
X = Z = I, Y = H         Erthyroosine B
X = Z = Br, Y = Cl       Phloxine B
wherein

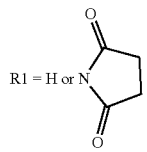

R1 = H or or any combination thereof,
wherein Q is O or NH, S is a spacer or a bond as described herein, and A is a moiety capable of being polymerized into a hydrogel matrix as described herein;

a. permeating the sample with a swellable, polymerizable material and polymerizing the material, wherein the polymerizing of the sample results in covalent cross-linking of the anchor of the anchorable hematoxylin or anchorable eosin to the polymerizable material to form a sample-swellable material complex;
b. digesting the sample-swellable material complex;
c. enlarging the sample-swellable material complex by adding an aqueous solvent or liquid to cause the sample to swell, thereby physically expanding the sample-swellable material complex resulting in an enlarged biological sample; and
d. detecting the biomolecules in the sample under high resolution using conventional diffraction limited light microscopy.

In one embodiment of any of the foregoing methods, the labeling step using hematoxylin and eosin, or labeling step using anchorable hematoxylin and anchorable eosin, are performed simultaneously or successively. In one embodiment, hematoxylin and an anchorable eosin are used; in one embodiment, an anchorable hematoxylin and eosin are used. In one embodiment, the sample is isotropically expanded.

In one embodiment, the protein cross-linking agent is used before or after the anchorable eosin is used. In one embodiment, the nucleic acid cross-linking agent is used before or after the anchorable hematoxylin is used. In one embodiment, the protein cross-linking agent is used before or after the anchorable hematoxylin, anchorable eosin, or both are used. In one embodiment, the nucleic acid cross-linking agent is used before or after the anchorable hematoxylin, anchorable eosin, or both are used. In one embodiment, the protein cross-linking agent and the nucleic cross-linking agent are used before, simultaneously, or after the anchorable or non-anchorable dyes are used in any combination and in any order In another embodiment, the protein cross-linking agent, the nucleic acid cross-linking agent, the anchorable hematoxylin, the anchorable eosin, hematoxylin and eosin may be used in any combination and in any order.

In one embodiment of any of the foregoing methods, high resolution is nanoscale resolution. In one embodiment of either of the foregoing methods, the sample if attached to a substrate is detached before swelling. In one embodiment, the sample-swellable material complex is swelled isotropically when the aqueous solvent or liquid is added, thereby maintaining the relative spatial relationship of the labeled biomolecules.

In one embodiment of either of the foregoing methods, permeating the sample with a swellable, polymerizable material comprises permeating the sample with a composition comprising precursors of a swellable polymer and forming a swellable polymer in situ. In one embodiment of either of the foregoing methods, the polymerizable material comprises sodium acrylate, acrylamide and N,N-methylenebisacrylamide or dimethylacrylamide. In one embodiment of either of the foregoing methods, an initiator and accelerator or polymerization are added to the polymerizable material to initiate and accelerate polymerization thereof.

In the foregoing embodiment, the anchorable hematoxylin comprises a moiety capable of anchoring to the polymer. In one embodiment, the anchorable hematoxylin is a compound of formula (II)

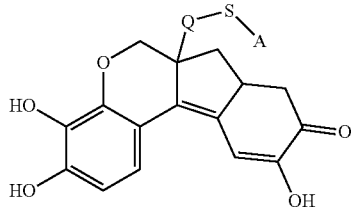

(II)

wherein Q is O or NH, S is a spacer or a bond, and A is an anchorable moiety capable of being polymerized into a hydrogel matrix.

In one embodiment, S is selected from

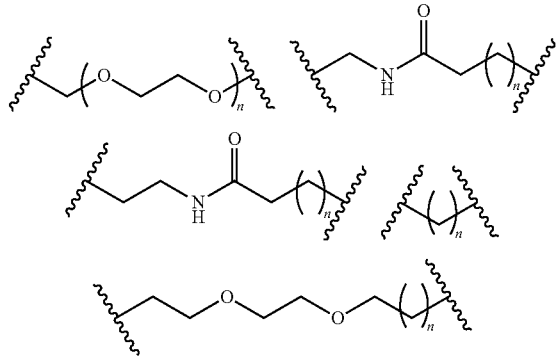

wherein n is an integer from 1 to 10.

In one embodiment, A is selected from a methacrylate, an acrylate, an acrylamide, a monoalkylacrylamide, a vinylalcohol, a vinylamine, an allylamine or an allylalcohol moiety.

In one embodiment, A is selected from:

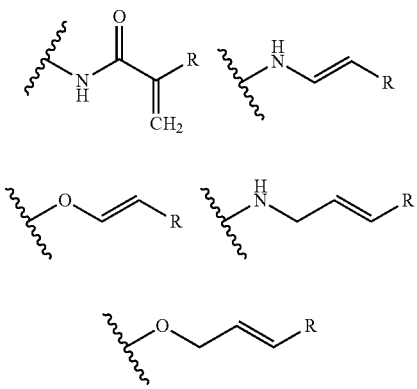

wherein R is H, alkyl, acyl, or nitrile.

In one embodiment, the alkyl is a $C_{1-6}$alkyl group, such as but not limited to methyl, ethyl, n-propyl, isopropyl, allyl, n-butyl, sec-butyl, isobutyl, tert-butyl, n pentyl, sec-pentyl, isopentyl, tert-pentyl, n-hexyl or sec-hexyl. In one embodiment, the acyl is selected from methanoyl, ethanoyl, propanoyl, isopropanoyl, butanoyl, isobutanoyl, t-butanoyl, pentanoyl, isopentanoyl, neopentanoyl or benzoyl.

In one embodiment, the anchorable hematoxylin has the structure IIA, IIB, IIC, IID or IIE:

IIA

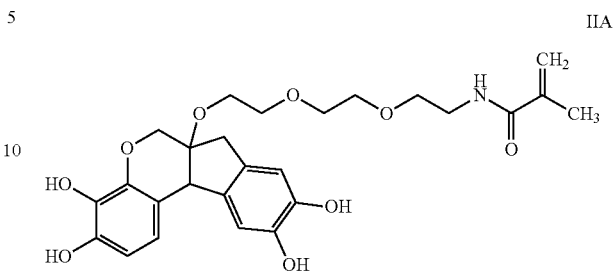

IIB

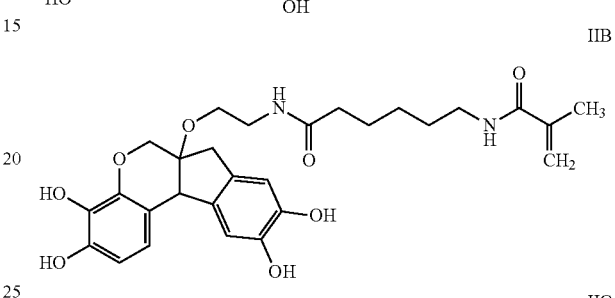

IIC

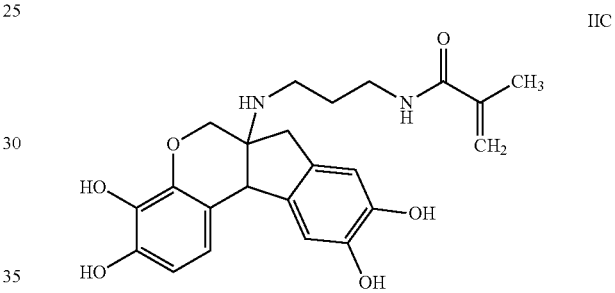

IID

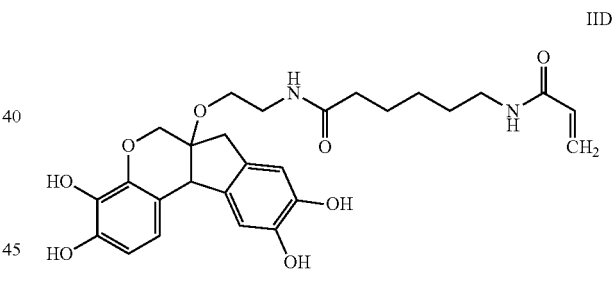

IIE

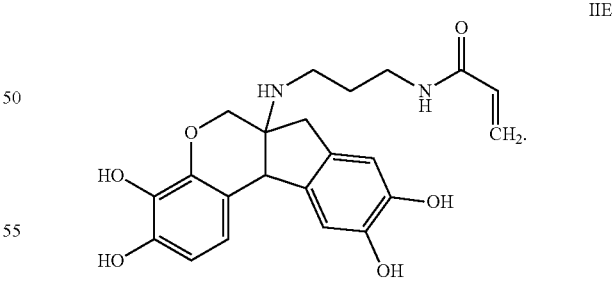

In one embodiment, the structure of any of the hematoxylin structures herein and the anchorable derivatives thereof comprise the oxidized form of hematoxylin, called hematein.

In one embodiment, the anchorable eosin comprises eosin with a moiety capable of anchoring to the polymer. In one embodiment the anchorable eosin is a compound of formula (III) or (IV):

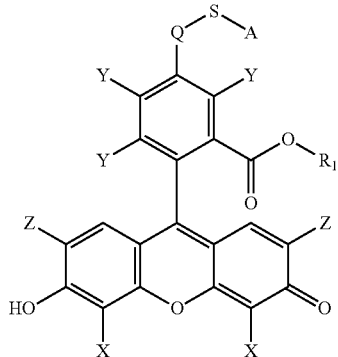

III

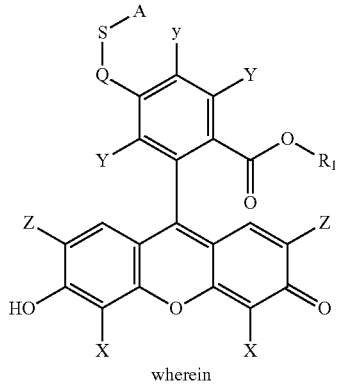

IV wherein

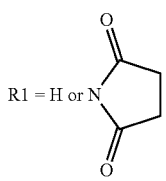

R1 = H or N(succinimide)

X = Z = Br, Y = H    Eosin Y
X = Br = NO₂, Y = H  Eosin B
X = Z = I, Y = H     Erythroosine B
X = Z = Br, Y = Cl   Phloxine B and wherein Q is O or NH, S is a spacer or a bond, and A is an anchorable moiety capable of being polymerized into a hydrogel matrix.

In one embodiment, S is selected from

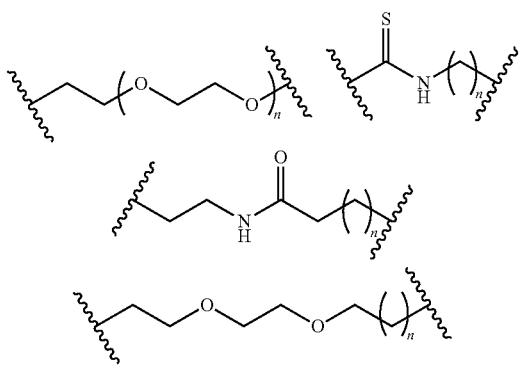

wherein n is an integer from 1 to 10.

In one embodiment, A is selected from a methacrylate, an acrylate, an acrylamide, a monoalkylacrylamide, a vinylalcohol, a vinylamine, an allylamine or an allylalcohol moiety.

In one embodiment, A is selected from:

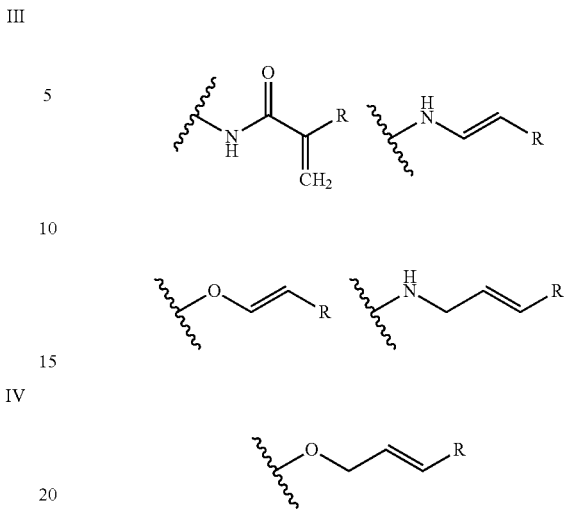

wherein R is H, alkyl, acyl, or nitrile.

In one embodiment, the alkyl is a $C_{1-6}$alkyl group, such as but not limited to methyl, ethyl, n-propyl, isopropyl, allyl, n-butyl, sec-butyl, isobutyl, tert-butyl, n pentyl, sec-pentyl, isopentyl, tert-pentyl, n-hexyl or sec-hexyl. In one embodiment, the acyl is selected from methanoyl, ethanoyl, propanoyl, isopropanoyl, butanoyl, isobutanoyl, t-butanoyl, pentanoyl, isopentanoyl, neopentanoyl or benzoyl.

In one embodiment, the anchorable eosin has formula IIIA, IIIB, IIIC, IVA or IVB:

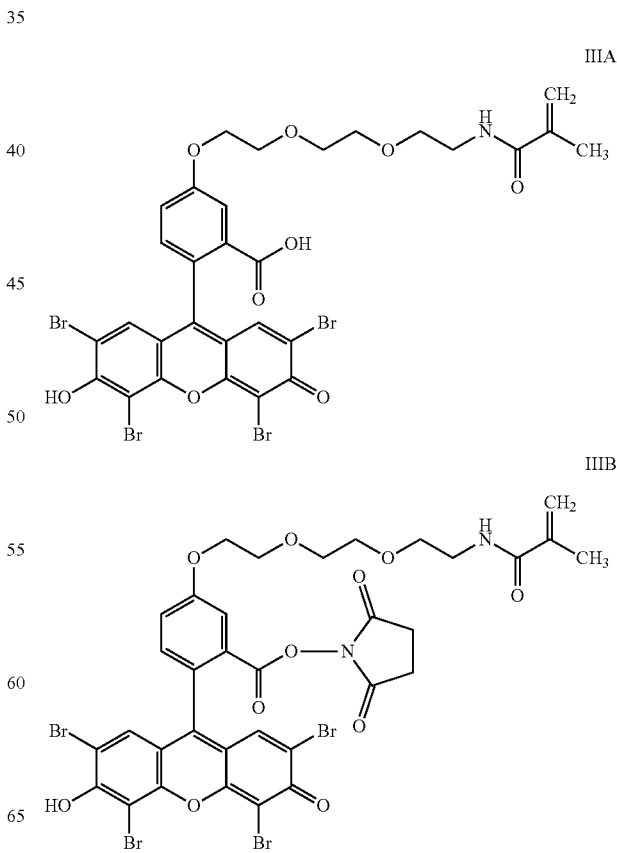

IIIA

IIIB

IIIC

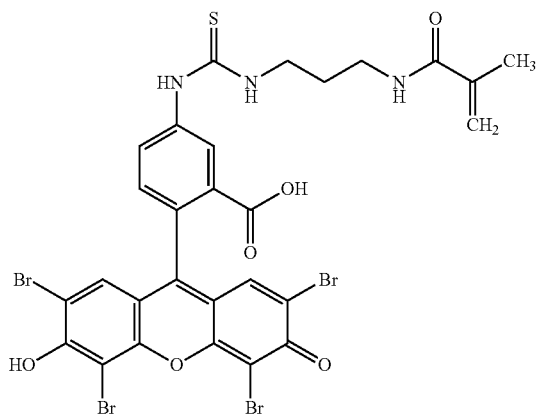

IVA

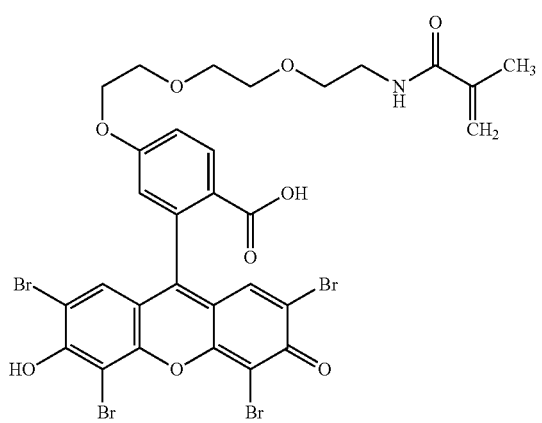

IVB

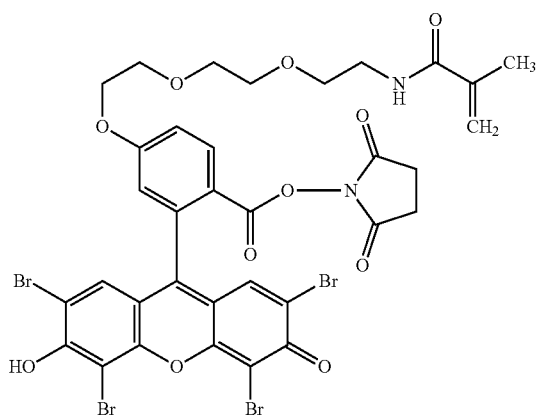

In one embodiment, an enlargeable sample of interest produced by the method of any of the foregoing embodiments. In one embodiment, the sample is embedded in a swellable material characterized by the isotropic expansion of the sample in 3-dimensions.

These and other aspects of the invention will be appreciated from the ensuing description of the figures and detailed description of the invention.

BRIEF DESCRIPTION OF THE FIGURES

Other aspects, advantages and novel features of the invention will become more apparent from the following detailed description of the invention when considered in conjunction with the accompanying drawings wherein.

DETAILED DESCRIPTION OF THE INVENTION

Figure 1:
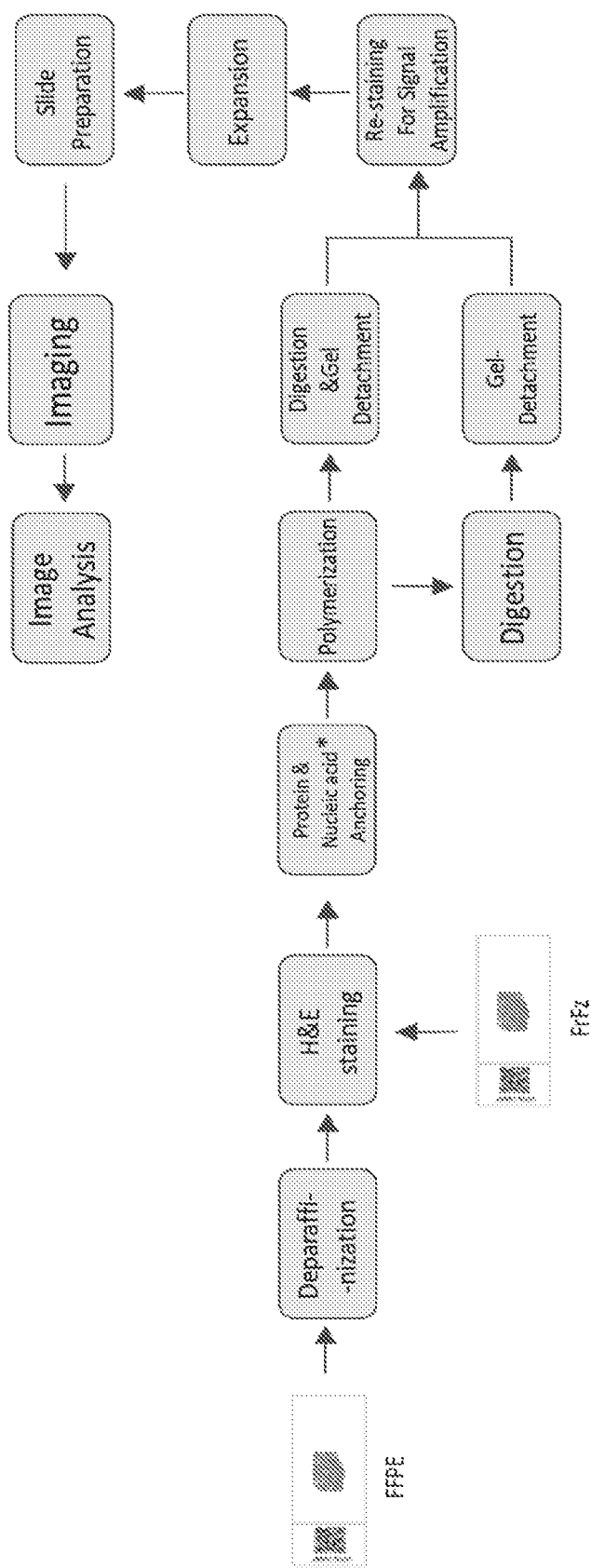
FIG. 1 is a schematic representation use of a protocol for hematoxylin and eosin labels of specimens in expansion microscopy.

The present invention employs the technique of expansion microscopy (ExM) in combination with hematoxylin and eosin (H&E) staining of tissue specimens within tissue samples, in order to achieve using light microscopic methods high resolution detection of biomolecules with precise morphological features of cells and nuclei, which in turn, allows for effective for accurate early stage disease diagnosis of various conditions and diseases, including various cancers. In the ExM procedure, fixed or previously frozen tissue specimens stained as described herein with H&E dyes, are permeated with a solution of water soluble small-molecule monomers which are polymerized into a swellable hydrogel that can be expanded 100 to 1000 times volumetrically upon addition of water or another liquid, allowing for an enhancement in resolution and specimen clearing. Anchor reagents such as 6-((acryloyl) amino) hexanoic acid succinimidyl ester ("Acryloyl-X", "AcX" or "Ac-X") for proteins, and NucliX (3-acrylamide-N-(3-((4-((2-chloroethyl)(methyl)amino)benzyl)amino)propyl)-N,N-dimethyl-propan-1-ammonium 2,2,2-salt) for nucleic acids, may be used in the ExM process to affix the biomolecules in the specimen to the hydrogel before expansion.

As noted herein, anchorable hematoxylin and eosin derivatives may be used to both stain and anchor to the hydrogel. In one embodiment using anchorable hematoxylin and eosin, AcX is also used, but NucliX is not. The expanded hydrogel specimens are then transferred onto a slide and imaged. These tissue specimens can be re-stained if desired for signal amplification.

In one embodiment, the biological specimen is stained with conventional H&E dyes before being subjected to the ExM procedure. In one embodiment, anchorable derivatives of hematoxylin and eosin are provided that stain the specimen as well as having an anchor moiety that can be polymerized in the hydrogel. Such derivatives comprise the dye moiety and a polymerizable moiety. In one embodiment, such anchorable hematoxylin and eosin derivatives comprise an acryloyl moiety and may be referred to herein as AcH and AcE, respectively. Other anchorable derivatives of these dyes are also embodied within the invention.

These and other features of the invention will be apparent from the description below, first including a general description of the ExM process.

The present invention is an expansion upon a method for optical imaging of biological specimens with resolution better than the classical microscopy diffraction limit, based on physically expanding the specimen itself. In this method, cultured cells, fixed tissue, or in principle any other type of sample of interest, including biological materials, are infused with a composition, or chemical cocktail, that results in it becoming embedded in the sample material, and then the composition can be expanded isotropically, preferably with nanoscale precision, in three dimensions. Fresh, frozen, formalin-fixed, or formalin-fixed and paraffin embedded specimens can be utilized in the process, among others. Such specimens can be prepared, thawed, deparaffinized, and any other treatment to render the sample ready for the ExM process.

In an embodiment of this ExM concept, the composition comprises a polyelectrolyte hydrogel (or the components thereof), which can swell macroscopically, for example, in low-salt (low ionic strength) water. The composition can comprise a tag or other feature of interest (for example, labeled antibody staining, or the H&E staining described herein) which can be anchored (e.g., chemically) into the hydrogel before expansion. Following anchoring, the specimen is subjected to an enzymatic (or other) digestion means to disrupt the underlying network of biological molecules, leaving the tags of interest (e.g., labeled antibody, stain) intact and anchored to the gel. In this way, the mechanical properties of the gel-biomolecule hybrid material are rendered more spatially uniform, allowing isotropic expansion with minimal artifacts.

The swollen material with its embedded biological specimen can be imaged on any optical microscope, allowing effective imaging of features below the classical diffraction limit. Since the resultant specimen can be transparent, custom microscopes capable of large volume, wide field of view, fast 3-D scanning may also be used in conjunction with the expanded sample.

This ExM technology enables new kinds of scientific exploration, such as mapping the brain, discovering the tumor heterogeneity in tumor microenvironment, as well as new diagnostic, personalized medicine, histopathological, and other medical capabilities.

In another aspect, the invention provides a microscopy method for producing a high-resolution image of a sample, the method comprising enlarging a sample of interest and viewing the enlarged sample under a microscope. In one embodiment, enlarging the sample of interest comprises embedding a sample of interest in a swellable material and then swelling the material. In certain embodiments, the sample of interest is labeled.

In a further aspect, the invention provides a method for the optical imaging of a sample of interest with resolution better than the classical microscopy diffraction limit, based on physically expanding the sample itself. In one embodiment, the method comprises embedding a sample of interest in a swellable material and then swelling the material. In certain embodiments, the sample of interest is labeled.

As used herein, the term "sample of interest" generally refers to, but not limited to, a biological, chemical or biochemical sample, such as a cell, array of cells, tumor, tissue, cell isolate, biochemical assembly, or a distribution of molecules suitable for microscopic analysis. The sample may be a thin section of a frozen or paraffin embedded tissue or other biological specimen section, and may be attached to a microscope slide. The specimen may have been previously preserver in formalin, alcohol, or another fixative. These are merely examples of the plethora of specimens amenable to the methods described herein.

As used herein, the term "swellable material" generally refers to a material that expands when contacted with a liquid, such as water or other solvent. Preferably, the swellable material uniformly expands equally in 3 dimensions (i.e., isotropically). Additionally or alternatively, the material is transparent such that, upon expansion, light can pass through the sample. In one embodiment the swellable material is a swellable polymer or hydrogel. In one embodiment, the swellable material is formed in situ from precursors thereof. For example, one or more polymerizable materials, monomers or oligomers can be used, such as monomers selected from the group consisting of water soluble groups containing a polymerizable ethylenically unsaturated group. Monomers or oligomers can comprise one or more substituted or unsubstituted methacrylates, acrylates, acrylamides, monoalkylacrylamide including but not limited to methyl, ethyl, propyl or isopropyl acrylamide, dialkylacrylamides such as dimethylacrylamide and diethylacrylamide, vinylalcohols, vinylamines, allylamines, allylalcohols, including divinylic crosslinkers thereof (e.g., N,N-alkylene bisacrylamides). Precursors can also comprise polymerization initiators and crosslinkers. In a preferred embodiment, the swellable polymer is polyacrylate and copolymers or crosslinked copolymers thereof. Alternatively or additionally, the swellable material can be formed in situ by chemically crosslinking water soluble oligomers or polymers. Thus, the invention envisions adding precursors (such as water soluble precursors) of the swellable material to the sample and rendering the precursors swellable in situ.

In an embodiment, embedding the sample in a swellable material comprises permeating (such as, perfusing, infusing, soaking, adding or other intermixing) the sample with the swellable material, preferably by adding precursors thereof. Alternatively or additionally, embedding the sample in a swellable material comprises permeating one or more monomers or other precursors throughout the sample and polymerizing and/or crosslinking the monomers or precursors to form the swellable material or polymer. In this manner the sample of interest is embedded in the swellable material.

Thus, a preferred embodiment of the invention a sample of interest, or a labeled sample, is permeated with a composition comprising water soluble precursors of a water swellable material and reacting the precursors to form the water swellable material in situ.

In certain embodiments, the sample of interest, or a labeled sample, can, optionally, be treated with a detergent prior to being contacted with the one or more swellable material precursors. The use of a detergent can improve the wettability of the sample or disrupt the sample to allow the one or more swellable monomer precursors to permeate throughout sample.

In a preferred embodiment, the sample is permeated with one or more monomers or a solution comprising one or more monomers or precursors which are then reacted to form a swellable polymer. For example, if the sample of interest is to be embedded in sodium polyacrylate, a solution comprising the monomers sodium acrylate and acrylamide, and the cross-linker N,N-methylenebisacrylamide or dimethylacrylamide are perfused throughout the sample. In one embodiment, the proportion of these components in the embedding solution are provided to result in a polymer that is optimally swellable. Once the sample, or labeled sample, is permeated, the solution is activated to form sodium polyacrylate. The monomer solution may also include accelerators of the polymerization process. In a preferred embodiment, the solution comprising the monomers is aqueous. The solution is preferably at high concentration, such as about 50% or more saturation (defined herein as the percentage of solids present in the aqueous solvent in the same ratio as would result in precipitation under the conditions of permeation). The solution is preferably at high concentration, such as about 75% or more saturation, more preferably 90% or more saturation.

In a preferred embodiment, the sample (e.g., a labeled sample) is anchored and crosslinked to the swellable material before expansion. This can preferably be accomplished by chemically crosslinking a tag or label with the swellable material, such as during or after the polymerization or in situ formation of the swellable material. In one embodiment, the crosslinking is achieved using a reagent such as glutaraldehyde or AcX, and NucliX, as described herein for protein and nucleic acid crosslinking, respectively. In certain embodiments, the dyes or stains used to label biomolecules of interest (e.g., nucleic acids and proteins) have the ability to crosslink the biomolecule of interest to the swellable material by means of an anchorable moiety on the dye or stain (for example, the anchorable hematoxylin and eosin derivatives described herein). In one embodiment, anchorable dyes are used and a protein cross-linking agent is used, but an additional nucleic acid cross-linking agent such as NucliX is not used. In one embodiment, after the labeled sample has been anchored to the swellable material, the sample is, optionally, subjected to a disruption of the endogenous biological molecules (or the physical structure of the sample of interest, where the sample is other than a biological material), leaving the tags or fluorescent dye molecules intact and anchored to the swellable material. In this way, the mechanical properties of the sample-swellable material complex are rendered more spatially uniform, allowing isotropic expansion with minimal artifacts.

Anchorable with respect to hematoxylin, eosin, or any derivative thereof, refers to a property of the dye after chemical modification as described herein, wherein a moiety is appended to the dye molecule making the dye capable of being polymerized into a hydrogel of the expansion microscope (ExM) procedure. In one embodiment, the anchorable moiety is an acryloyl moiety, enabling the anchorable dye to be polymerized into an acrylate hydrogel during the embedding and polymerization process. Other anchorable moieties may be used to incorporate the dye into the same or different hydrogels. As described herein, these dyes, which have particular affinities to nucleic acids and proteins in biological specimens, by using their anchorable versions, improves the inclusion of the dyes in the expansion microscopy procedure.

In one embodiment, a combination of an anchorable and non-anchorable dye is used, with or without cross-linking agents. In one embodiment, when a non-anchorable hematoxylin is used, a protein cross-linker (e.g., glutaraldehyde, AcX) is used, but no nucleic acid crosslinker is used. As used herein, non-anchorable refers to the native dyes described here that are not derivatized via the -Q-S-A group.

In one embodiment when an anchorable hematoxylin and a non-anchorable eosin are used, a protein cross-linking agent is used (e.g., glutaraldehyde, AcX). In one embodiment, when an anchorable hematoxylin and a non-anchorable eosin are used, a protein cross-linking agent (e.g., glutaraldehyde, AcX) and a nucleic acid cross-linking agent (e.g., NucliX) are used. In one embodiment, when a non-anchorable hematoxylin and an anchorable eosin are used, no cross-linking agents are used. In one embodiment, when a non-anchorable hematoxylin and an anchorable eosin are used, a nucleic acid cross-linking agent (e.g., NucliX) is used. In one embodiment, when a non-anchorable hematoxylin and an anchorable eosin are used, a protein cross-linking agent (e.g., glutaraldehyde, AcX) and a nucleic acid cross-linking agent (e.g., NucliX) are used. In other embodiments, staining and re-staining may be performed with anchorable followed by non-anchorable dyes, or non-anchorable dye followed by anchorable dye, and in other embodiments, any of the combinations described above in any order. In one embodiment, anchorable dyes are used first and non-anchorable dyes are used for restaining. In one embodiment, the non-anchorable hematoxylin provides adequate cross-linking of nucleic acids to the hydrogel matrix or to other biomolecules in the sample to not require the use of a separate nucleic acid cross-linker (e.g., NucliX). In one embodiment, the anchorable eosin provides adequate cross-linking of proteins to the matrix or other biomolecules in the sample to not require the use of a separate protein cross-linker (e.g., glutaraldehyde or AcX).

In one embodiment, the protein cross-linking agent is used before or after the anchorable eosin is used. In one embodiment, the nucleic acid cross-linking agent is used before or after the anchorable hematoxylin is used. In one embodiment, the protein cross-linking agent is used before or after the anchorable hematoxylin, anchorable eosin, or both are used. In one embodiment, the nucleic acid cross-linking agent is used before or after the anchorable hematoxylin, anchorable eosin, or both are used. In one embodiment, the protein cross-linking agent and the nucleic cross-linking agent are used before, simultaneously, or after the anchorable or non-anchorable dyes are used in any combination and in any order. In another embodiment, the protein cross-linking agent, the nucleic acid cross-linking agent, the anchorable hematoxylin, the anchorable eosin, hematoxylin and eosin may be used in any combination and in any order.

In embodiments of the invention, the staining or labeling step may be performed with both dyes simultaneously, or they may be used successively, and in any order. In embodiments of the invention where both a protein and a nucleic acid cross-linker are used, they may be used simultaneously or successively, and in any order.

In other embodiments, both an anchorable and non-anchorable dye (i.e., either form of hematoxylin or either form of eosin) may be used, with one or both of the other dyes. In one embodiment any combination of hematoxylin, anchorable hematoxylin, eosin and anchorable eosin are used, together or successively in any combination, provided that at least one anchorable form of hematoxylin or one form of anchorable eosin is employed.

As used herein, the "disruption of the endogenous biological molecules" of the sample of interest generally refers to the mechanical, physical, chemical, biochemical or, preferably, enzymatic digestion, disruption or break up of the sample so that it will not resist expansion. In an embodiment, a protease enzyme is used to homogenize the sample-swellable material complex. Disruption may be partial. It is preferable that the disruption does not impact the structure of the swellable material but disrupts the structure of the sample. Thus, the sample disruption should be substantially inert to the swellable material. The degree of digestion can be sufficient to compromise the integrity of the mechanical structure of the sample or it can be complete to the extent that the sample-swellable material complex is rendered substantially free of the sample.

The sample-swellable material complex is then isotropically expanded. Preferably, a solvent or liquid is added to the complex which is then absorbed by the swellable material and causes swelling. Where the swellable material is water swellable, an aqueous solution can be used. In one embodiment a low ionic strength salt solution is used.

In one embodiment, the addition of water allows for the embedded sample to expand 4× to 5× (e.g., 4.5×) or more its original size in 3-dimensions. Thus, the sample can be increased 100-fold or more in volume. This is because the polymer is embedded throughout the sample, therefore, as the polymer swells (grows) it expands the tissue as well. Thus, the tissue sample itself becomes bigger. Surprisingly, as the material swells isotropically, the anchored tags maintain their relative spatial relationship.

The swollen material with the embedded sample of interest can be imaged on any optical microscope, allowing effective imaging of features below the classical diffraction limit. Since the resultant specimen is preferably transparent, custom microscopes capable of large volume, wide field of view, 3-D scanning may also be used in conjunction with the expanded sample.

In one embodiment, the enzymatic digestion is achieved using conditions described in WO2017/147435, incorporated herein by reference. In one example, the sample is incubated with 1-100 U/ml of a non-specific protease in a buffer having a pH between about 4 and about 12, the buffer comprising about 5 mM to about 100 mM metal ion chelator, about 0.1% to about 1.0% non-ionic surfactant, and about 0.05 M to about 1 M monovalent salt. The expandable biological specimen can be expanded by contacting the swellable polymer with a solvent or liquid to cause the swellable polymer to swell. In one embodiment, prior to the treating step (a), the sample is heat treated. In one embodiment, the samples are digested with 8 units/mL proteinase K solution containing 25 mM Tris (pH 8), 1 mM EDTA, 0.25% Triton X-100, and 0.4 M NaCl In one embodiment, the aforementioned expansion process may be repeated to achieve even further enlargement of the specimen. As described in U.S. Ser. No. 15/098,799, incorporated herein by reference, the process of iteratively expanding the samples can be applied to samples that have been already expanded using ExM techniques one or more additional times to iteratively expand them such that, for example, a 5-fold expanded specimen can be expanded again 3- to 4-fold, resulting in as much as a 17- to 19-fold or more linear expansion. In one example of the steps of the iterative process, (a) embedding a labelled sample of interest in a first swellable material comprising a first cleavable cross linking material, wherein the sample of interest is labelled with a first label comprising at least one functional moiety capable of linking to the first swellable material; (b) swelling the first swellable material to form a first enlarged sample that is enlarged as compared to the sample of interest; (c) re-embedding the first enlarged sample in a non-swellable material comprising a cleavable crosslinking material; (d) labelling the first enlarged sample with a second detectable label that is capable of linking to the first label; e) embedding the labelled first enlarged sample in a second swellable material comprising a second cleavable cross linking material wherein the second cleavable crosslinking material is different from the first cleavable crosslinking material and wherein the second cleavable crosslinking material is not cleavable under the same conditions as the cleavable linkers of steps (a) and (c) and wherein the second label comprises at least one functional moiety capable of linking the second label to the second swellable material; f) cleaving the cleavable linker of steps (a) and (c); and g) swelling the second swellable material to form a second enlarged sample that is enlarged as compared to the first enlarged sample. In one embodiment, the staining using H&E or the derivatives described here can also be iterated at appropriate stages, to increase the staining of desired biomolecules in the sample.

In one embodiment, the process of protein retention expansion microscopy (proExM) can be carried out on a biological sample to be stained using the H&E or derivatives of the invention. In accordance with U.S. Ser. No. 15/229,545, incorporated herein by reference, proteins, rather than labels, are anchored to the swellable gel, using a cross-linking molecule. This proExM strategy can be used to perform nanoscale imaging of immunostained cells and tissues as well as samples expressing various fluorescent proteins as fluorescent signals from genetically encoded fluorescent proteins and/or conventional fluorescently labeled secondary antibodies and streptavidin that are directly anchored to the gel are preserved even when subjected to the nonspecific proteolytic digestion.

As noted above, in one embodiment of the invention, H&E staining is used to label biomolecules in the specimen before the specimen undergoes the ExM process. In one embodiment the H&E staining comprises overstaining, such that after expansion of the sample the labeled biomolecules are detectable. In one embodiment overstaining comprises exposing the sample to the dye or stain at a higher concentration, for a longer period, at an elevated temperature, or any combination thereof. In another embodiment other components to enhance the extent of staining may be included, such a concentration or higher concentration of a solvent, a lower of higher ionic strength, by ways of non-limiting examples. The extent of overstaining would render a non-expanded specimen uninterpretable, but using the ExM technique, provides the requisite level of staining. In another embodiment, the biological sample can be stained in accordance with the teachings herein after expansion, or both before and after expansion. In another embodiment, that will be elaborated upon in detail below, the biomolecules in the specimen can be stained with derivatives of hematoxylin and eosin that contain moieties that can be polymerized into the hydrogel, thus retaining their label function and also their spatial location function. Use of such derivatives facilitates staining and preservation of detectable staining after specimen expansion.

In one embodiment, in addition to the H&E staining by any of the herein described methods and reagents, the sample of interest can be labeled or tagged to identify other biomolecules or structures of interest therein. Typically, the label or tag will bind chemically (e.g., covalently, hydrogen bonding or ionic bonding) to the sample, or a component thereof. The tag can be selective for a specific target (e.g., a biomarker or class of molecule), as can be accomplished with an antibody or other target specific binder. The tag preferably comprises a visible component, as is typical of a dye or fluorescent molecule. Contacting the sample of interest with a label or tag results in a "labeled sample of interest." A fluorescently labeled sample of interest, for example, is a sample of interest labeled through techniques such as, but not limited to, immunofluorescence, immunohistochemical or immunocytochemical staining to assist in microscopic analysis. Thus, the label or tag is preferably chemically attached to the sample of interest, or a targeted component thereof. In a preferred embodiment, the label or tag, e.g., the antibody and/or fluorescent dye, further comprises a physical, biological, or chemical anchor or moiety that attaches or crosslinks the sample to the composition, hydrogel or other swellable material. The labeled sample may furthermore include more than one label. For example, each label can have a particular or distinguishable fluorescent property, e.g., distinguishable excitation and emission wavelengths. Further, each label can have a different target specific binder that is selective for a specific and distinguishable target in, or component of the sample. Descriptions of other labeling methods can be found in, as well as a description of the ExM process and variations thereupon, in for example, Chen et al., Science (January 2015), Expansion Microscopy, v347 (6221), pp. 543-548, U.S. Ser. No. 15/446,005, published as US 2017-0253918; U.S. Ser. No. 15/592,221, published as US 2018-0052081; International Application No. PCT/US2018/055242; International Application No. PCT/US2018/061931; U.S. Ser. No. 14/627,310, published as US-2016-0116384-A1; International Application No. PCT/US2015/16788; U.S. Ser. No. 15/098,799, published as US-2016-0305856-A1; U.S. Pat. No. 10,059, 999; U.S. Ser. No. 15/789,419, publishes as US-2018-0119219-A1; U.S. Ser. No. 15/229,539, published as US-2016-0305856-A1; International Application No. PCT/US2016/045751 and published as WO2017/027367; U.S. Ser. No. 15/229,545, published as US-2017-0089811; International Application No. PCT/US2016/045752, published as WO2017/027368; International Application No. PCT/US2017/19372, published as WO/2017/147435; International Application No. PCT/US2018/14629, published as WO2018/136856; International Application No. PCT/US2018/19694, published as WO2018/157048; and International Application No. PCT/US18/19756, published as WO/2018/157074; PCT/US2018/055254, published as WO2019/075091; all of the foregoing which are incorporated herein by reference in their entireties.

As mentioned above, derivatives of histological stains that comprise a moiety capable of being polymerized into the hydrogel matrix during the ExM process is an embodiment of the invention. Moieties on dyes such as but not limited to an ethylenically unsaturated group are embodied herein. Other moieties on the dye molecule include one or more substituted or unsubstituted methacrylates, acrylates, acrylamides, methacrylamides, vinylalcohols, vinylamines, allylamines, allylalcohols, including divinylic crosslinkers thereof (e.g., N,N-alkylene bisacrylamides). While the following description is applicable to hematoxylin and eosin, other derivatives of stains and dyes are embodied herein and may be derivatized with the same anchorable moieties as described herein for hematoxylin and eosin.

H&E staining is a well-established procedure for staining histologic specimens, and except for the variations described herein applicable to expansion microscopy and the use of anchorable derivatives of hematoxylin and eosin, the same methods and reagents are used. Guidance for H&E staining can be found in numerous sources well known to one of skill in the art. The staining solutions, clearing steps and process, bluing solution and process, and sample handling, washing, etc. are based on established reagents and procedures.

In one embodiment, instead of the natural H&E stains used as described above, the ExM process is carried out on samples stained with derivatives of hematoxylin and eosin that comprise an anchorable group, such that these dyes, in addition to staining the biomolecules in the sample, are also capable of being covalently bound to the hydrogel matrix in the ExM process, anchoring the biomolecule to the dye to the polymer matrix. A description of such anchorable hematoxylin and anchorable eosin derivatives is provided below.

In some embodiments, the dye phloxine or erythrosine is used together with or in place of eosin. Anchorable phloxine and erythrosine derivatives are also embodied herein. As noted above, in other embodiment, anchorable derivatives of other dyes are also useful for the purposes herein.

Hematoxylin and Anchorable Hematoxylin Derivatives

Hematoxylin is a natural product extracted from the heartwood of the logwood tree (*Haematoxylin campechianum*). Hematoxylin is relatively colorless and without further modifications has little or no value as a biological stain. The use of the word "hematoxylin" to describe a staining solution is somewhat misleading but continues to be used as a term of convenience. To produce a functional dye, hematoxylin is oxidized to hematein as shown below

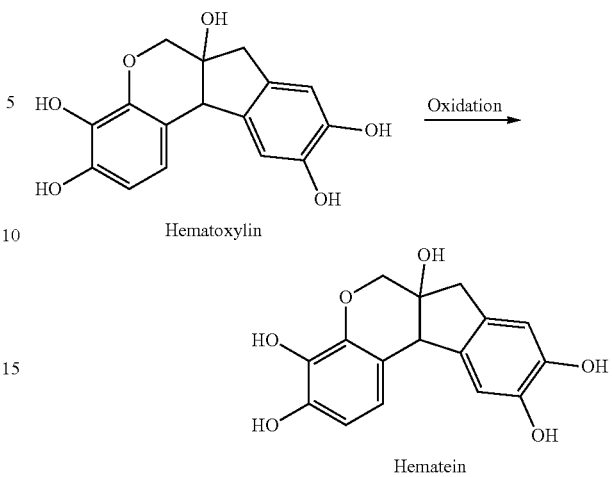

and subsequently is bound to one of several metal ions including aluminum (Al+3), iron (Fe+3) and chromium (Cr+3). A metallic ion bound to a dye that is involved in the binding of the dye to tissue is referred to as a mordant. Herein, hematoxylin and hematoxylin derivatives are intended to describe both forms of the molecule, derived from either hematoxylin or hematein, and structure of the oxidation product is incorporated into the structures throughout the descriptions herein. In one embodiment, the compounds described herein are synthesized as anchorable hematoxylins and are subsequently oxidized (ripened) to the hematein analogues after synthesis. In one embodiment the hematein analogue of hematoxylin is derivatized to the anchorable form of hematein by the synthetic methods described herein applied to a derivatizable hematein as the starting reagent.

Hematoxylin is a dark blue or violet stain that is basic/positive. It binds to basophilic substances (such as DNA and RNA, which are acidic and negatively charged). DNA/RNA in the nucleus, and RNA in ribosomes in the rough endoplasmic reticulum are both acidic because the phosphate backbones of nucleic acids are negatively charged. These backbones form salts with basic dyes containing positive charges. Therefore, dyes like hematoxylin bind to DNA and RNA and stain them violet.

The structure of hematoxylin is shown as compound (I) below.

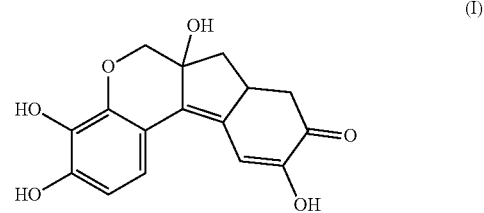 [SMILES: O=C1CC2CC3(O)COc4c(ccc(O)c4O)C3=C2C=C1O]

For use in one of the embodiments of the invention, anchorable hematoxylin derivatives are prepared that are capable of being polymerized into the hydrogel matrix central to ExM. In one embodiment, a hematoxylin derivative is provided comprising at least one anchorable moiety, shown as the -Q-S-A moiety on the hematoxylin structure shown in formula (II), wherein Q is O or NH, S is a spacer and A is an anchorable moiety. In some embodiments the —OH moiety to which the S-A moiety is attached is replace with an NH (herein depicted as Q). Various anchorable moieties on the hematoxylin molecule capable of participating in the polymerization are embodied herein, such as but not limited to a methacrylate, an acrylate, an acrylamide, a monoalkylacrylamide including but not limited to methyl, ethyl, propyl or isopropyl acrylamide, a vinylalcohol, a vinylamine, an allylamine or an allylalcohol moiety. The spacer may be absent, i.e., a bond, or may be present.

In one embodiment, the anchorable moiety comprises an acryloyl moiety.

In one embodiment, a spacer may be provided between the hematoxylin and the anchorable moiety, to facilitate synthesis or to provide a distance between the anchorable moiety and the hematoxylin molecule. It may also improve solubility.

In one embodiment, the anchorable hematoxylin comprises a moiety capable of anchoring to the polymer. In one embodiment, the anchorable hematoxylin is a compound of formula (II):

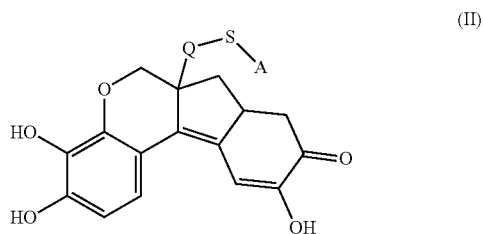

(II)

wherein Q is O or NH, S is a spacer or a bond, and A is an anchorable moiety capable of being polymerized into a hydrogel matrix.

In one embodiment, S is selected from

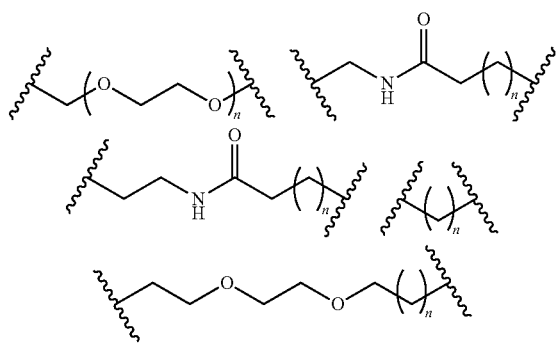

wherein n is an integer from 1 to 10.

In one embodiment, n is an integer from 1 to 5. In one embodiment, n is 1, 2, 3, 4, 5, 6, 7, 8, 9, or 10.

In one embodiment, A is selected from a methacrylate, an acrylate, an acrylamide, a monoalkylacrylamide, a vinylalcohol, a vinylamine, an allylamine or an allylalcohol moiety.

In one embodiment, A is selected from:

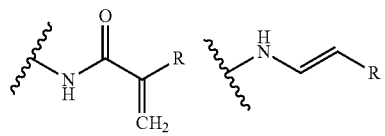

-continued

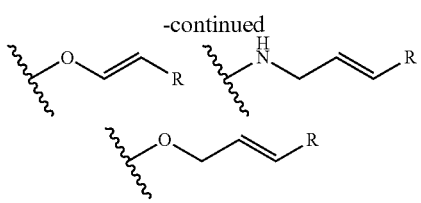

wherein R is H, alkyl, acyl, or nitrile.

In one embodiment, the alkyl is a $C_{1-6}$alkyl group. In one embodiment, the acyl is selected from methanoyl, ethanoyl, propanoyl, isopropanoyl, butanoyl, isobutanoyl, t-butanoyl, pentanoyl, isopentanoyl, neopentanoyl or benzoyl.

In some embodiments, the anchorable moiety is a methacrylate. In one embodiment, the methacrylate moiety of the anchorable hematoxylin may be polymerized into a hydrogel matrix comprising monomers such as sodium acrylate, acrylamide, and dimer N',N'-methylene bisacrylamide, in which, in one embodiment, polymerization may be initiated using ammonium persulfate and accelerated using TEMED.

In some embodiments, the anchorable moiety is an acrylate. In one embodiment, the acrylate moiety of the anchorable hematoxylin may be polymerized into a hydrogel matrix comprising monomers such as sodium acrylate, acrylamide, and dimer N',N'-methylene bisacrylamide, in which, in one embodiment, polymerization may be initiated using ammonium persulfate and accelerated using TEMED.

In some embodiments, the anchorable moiety is an acrylamide. In one embodiment, the acrylamide moiety of the anchorable hematoxylin may be polymerized into a hydrogel matrix comprising monomers such as sodium acrylate, acrylamide, and dimer N',N'-methylene bisacrylamide, in which, in one embodiment, polymerization may be initiated using ammonium persulfate and accelerated using TEMED.

In some embodiments, the anchorable moiety is a monoalkylacrylamide, such as but not limited to methyl, ethyl, propyl or isopropyl acrylamide. In one embodiment, the monoalkylacrylamide moiety of the anchorable hematoxylin may be polymerized into a hydrogel matrix comprising monomers such as sodium acrylate, acrylamide, and dimer N',N'-methylene bisacrylamide, in which, in one embodiment, polymerization may be initiated using ammonium persulfate and accelerated using TEMED.

In some embodiments, the anchorable moiety is a vinylalcohol.

In some embodiments, the anchorable moiety is a vinylamine.

In some embodiments, the anchorable moiety is an allylamine.

In some embodiments, the anchorable moiety is an allylalcohol moiety.

As noted herein, a spacer may be interposed between the anchorable moiety and the hematoxylin. Non-limiting examples of spacers are described below. The spacer may be selected for optimal coupling of the hematoxylin to the anchorable moiety, or may be selected to optimally separate the distance between the hematoxylin and the anchorable moiety for facile polymerization into the hydrogel matrix, or for improved solubility.

In some embodiments, the spacer is a polyethylene glycol spacer. In one embodiment, the polyethylene glycol spacer comprises 1, 2, 3, 4, 5, 6, 7, 8, 9, or 10 ethylene glycol units.

In some embodiments, the spacer is

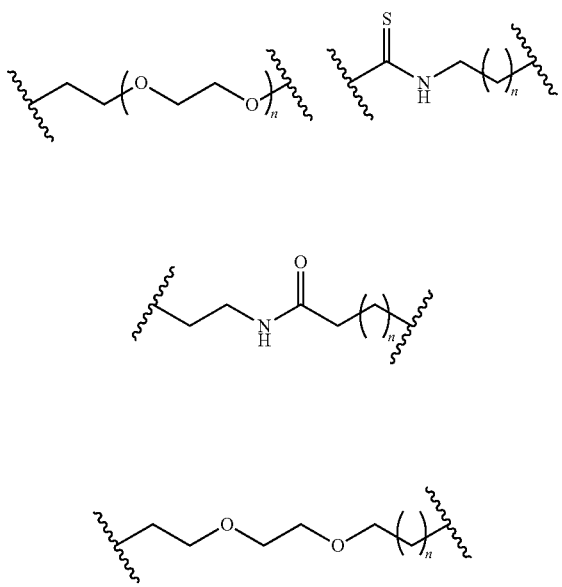

wherein is an integer from 1 to 5.

In some embodiments, the spacer is absent, and the anchorable moiety is directly bound to the hematoxylin molecule. In this embodiment, the spacer is referred to as a bond.

In one embodiment, the structure (II) and the anchorable derivatives thereof comprises the oxidized form of hematoxylin, called hematein and comprises a moiety capable of anchoring to the polymer. In one embodiment, the anchorable hematein is a compound of formula (V)

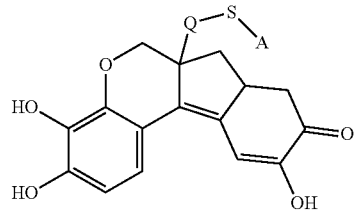

(V)

wherein Q is O or NH, and S and A are the same as described for anchorable hematoxylin, herein.

The anchorable hematoxylin and anchorable hematein compounds of the invention (herein referred to together as anchorable hematoxylin) may be synthesized by any number of synthetic schemes. In one embodiment, the anchorable hematoxylin of the invention is made by steps shown in Example 1.

In one embodiment, the compound is purified by silica column chromatography eluting either with individual or mixture of petroleum ether and ethyl acetate. Characterization is done by LCMS and proton NMR spectroscopy. In one embodiment, the compound is >98%, or is obtained by additional purification with preparative MPLC. Compounds are characterized by LCMS, HNMR, 13CNMR and HRMS.

In one embodiment, the anchorable hematoxylin has the structure IIA, IIB, IIC, IID or IIE:

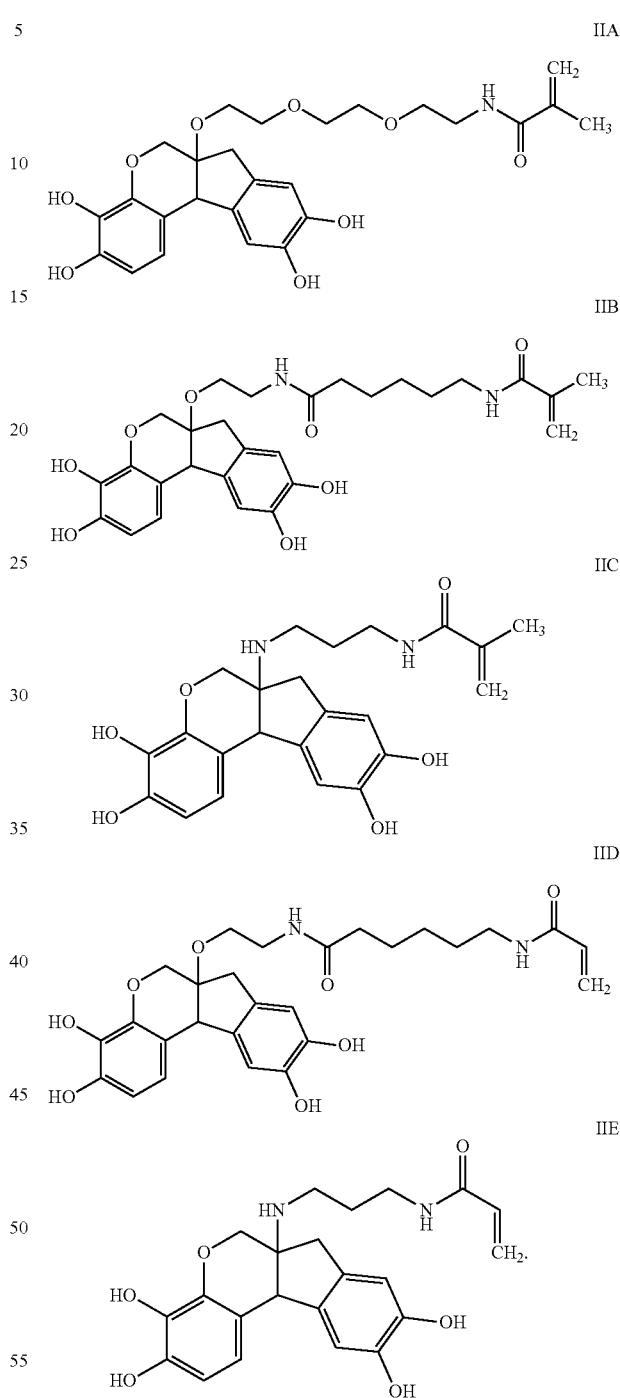

Eosin and Anchorable Eosin Derivatives

Eosin is a red or pink stain that is acidic and negative. It binds to acidophilic substances such as positively charged amino-acid side chains (e.g., lysine, arginine). Most proteins in the cytoplasm of some cells are basic because they are positively charged due to the arginine and lysine amino-acid residues. These form salts with acid dyes containing negative charges, like eosin. Therefore, eosin binds to these amino acids/proteins and stains them pink. This includes cytoplasmic filaments in muscle cells, intracellular membranes, and extracellular fibers.

There are two very closely related compounds commonly referred to as eosin. Most often used is Eosin Y (also known as eosin Y ws, eosin yellowish, Acid Red 87, C.I. 45380, bromoeosine, bromofluoresceic acid, D&C Red No. 22); it has a very slightly yellowish cast. The other eosin compound is eosin B (eosin bluish, Acid Red 91, C.I. 45400, Saffrosine, Eosin Scarlet, or imperial red); it has a very faint bluish cast. The two dyes are interchangeable, and the use of one or the other is a matter of preference and tradition. In addition, the related dyes phloxine and erythrosine are also derivatizable to anchorable dyes and are incorporated herein as well.

The structures of eosin Y and eosin B are shown below.

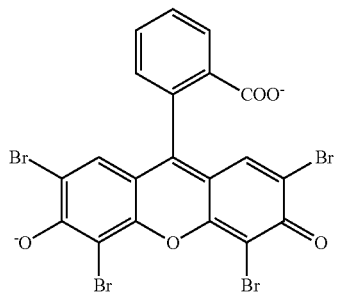

Eosin Y

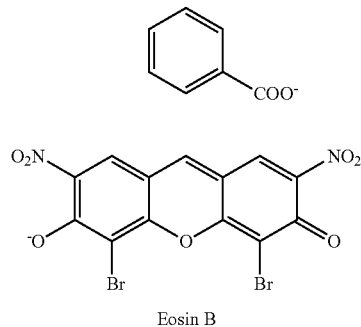

Eosin B

In one embodiment, the anchorable eosin comprises eosin with a moiety capable of anchoring to the polymer. In one embodiment the anchorable eosin is a compound of formula (III) or (IV)

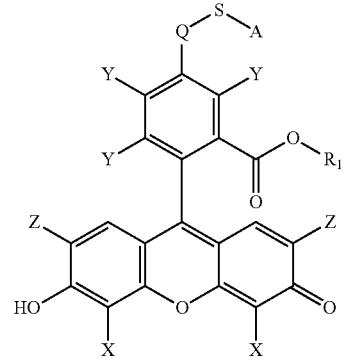

III

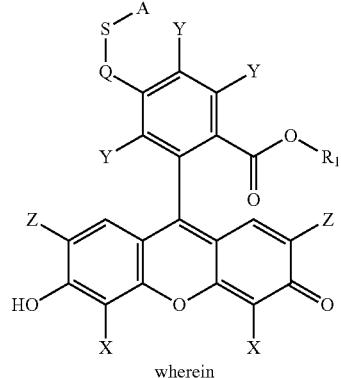

IV wherein

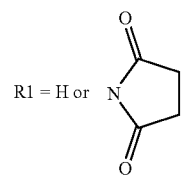

R1 = H or

X = Z = Br, Y = H     Eosin Y
X = Br = NO$_2$, Y = H     Eosin B
X = Z = I, Y = H     Erythroosine B
X = Z = Br, Y = Cl     Phloxine B and wherein Q is O or NH, S is a spacer or a bond, and A is an anchorable moiety capable of being polymerized into a hydrogel matrix.

As noted above, cosin may be any of the various related dyes with different substituents on the X, Y and/or Z groups on the structure of formula (III) or (IV). As noted, two isomers of anchorable eosin are embodied herein, wherein the -Q-S-A are at one of two positions.

As noted herein, a spacer may be interposed between the anchorable moiety and the eosin molecule. Non-limiting examples of spacers are described below. The spacer may be selected for optimal coupling of the eosin to the anchorable moiety, or may be selected to optimally separate the distance between the eosin and the anchorable moiety for facile polymerization into the hydrogel matrix, or to improve solubility.

In some embodiments, the spacer is a polyethylene glycol spacer. In one embodiment, the polyethylene glycol spacer comprises 1, 2, 3, 4, 5, 6, 7, 8, 9, or 10 ethylene glycol units.

In one embodiment, S is selected from

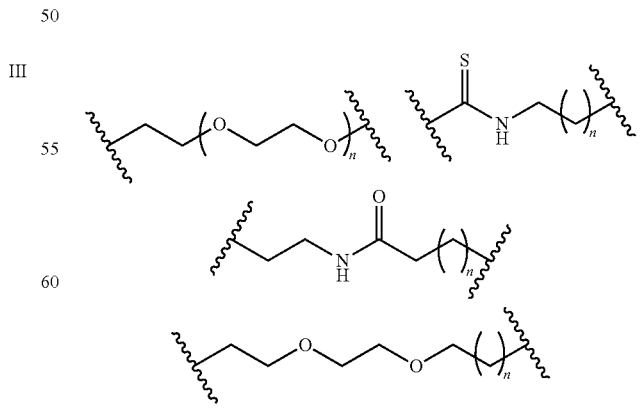

wherein n is an integer from 1 to 10.

In some embodiments, n is an integer from 1 to 5. In some embodiments n is 1, 2, 3, 4, 5, 6, 7, 8, 9 or 10.

In some embodiments, the spacer is absent, and the anchorable moiety is directly bound to Q. In this embodiment, the spacer is referred to as a bond.

Various anchorable moieties on the eosin molecule capable of participating in the polymerization are embodied herein, such as but not limited to a methacrylate, an acrylate, an acrylamide, a monoalkylacrylamide including but not limited to methyl, ethyl, propyl or isopropyl acrylamide, a vinylalcohol, a vinylamine, an allylamine or an allylalcohol moiety. The spacer may be absent, i.e., a bond, or may be present.

In one embodiment, A is selected from:

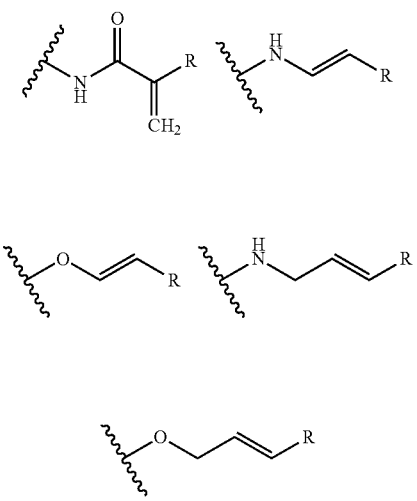

wherein R is H, alkyl, acyl, or nitrile.

In one embodiment, the alkyl is a $C_{1-6}$alkyl group. In one embodiment, the acyl is selected from methanoyl, ethanoyl, propanoyl, isopropanoyl, butanoyl, isobutanoyl, t-butanoyl, pentanoyl, isopentanoyl, neopentanoyl or benzoyl.

In one embodiment, the anchorable moiety comprises an acryloyl moiety.

In some embodiments, the anchorable moiety is a methacrylate. In one embodiment, the methacrylate moiety of the anchorable eosin may be polymerized into a hydrogel matrix comprising monomers such as sodium acrylate, acrylamide, and dimer N',N'-methylene bisacrylamide, in which, in one embodiment, polymerization may be initiated using ammonium persulfate and accelerated using TEMED.

In some embodiments, the anchorable moiety is an acrylate. In one embodiment, the acrylate moiety of the anchorable eosin may be polymerized into a hydrogel matrix comprising monomers such as sodium acrylate, acrylamide, and dimer N',N'-methylene bisacrylamide, in which, in one embodiment, polymerization may be initiated using ammonium persulfate and accelerated using TEMED.

In some embodiments, the anchorable moiety is an acrylamide. In one embodiment, the acrylamide moiety of the anchorable eosin may be polymerized into a hydrogel matrix comprising monomers such as sodium acrylate, acrylamide, and dimer N',N'-methylene bisacrylamide, in which, in one embodiment, polymerization may be initiated using ammonium persulfate and accelerated using TEMED.

In some embodiments, the anchorable moiety is a monoalkylacrylamide, such as but not limited to methyl, ethyl, propyl or isopropyl acrylamide. In one embodiment, the monoalkylacrylamide moiety of the anchorable eosin may be polymerized into a hydrogel matrix comprising monomers such as sodium acrylate, acrylamide, and dimer N',N'-methylene bisacrylamide, in which, in one embodiment, polymerization may be initiated using ammonium persulfate and accelerated using TEMED.

In some embodiments, the anchorable moiety is a vinylalcohol.

In some embodiments, the anchorable moiety is a vinylamine.

In some embodiments, the anchorable moiety is an allylamine.

In some embodiments, the anchorable moiety is an allylalcohol moiety.

The anchorable eosin and its other dye relatives of the invention (herein referred to as anchorable eosin) may be synthesized by any number of synthetic schemes. In one embodiment, the anchorable eosin of the invention is made by steps shown in Example 2.

In one embodiment, the compound is purified by silica column chromatography eluting either with individual or mixture of petroleum ether and ethyl acetate. Characterization is done by LCMS and proton NMR spectroscopy. In one embodiment, the compound is >98%, or is obtained by additional purification with preparative MPLC. Compounds are characterized by LCMS, HNMR, 13CNMR and HRMS.

In one embodiment, the anchorable eosin is:

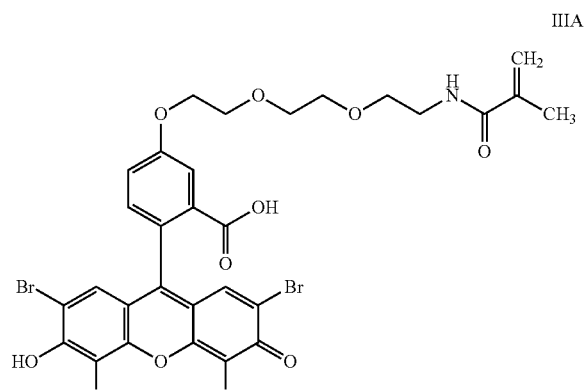

IIIA

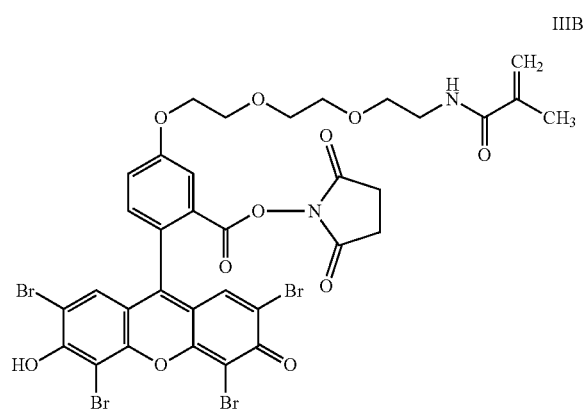

IIIB

IIIC

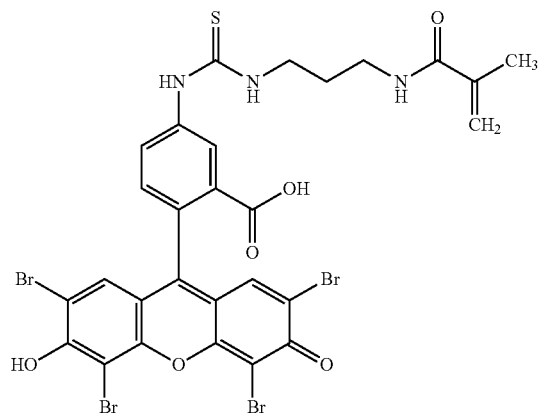

IVA

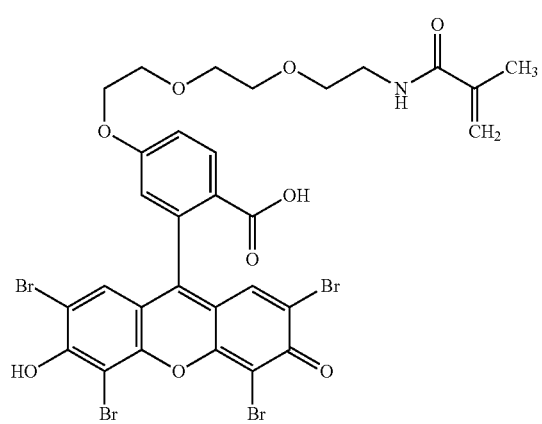

IVB

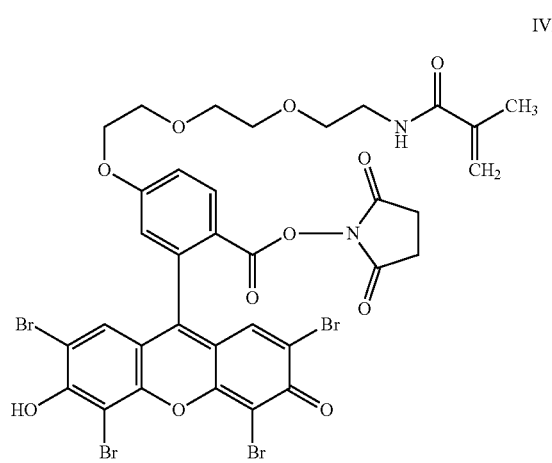

Descriptions of the synthesis of some non-limiting examples of anchorable hematoxylin and anchorable eosin derivatives are provided in the examples further below.

Expansion Microscopy Using Standard and Anchorable Dyes

The following descriptions of the steps for carrying out the invention are intended to provide general guidance and variations are within the intended scope of the invention. The examples provided further below give specific conditions, but these can be varied to achieve the purpose of the invention without deviating from the teaching herein.

Description of the process for using direct H&E staining (FIG. 1). In this process, the staining of the sample with H & E follow guidance well established in the art.

Sample. The sample may be, by way of non-limiting examples, fresh, formalin-fixed, alcohol-fixed, frozen, and fixed and paraffinized. In one embodiment, the sample is readied for the ensuing steps by providing the sample in an aqueous environment. In one embodiment a fixed sample is washed in water or saline to remove fixative before carrying out the ensuing steps. In one embodiment, an alcohol-preserved sample is transferred to an aqueous environment by progressive washing in a series of decreasing alcohol concentrations. In one embodiment a paraffinized sample is deparaffinized by washing with 100% xylenes, then with a mixture of xylenes and 100% ethanol, then with 100% ethanol, followed by decreasing concentrations of ethanol in water from 95%, 70%, 50% then water.

In one embodiment the sample is a thin section of a biological specimen, and may be mounted on a microscope slide. In other embodiment the specimen is a pathology specimen in formalin or alcohol fixative, or a frozen or fresh frozen biopsy specimen. In one embodiment the specimen is a thin section of a fresh frozen specimen. In one embodiment the specimen is a cleared specimen. In the instances where the specimen to be stained and expanded by the methods herein is a thin section adhered to a microscope slide, before expansion the thin section must be detached from the slide to allow for isotropic expansion; this step is included in the description below.

Staining. In one embodiment, the sample is stained first with anchorable hematoxylin, then with anchorable eosin. In one embodiment, the sample is stained with anchorable hematoxylin (0.01% to 10%), for 10-12 minutes, washed in running tap water, clarified with, for example, 1% acid alcohol, washed, incubated in bluing solution (for example, 0.2% ammonia water or saturated lithium carbonate solution) then washed. The sample is then washed with 95% ethanol, and stained with anchorable eosin Y (0.01% to 10%). Staining may be from 15 minutes to overnight, the sample is then washed with 95% ethanol, then proceed to polymerization. In one embodiment, the concentration of the dye solutions, the duration of staining, the temperature of staining, or any combination of any of the foregoing, as well as the ensuing steps in the staining process, are typically higher or longer than that used for conventional H&E staining. In one embodiment the sample is overstained as compared to that typically performed in conventional H&E staining.

As noted herein, in some embodiments, one anchorable and one non-anchorable dye may be used, such as anchorable hematoxylin and eosin, or hematoxylin and anchorable eosin. Such variations are within the scope of the invention and the skilled artisan will readily adjust the conditions for dying using each.

Protein and Nucleic Acid Anchoring. In some embodiments, the anchorable dyes provide the necessary anchoring and no separate protein and nucleic acid anchoring reagents are used. In some embodiments, both anchorable dyes and protein and nucleic acid anchors are used. In some embodiments, anchorable hematoxylin and (nonanchorable) eosin along with a protein anchoring reagent are used. In some embodiments, a (nonanchorable) hematoxylin, nucleic acid anchoring reagent, and anchorable eosin are used. In some embodiments the combination of anchorable or non-anchorable dyes, and protein or nucleic anchors will be selected to provide optimal staining of the specimen.

In one embodiment, the protein cross-linking agent is used before or after the anchorable eosin is used. In one embodiment, the nucleic acid cross-linking agent is before or used after the anchorable hematoxylin is used. In one embodiment, the protein cross-linking agent is used before or after the anchorable hematoxylin, anchorable eosin, or both are used. In one embodiment, the nucleic acid cross-linking agent is used before or after the anchorable hematoxylin, anchorable eosin, or both are used. In one embodiment, the protein cross-linking agent and the nucleic cross-linking agent are used before, simultaneous, or after the anchorable or non-anchorable dyes are used in any combination and in any order. In another embodiment, the protein cross-linking agent, the nucleic acid cross-linking agent, the anchorable hematoxylin, the anchorable eosin, hematoxylin and eosin may be used in any combination and in any order.

When a protein or nucleic acid cross-linker is used, in one embodiment, the sample is incubated in 0.100-100 mg/ml, each of Protein anchoring reagent and Nucleic acid anchoring reagent. In one embodiment the protein anchoring reagent is glutaraldehyde. In one embodiment the protein anchoring reagent is 6-((acryloyl)amino)hexanoic acid succinimidyl ester ("Acryloyl-X", "AcX" or "Ac-X"; see, for example, Tillberg et al., Nat. Biotech. 34 (9): 987 [2016]). In one embodiment the nucleic acid anchoring reagent is NucliX (3-acrylamide-N-(3-((4-((2-chloroethyl)(methyl)amino)benzyl)amino)propyl)-N,N-dimethylpropan-1-ammonium 2,2,2-salt), as described in PCT/US2018/055; PCT/US2018/055254, published as WO2019/075091, incorporated herein by reference. In one embodiment the nucleic acid anchoring reagent is LabelX, as described in Chen et al., Nat. Meth 13:679 [2016]). Other examples of suitable anchoring reagents are described in PCT/US2018/055254.

Polymerization. The sample is permeated with hydrogel embedding monomer solution, such as 8.625% (w/w) sodium acrylate, 2.5% (w/w) acrylamide, 0.15% (w/w) N,N"-methylene bisacrylamide and 2 M NaCl in 1×PBS (prepared fresh weekly). Prior to embedding, the monomer solution is cooled to prevent premature gelation. Concentrated stocks of 10% (w/v) ammonium persulfate initiator and 10% (w/v) tetramethylenediamine (TEMED) accelerator are added to the monomer solution up to 0.2% (w/w) each. The sample is incubated at refrigerator temperature in the resulting solution for approximately two minutes for cultured cells or ten minutes for tissue slices, then transferred to a room temperature incubator for an hour. The aforementioned specific conditions and concentrations are merely guidelines that may be varied without deviating from the spirit of the invention. As noted above, these steps are well known in the ExM field.

Digestion and Gel Detachment. In one non-limiting example, proteinase K (New England Biolabs) is used and is prepared at 200 µg/mL in digestion buffer (50 mM Tris pH 8, 1 mM EDTA, 0.5% Triton-X100, 1M NaCl, 0.8M guanidine HCl) and applied directly to gels in at least ten times volume excess. Gels can be formed in a gelation chamber, and the gel then transferred into a well of glass bottom 6 well plate before adding digestion buffer in order to improve access of enzyme to the embedded tissue. For originally formalin-fixed, paraffin-embedded (FFPE) samples, tissue sections that were attached a glass slide, after removing the chamber the slide was cut into tissue gel composite shape and transferred into a well of glass bottom 6 well plate. The gels are then incubated in digestion buffer for between about 6 hours to overnight to ensure complete digestion of all proteins. For FFPE tissue sections, slide-attached tissue gel composite was incubated at 60 C overnight in digestion buffer, which allows the tissue gel composite to detach from the glass slide. In case it is not detached, DI water may be heated to 60 C, and added to the tissue gel composite in the well after removing the digestion buffer then incubated at 60 C for 5 min, which allows gel to detach from the glass slide.

Restaining. At this step, before expansion, any additional staining or amplification of existing staining can be performed on the specimens. Alternatively or in addition, the additional staining or amplification may be performed after expansion. Additional staining by anchorable dyes or unanchorable dyes or any combination thereof is embodied herein.

Expansion and Slide Preparation. Digested gels are next placed in excess volume of doubly de-ionized or distilled water for several hours to expanded to ensure the gel reaches equilibrium. The expanded gel is transferred into a specifically designed imaging chamber on a glass slide, water added and sealed the chamber which can be imaged on a standard optical microscope, though high light gathering and detector sensitivity are useful due to the volumetric dilution of bound dye molecules.

At this step (or prior to expansion), before sealing the gel in an imaging chamber, any additional staining or amplification of existing staining can be performed on the specimens, as noted above. The specimens may be restained using the same or different protocol as described here, or further stained with other reagents in order to identify other biomolecules in the specimen.

Imaging. Post-expansion imaging can be performed on any suitable instrument, such as but not limited to a Nikon Ti bright field optical microscope, Perkin Elmer Spinning disk confocal or a Zeiss Laser Scanning Confocal (LSM 710).

Image Analysis. The methods described here provide for traditional H&E staining to be achieved in expanded specimens following the ExM process, to enable visualization of H&E stainable histology beyond the resolution or ordinary light microscopy. For example, molecular features/morphological features of the sample such as size, shape and number of the cells and/or nucleus will be accurately described.

In any of the foregoing procedures, the sample may be further processed such as by freezing and sectioning, embedding in a resin and sectioning, shrinking using a high salt solution (e.g., 1-10 M NaCl) or any other tissue handling or processing procedure in order to obtain information about the specimen.

The examples provided below include times for processing of each step. These are merely exemplary and may be altered to suit the particular reagents, specimen and need for analysis of the specimen. For example, routine processing of specimens may be done in batch and take 1-2 days until microscopic analysis. More urgently needed results such as for biopsy specimens may be processed in hours to minutes depending on the conditions.

The examples provided below describe synthetic routes for the compounds described herein. Other compounds can be made following similar procedures. All the intermediate compounds during the synthesis of final compounds described below were purified by silica column chromatography eluting either with individual or mixture of petroleum ether and ethyl acetate. Characterization was done by LCMS and proton NMR spectroscopy. The >98% of pure final compounds II and III were obtained by additional purification with preparative MPLC. Compounds II and III were characterized by LCMS, HNMR, 13CNMR and HRMS.

EXAMPLES

Example 1. Synthesis of Anchorable Hematoxylin (Compound IIA)

N-(2-(2-(2-((3,4,9,10-tetrahydroxy-6,6a,7,11b-tetrahydroindeno[2,1-c]chromen-6a-yl)oxy)ethoxy)ethoxy)ethyl)methacrylamide (Compound IIA, AcH)

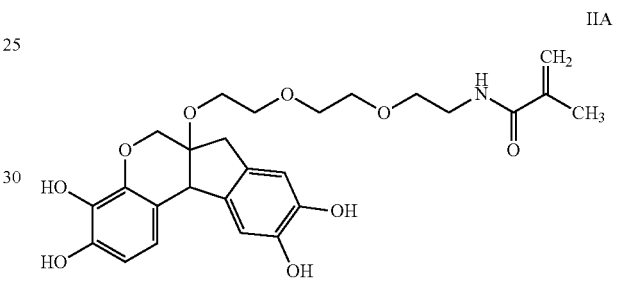

The following synthetic scheme was followed:

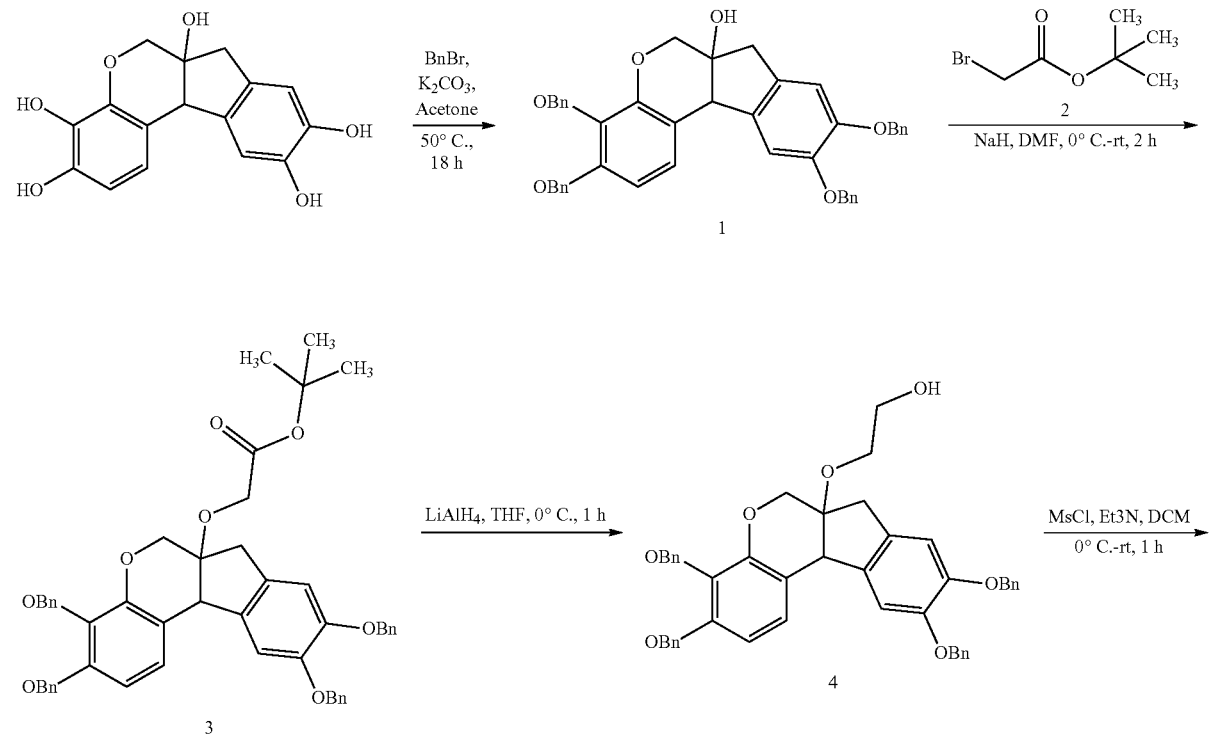

-continued
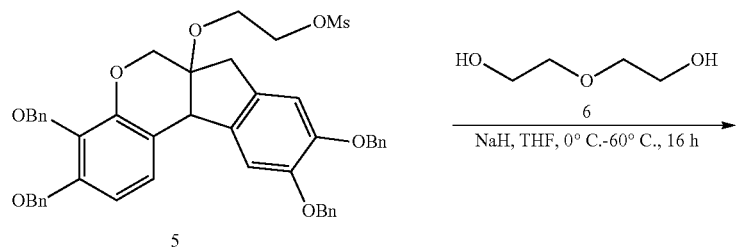
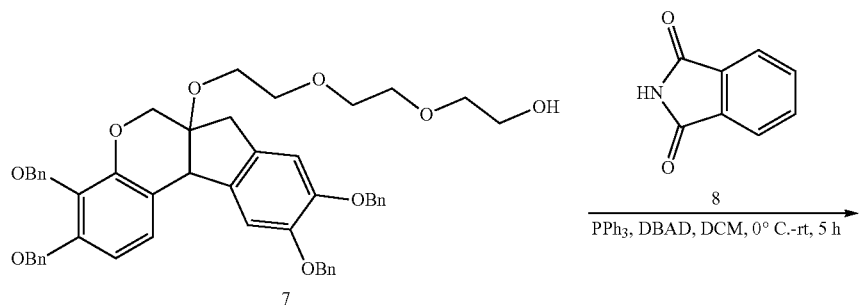
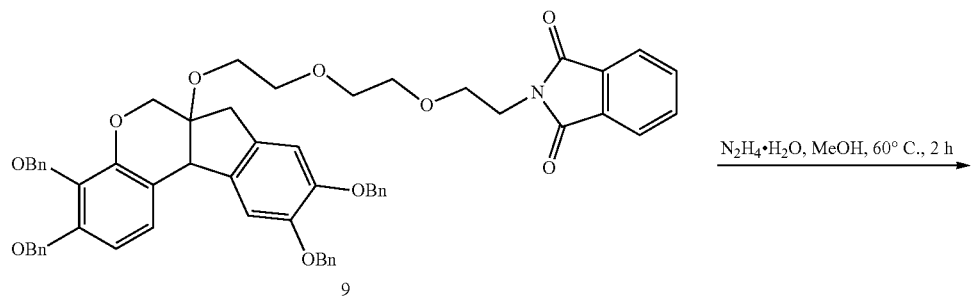
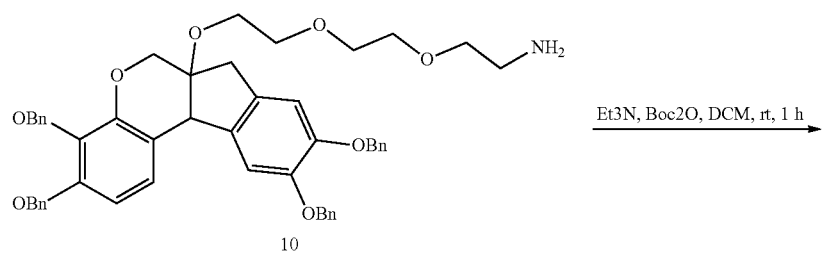
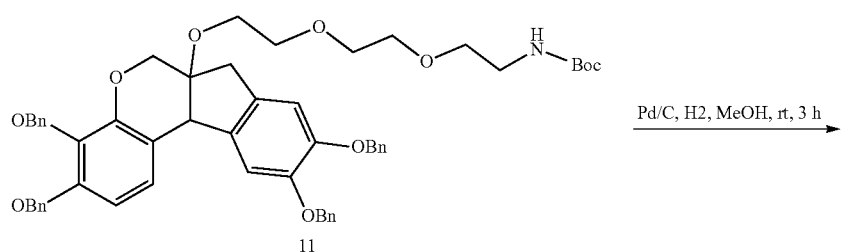
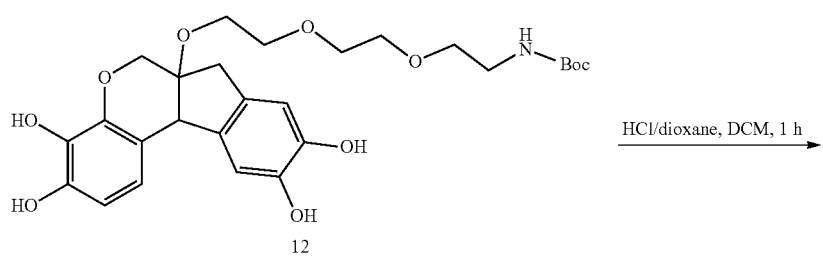

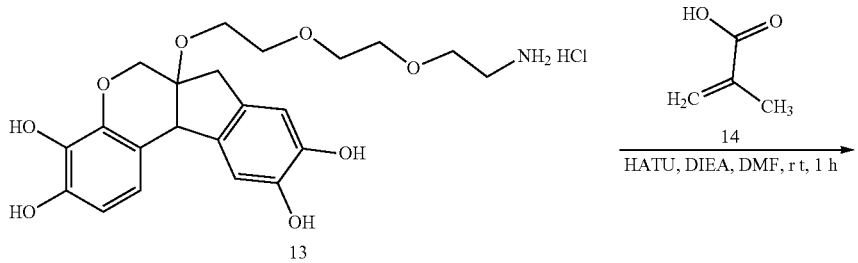

EXPERIMENTAL DETAILS

Synthesis of 3,4,9,10-tetrakis(benzyloxy)-6,6a,7,11b-tetrahydroindeno[2,1-c]chromen-6a-ol (1)

Synthesis of tert-butyl 2-((3,4,9,10-tetrakis(benzyloxy)-6,6a,7,11b-tetrahydroindeno[2,1-c]chromen-6a-yl)oxy)acetate (3)

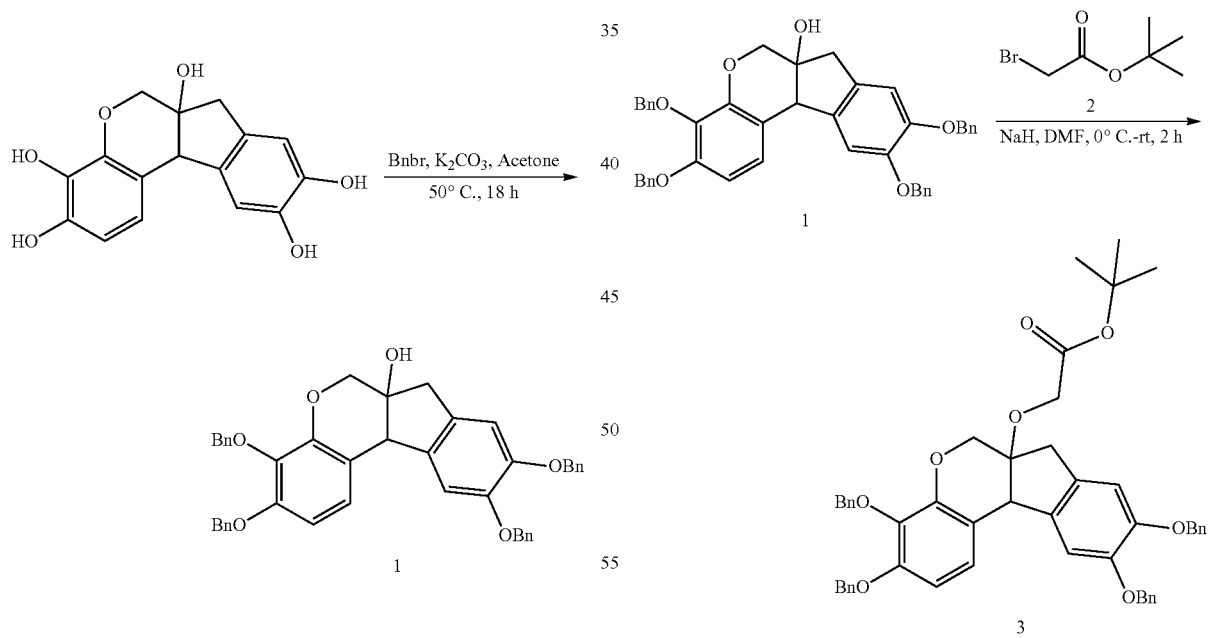

To a solution of 6,6a,7,11b-tetrahydroindeno[2,1-c]chromene-3,4,6a,9,10-pentaol (25.0 g, 82.8 mmol, 1.0 eq) in Acetone (300 mL) was added $K_2CO_3$ (68.5 g, 496.8 mmol, 6.0 eq) and BnBr (70.4 g, 414 mmol, 5.0 eq). The mixture was stirred for 18 h at 50° C. After cooled to room temperature, the mixture was concentrated in vacuum, the residue was purified by silica column chromatography eluting with PE/EA (3/1) to afford the title compound (34.0 g, 62% yield) as a white solid.

To a solution of 3,4,9,10-tetrakis(benzyloxy)-6,6a,7,11b-tetrahydroindeno[2,1-c]chromen-6a-ol (34.0 g, 51.4 mmol, 1.0 eq) in DMF (200 mL) was added NaH (3.09 g, 60% in mineral oil, 77.1 mmol, 1.5 eq) in portions at 0° C. After stirring for 0.5 h, a solution of tert-butyl 2-bromoacetate (15.0 g, 77.1 mmol, 1.5 eq) in DMF (50 mL) was added dropwise. The reaction mixture was stirred for 2 h at r.t. The reaction was quenched with saturated $NH_4Cl$ aqueous (50 mL) at 0° C. and extracted with EtOAc (100 mL×3). The combined organic layer was washed with brine (100 mL×3), dried over Na2SO4 and concentrated in vacuo. The crude product was purified by silica gel flash column chromatography eluted with Petroleum Ether/Ethyl acetate (5/1) to afford the title product (20.1 g, 50.2% yield) as a yellow solid.

Synthesis of 2-((3,4,9,10-tetrakis(benzyloxy)-6,6a,7,11b-tetrahydroindeno[2,1-c]chromen-6a-yl)oxy)ethanol (4)

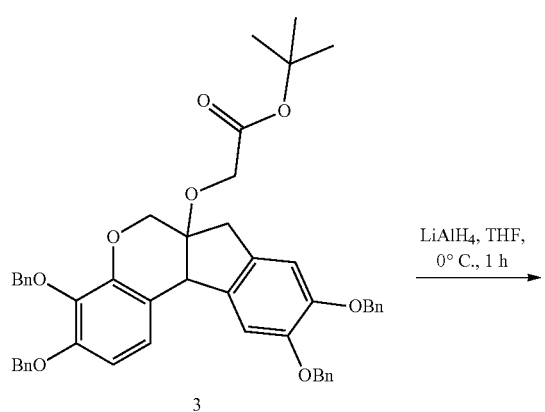

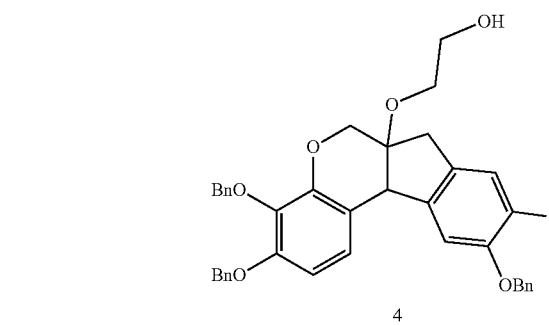

To a solution of tert-butyl 2-((3,4,9,10-tetrakis(benzyloxy)-6,6a,7,11b-tetrahydroindeno[2,1-c]chromen-6a-yl)oxy)acetate (20.1 g, 25.8 mmol, 1.0 eq) in THF (200 mL) cooled to 0° C. was added LiAlH₄ (1.47 g, 38.7 mmol, 1.5 eq) and the mixture was stirred for 1 h at 0° C. To the reaction was added Na₂SO₄·10H₂O (30 g) at 0° C. and stirred for 30 min. The mixture was filtered. The filtrate was concentrated in vacuo to give the title product (12.5 g, 68.7% yield) as a brown solid.

Synthesis of 2-((3,4,9,10-tetrakis(benzyloxy)-6,6a,7,11b-tetrahydroindeno[2,1-c]chromen-6a-yl)oxy)ethyl methanesulfonate (5)

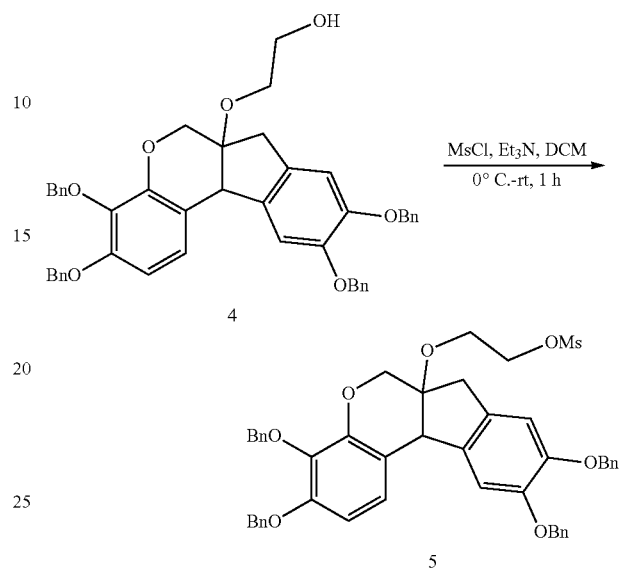

To a solution of 2-((3,4,9,10-tetrakis(benzyloxy)-6,6a,7,11b-tetrahydroindeno[2,1-c]chromen-6a-yl)oxy)ethanol (12.5 g, 17.7 mmol, 1.0 eq) and Et₃N (3.58 g, 35.4 mmol, 2.0 eq) in DCM (150 mL) was added MsCl (3.09 mg, 26.6 mmol, 1.5 eq) at 0° C. The mixture was then stirred at r.t. for 1 h. After the reaction completed, H₂O (50 mL) was added to the reaction mixture and extracted with DCM (100 mL×3). The combined organic layer was washed with brine (100 mL×3) and concentrated in vacuo to give the title product (13.0 g, 93.6% yield) as a brown solid.

Synthesis of 2-(2-(2-((3,4,9,10-tetrakis(benzyloxy)-6,6a,7,11b-tetrahydroindeno[2,1-c]chromen-6a-yl)oxy)ethoxy)ethoxy)ethanol (7)

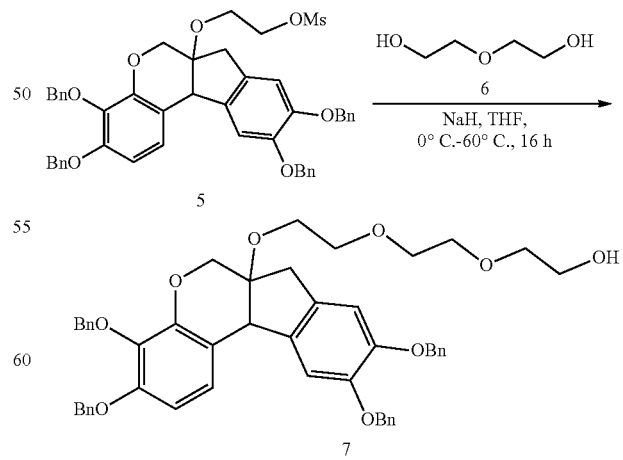

To a solution of 2,2'-oxydiethanol (15.0 g, 514 mmol, 10.0 eq) in THF (200 mL) wad added NaH (3.09 g, 60% in mineral oil, 77.1 mmol, 1.5 eq) in portions at 0° C. After stirring for 0.5 h, a solution of 2-((3,4,9,10-tetrakis(benzyloxy)-6,6a,7,11b-tetrahydroindeno[2,1-c]chromen-6a-yl)oxy)ethyl methanesulfonate (13.0 g, 51.4 mmol, 1.0 eq) in THF (50 mL) was added dropwise. The reaction mixture was stirred for 16 h at 60° C. The reaction was quenched with saturated NH$_4$Cl aqueous (50 mL) at 0° C. and extracted with EtOAc (100 mL×3). The combined organic layer was dried over Na$_2$SO$_4$ and concentrated in vacuo. The crude product was purified by silica gel flash column chromatography eluted with PE/EtOAc (2/1) to afford the title product (7.2 g, 53.2% yield) as a white solid.

Synthesis of 2-(2-(2-(2-((3,4,9,10-tetrakis(benzyloxy)-6,6a,7,11b-tetrahydroindeno[2,1-c]chromen-6a-yl)oxy)ethoxy)ethoxy)ethyl)isoindoline-1,3-dione (9)

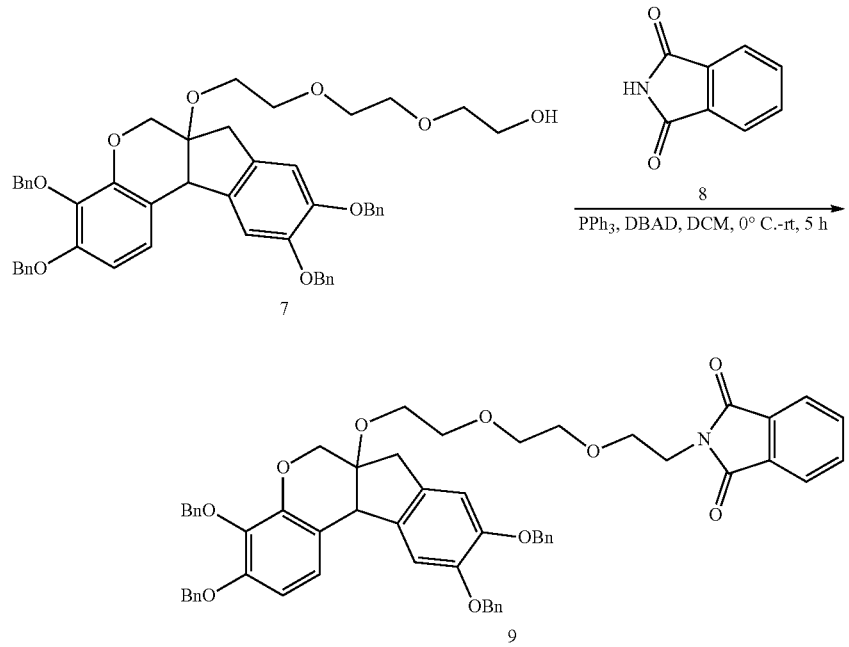

To a solution of 2-(2-(2-((3,4,9,10-tetrakis(benzyloxy)-6,6a,7,11b-tetrahydroindeno[2,1-c]chromen-6a-yl)oxy)ethoxy)ethoxy)ethanol (7.2 g, 9.07 mmol, 1.0 eq) and isoindoline-1,3-dione (1.73 g, 11.8 mmol, 1.3 eq) in dry DCM (100 mL) was added PPh$_3$ (3.1 g, 11.8 mmol, 1.3 eq), followed by DBAD (2.77 g, 11.8 mmol, 1.3 eq) at 0° C. under N$_2$. The reaction mixture was stirred for 5 h at r.t. The solvent was removed in vacuo, the residue was purified by silica gel flash column chromatography eluted with PE/EtOAc (3/1) to afford the title product (7.5 g, 90.4% yield) as a yellow solid.

Synthesis of 2-(2-(2-((3,4,9,10-tetrakis(benzyloxy)-6,6a,7,11b-tetrahydroindeno[2,1-c]chromen-6a-yl)oxy)ethoxy)ethoxy)ethanamine (10)

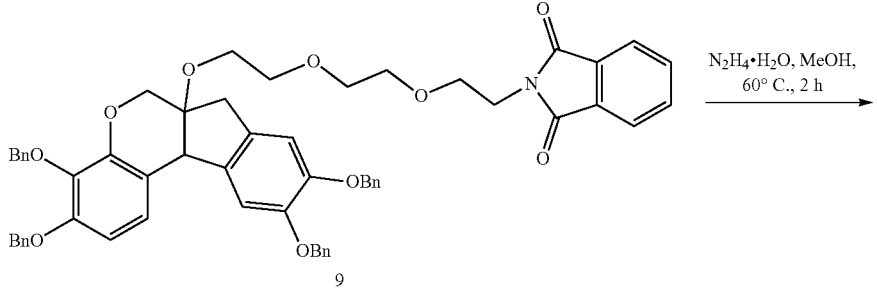

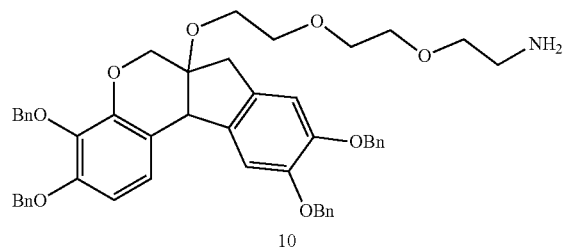

10

To a solution of 2-(2-(2-(2-((3,4,9,10-tetrakis(benzyloxy)-6,6a,7,11b-tetrahydroindeno[2,1-c]chromen-6a-yl)oxy)ethoxy)ethoxy)ethyl)isoindoline-1,3-dione (7.5 g, 8.13 mmol, 1.0 eq) in MeOH (200 mL) was added $NH_2NH_2·H_2O$ (1.02 g, 16.3 mmol, 2.0 eq). The mixture was stirred for 2 h at 60° C. The solvent was removed in vacuo, the residue was purified by silica gel flash column chromatography, eluted with DCM/MeOH (20/1) to afford the title product (4.5 g, 90.4% yield) as a yellow solid.

Synthesis of tert-butyl (2-(2-(2-((3,4,9,10-tetrakis(benzyloxy)-6,6a,7,11b-tetrahydroindeno[2,1-c]chromen-6a-yl)oxy)ethoxy)ethoxy)ethyl)carbamate (11)

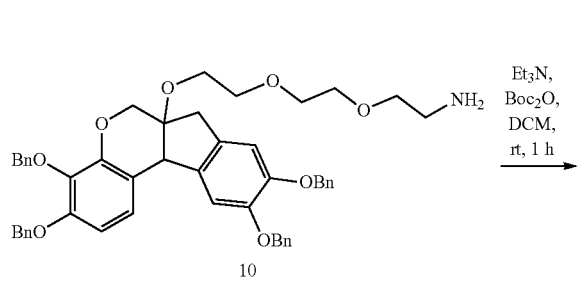

To a solution of 2-(2-(2-((3,4,9,10-tetrakis(benzyloxy)-6,6a,7,11b-tetrahydroindeno[2,1-c]chromen-6a-yl)oxy)ethoxy)ethoxy)ethanamine (4.5 g, 9.07 mmol, 1.0 eq) and $Et_3N$ (1.73 g, 11.8 mmol, 1.3 eq) in dry DCM (100 mL) was added $Boc_2O$ (3.1 g, 11.8 mmol, 1.3 eq) at 0° C. The reaction mixture was stirred for 1 h at r.t. The solvent was removed in vacuo, the residue was purified by silica gel flash column chromatography, eluted with PE/EtOAc (1/1) to afford the title product (4.0 g, 79.1% yield) as a white solid.

Synthesis of tert-butyl (2-(2-(2-((3,4,9,10-tetrahydroxy-6,6a,7,11b-tetrahydroindeno[2,1-c]chromen-6a-yl)oxy)ethoxy)ethoxy)ethyl)carbamate (12)

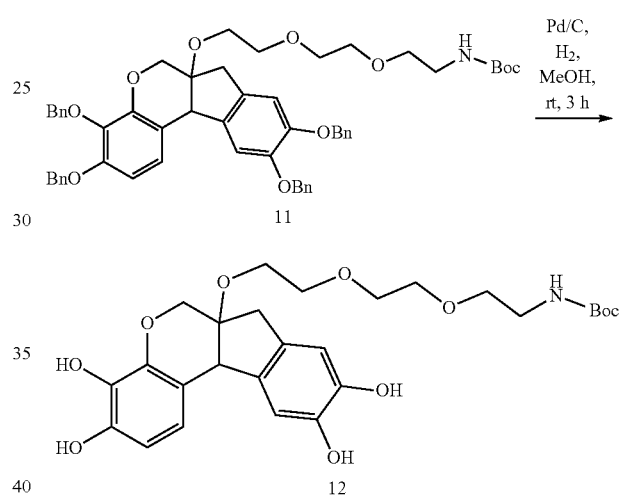

To a solution of tert-butyl (2-(2-(2-((3,4,9,10-tetrakis(benzyloxy)-6,6a,7,11b-tetrahydroindeno[2,1-c]chromen-6a-yl)oxy)ethoxy)ethoxy)ethyl)carbamate (4.0 g, 4.48 mmol, 1.0 eq) in MeOH (100 mL) was added 10% Pd/C (400 mg). The mixture was degassed with $H_2$ three times and stirred for 3 h at r.t. After filtration, the filtrate was concentrated in vacuo to give the title product (2.1 g, 88.2%) as red oil.

Synthesis of 6a-(2-(2-(2-aminoethoxy)ethoxy)ethoxy)-6,6a,7,11b-tetrahydroindeno[2,1-c]chromene-3,4,9,10-tetraol hydrochloride (13)

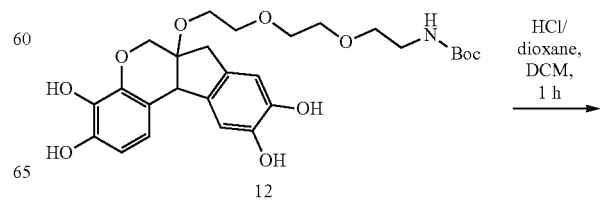

-continued

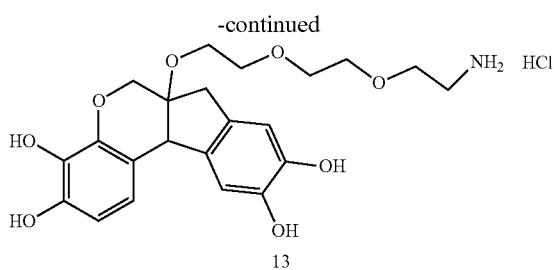

13

To a solution of tert-butyl (2-(2-(2-((3,4,9,10-tetrahydroxy-6,6a,7,11b-tetrahydroindeno[2,1-c]chromen-6a-yl)oxy)ethoxy)ethoxy)ethyl)carbamate (2.1 g, 3.94 mmol, 1.0 eq) in DCM (50 mL) was added HCl/dioxane (3.05 mL, 4 mol/L, 3.0 eq) and stirred at rt for 1 h. The mixture was concentrated to give the title product (2.1 g, 88.2%) as a red solid.

Synthesis of N-(2-(2-(2-((3,4,9,10-tetrahydroxy-6,6a,7,11b-tetrahydroindeno[2,1-c]chromen-6a-yl)oxy)ethoxy)ethoxy)ethyl)methacrylamide (Compound IIA, ACH)

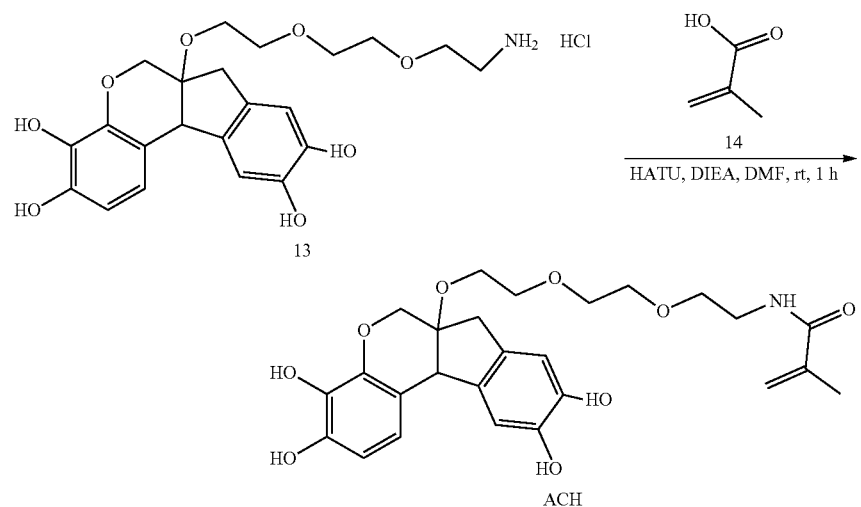

To a solution of methacrylic acid (1.16 g, 13.4 mmol, 3.0 eq) and DIEA (2.89 g, 22.4 mmol, 5.0 eq) in DMF (10 mL) was added HATU (2.04 g, 5.36 mmol, 1.2 eq). After stirred for 10 min, 6a-(2-(2-(2-aminoethoxy)ethoxy)ethoxy)-6,6a,7,11b-tetrahydroindeno[2,1-c] chromene-3,4,9,10-tetraol hydrochloride (2.1 g, 4.47 mmol, 1.0 eq) in DMF (15 mL) was added to the mixture and stirred for additional 1 h at r.t. The solution was directly purified by Prep-HPLC to afford the title product (500 mg, 3.1%) as a red solid.

$^1$H NMR (300 MHz, DMSO-d$_6$) δ 8.62 (br, 2H), 7.89 (t, J=6.0 Hz, 1H), 6.64 (d, J=8.4 Hz, 1H), 6.62 (d, J=1.5 Hz, 1H), 6.57 (s, 1H), 6.44 (d, J=8.1 Hz, 1H), 5.64 (t, J=1.2 Hz, 1H), 5.32-5.30 (m, 1H), 4.28 (d, J=12.0 Hz, 1H), 4.02 (s, 1H), 3.70-3.63 (m, 1H), 3.59-3.54 (m, 1H), 3.53-3.38 (m, 9H), 3.28-3.20 (m, 3H), 3.04 (d, J=15.6 Hz, 1H), 2.72 (d, J=15.6 Hz, 1H), 1.83 (t, J=1.2 Hz, 3H).

Following a similar route, compounds IIB and IIC were made using acryloyl-X, aminoacrylate or thioacrylate.

Example 2. Synthesis of Anchorable Hematoxylin (Compound IID)

The following reaction scheme is followed:

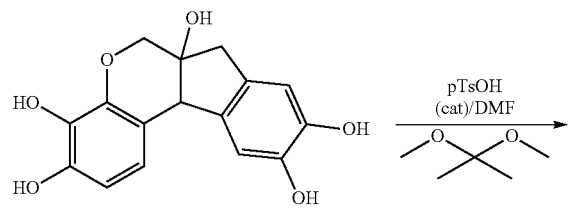

-continued

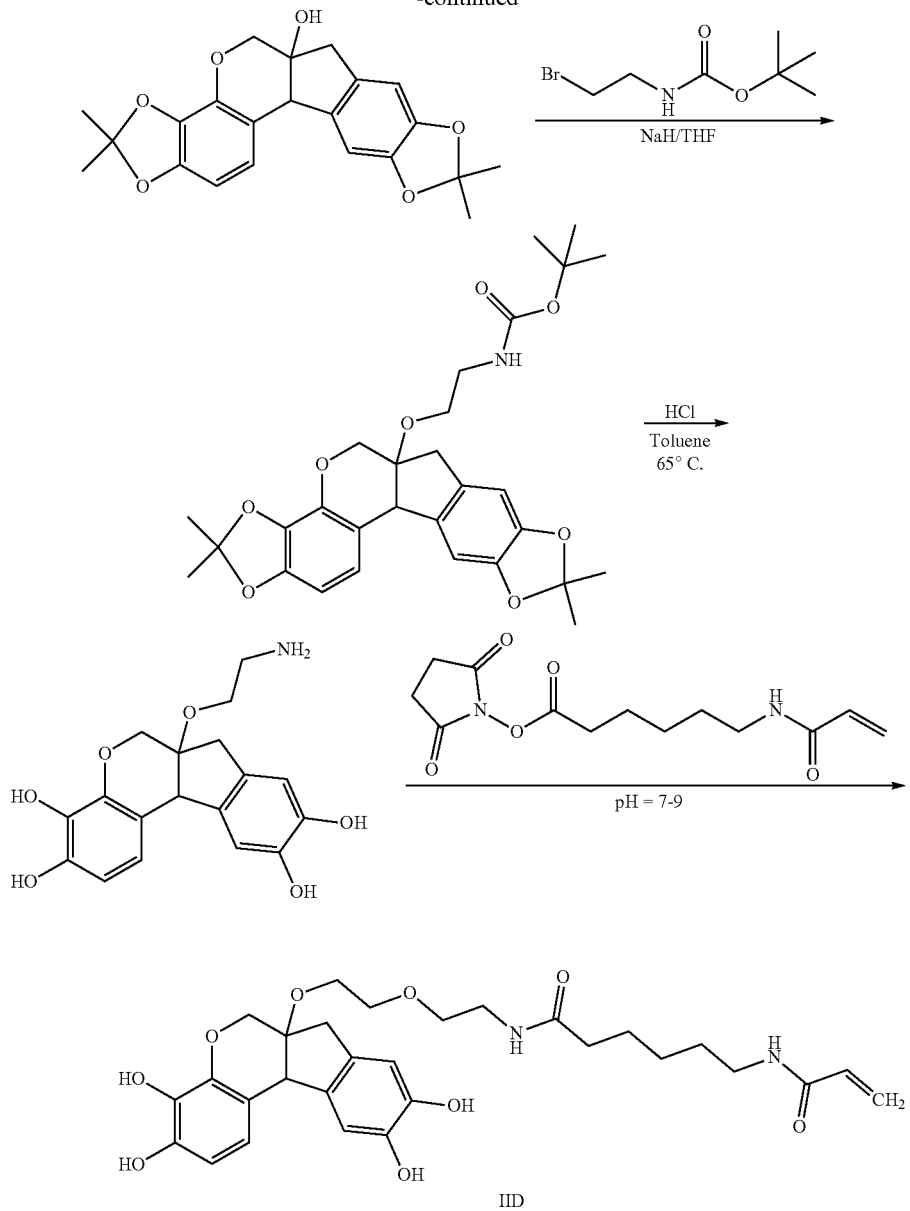

Experimental procedure. Phenolic hydroxy groups of hematoxylin are protected as acetonide group using dimethoxypropane and catalytic amount of para toluenesulphonic acid in DMF solvent. Protected hematoxylin will be coupled with BOC protected amine group using sodium hydride in THF solvent. Then protecting groups will be removed in mild acidic conditions to obtain aminated hematoxylin which will be further reacted with 6-((acryloyl) amino) hexanoic acid succinimidyl ester (AcX) to yield the final anchorable hematoxylin AcH molecule.

Example 3. Synthesis of Anchorable Hematoxylin (Compound IIE)

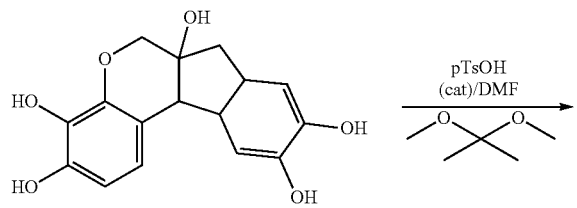

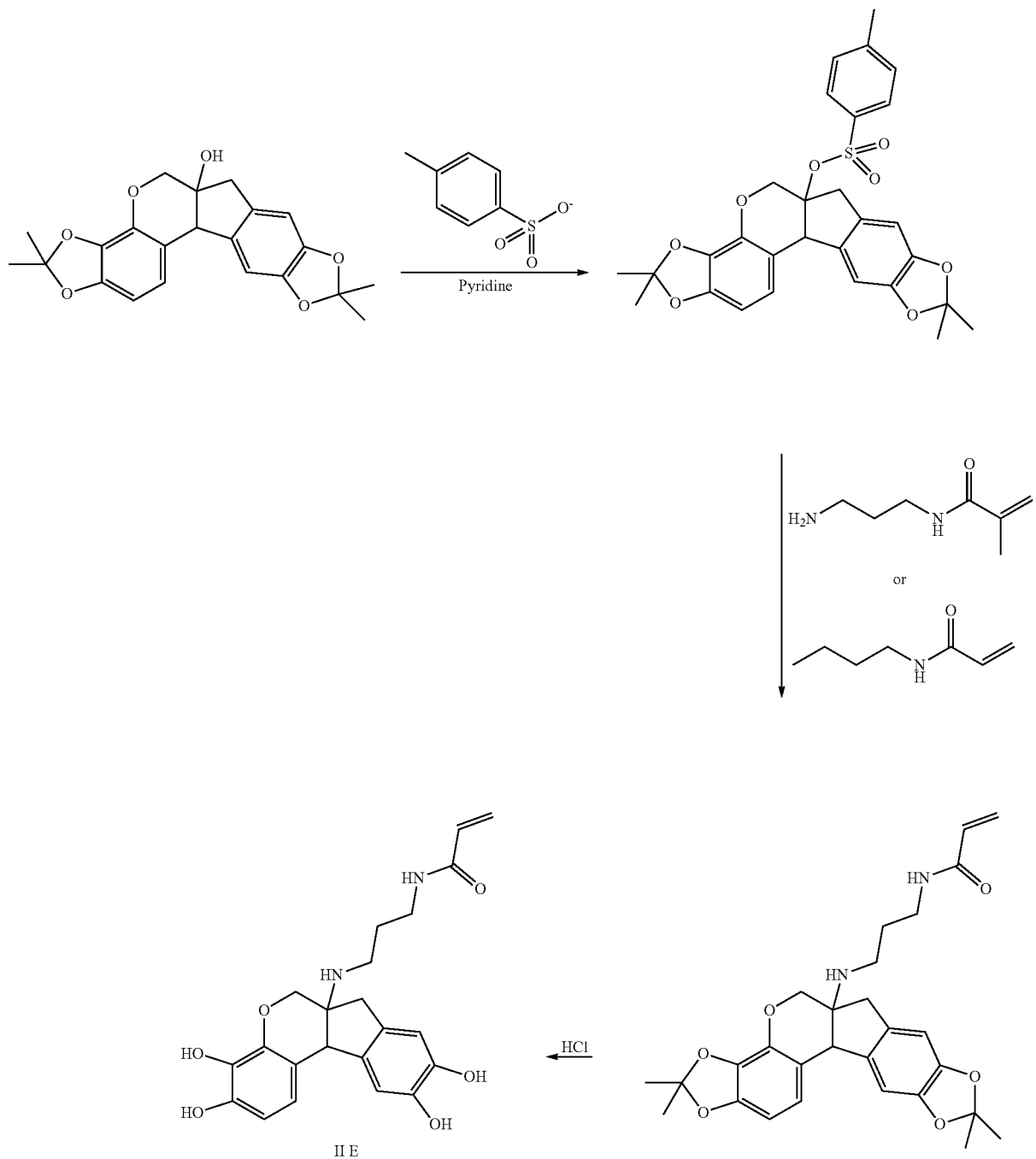

Experimental procedure. Phenolic hydroxy groups of hematoxylin are protected as acetonide group using dimethoxypropane and catalytic amount of para toluenesulphonic acid (PTSA) in DMF solvent. Protected hematoxylin will be tosylated using PTSA in pyridine. Then resulting tosylated hematoxylin will be reacted with either acrylated amine or acrylated thiol to produce anchorable hematoxylin with acetonide protected hydroxyls which is further deprotected in mild acidic conditions to obtain the final compound.

In a similar fashion, the hematein analogue of derivatizable hematoxylin may be used for the synthesis of the anchorable hemateins corresponding to the examples above. In another embodiment, the anchorable hematoxylins described above oxidize (ripens to the anchorable hematein analogue).

Example 4. Synthesis of Anchorable Eosin (isomers, Compound IIIA and IVA): 5-(2-(2-(2-methacrylamidoethoxy)ethoxy)ethoxy)-2-(2,4,5,7-tetrabromo-6-hydroxy-3-oxo-3H-xanthen-9-yl)benzoic acid
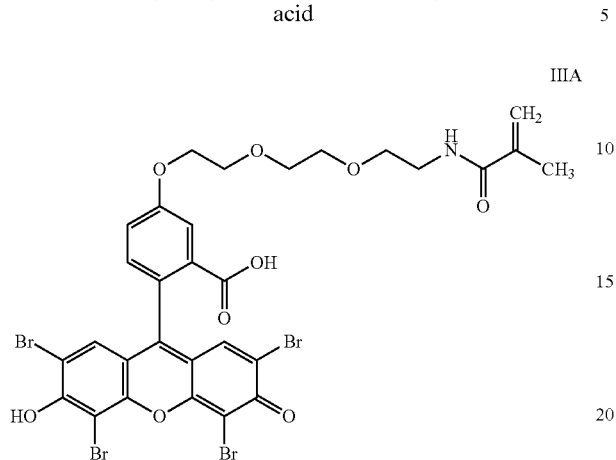
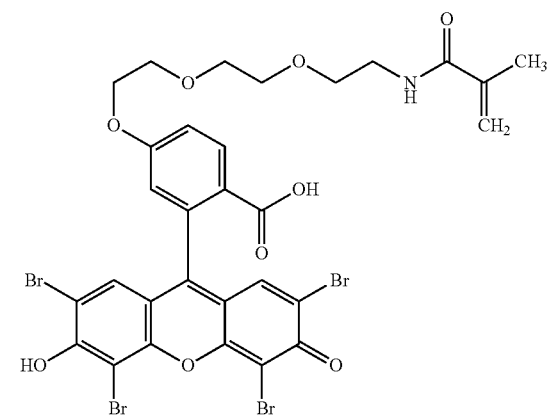
The following scheme was followed:
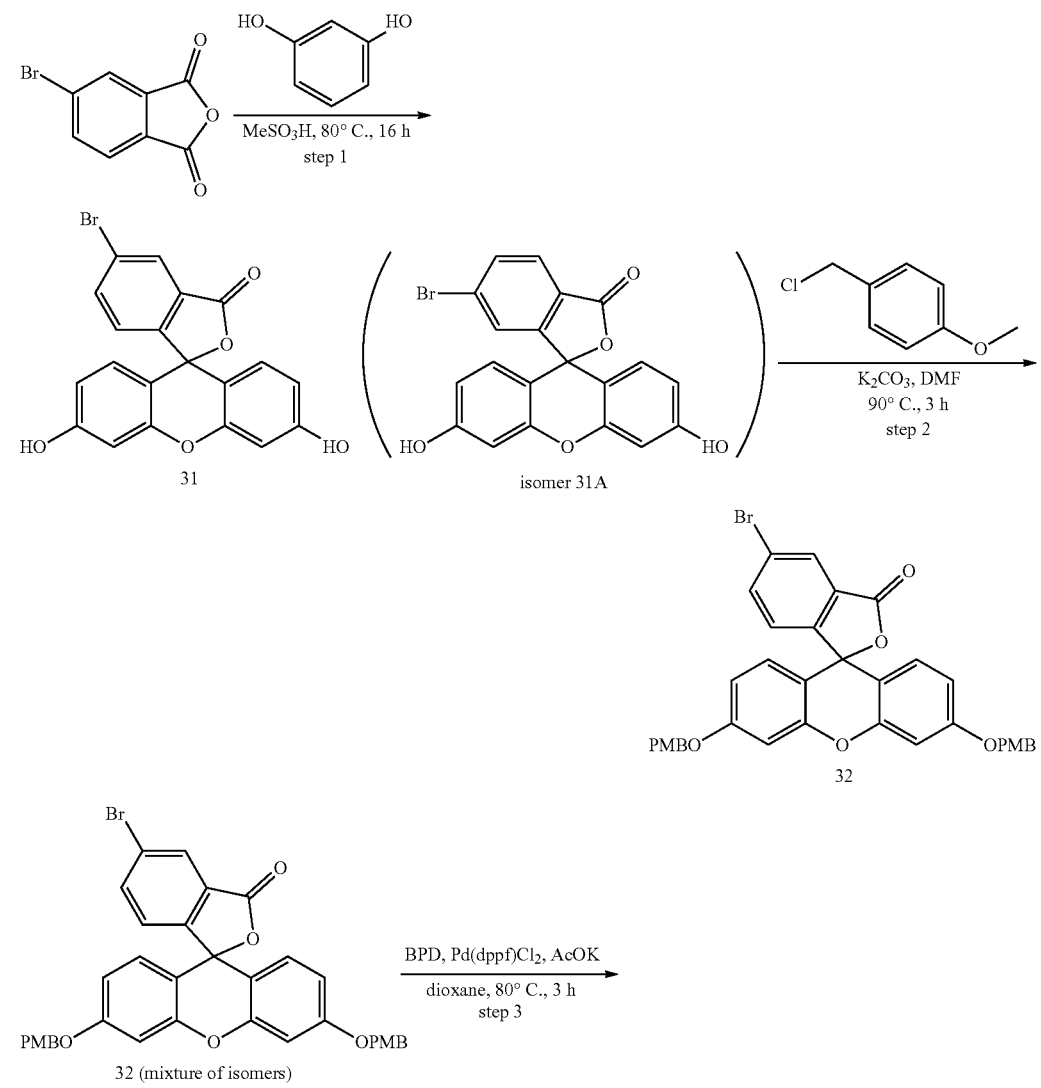

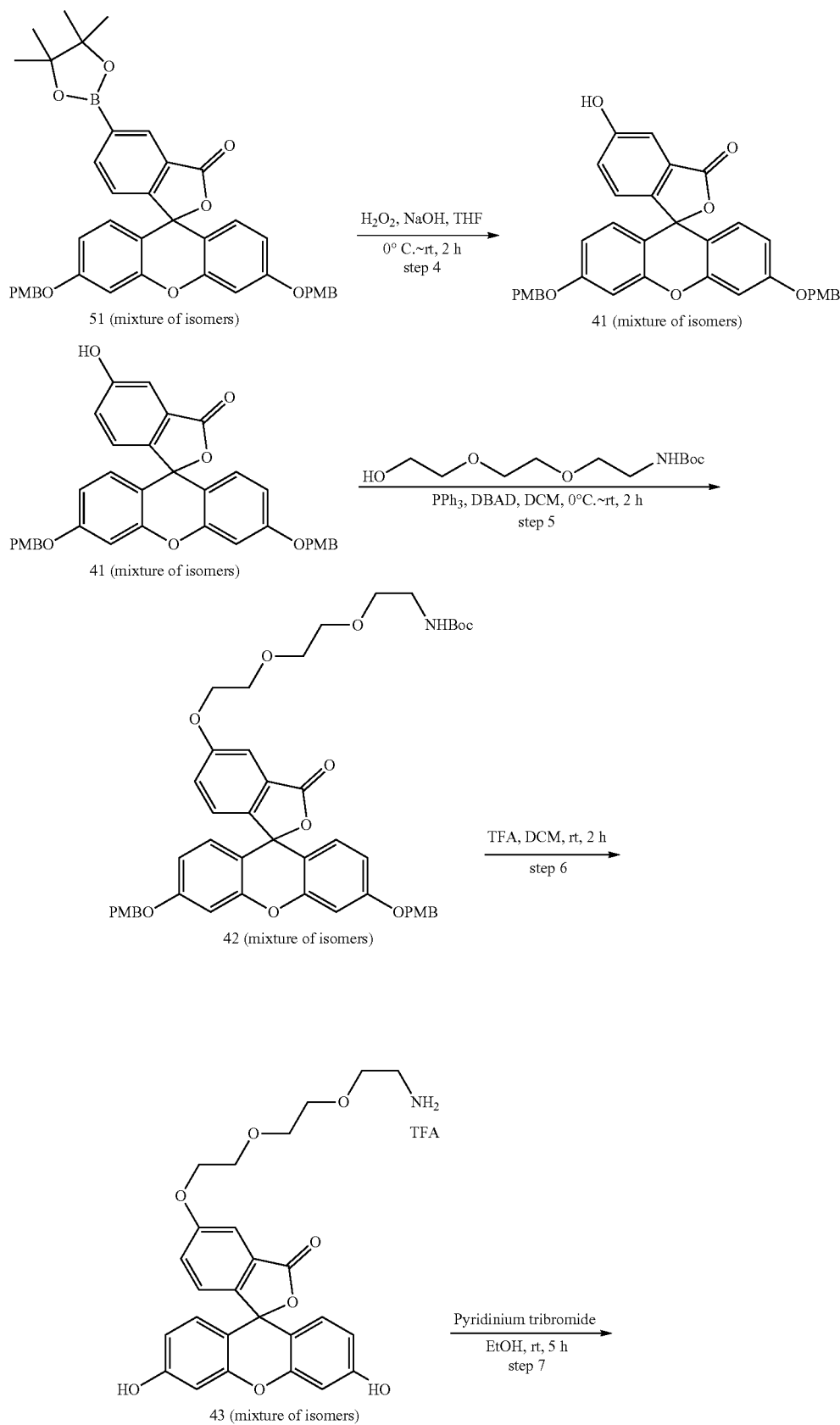

-continued
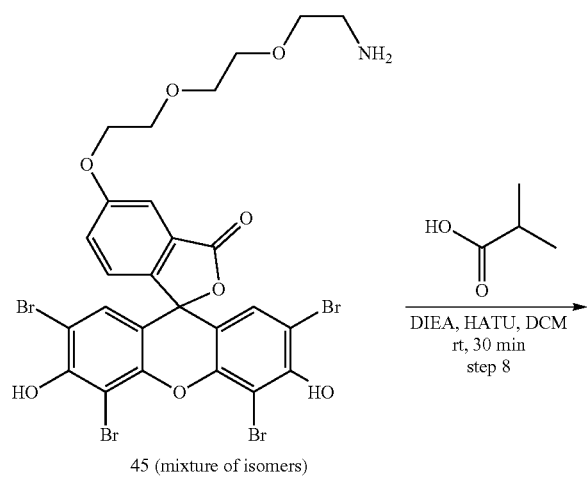
45 (mixture of isomers)
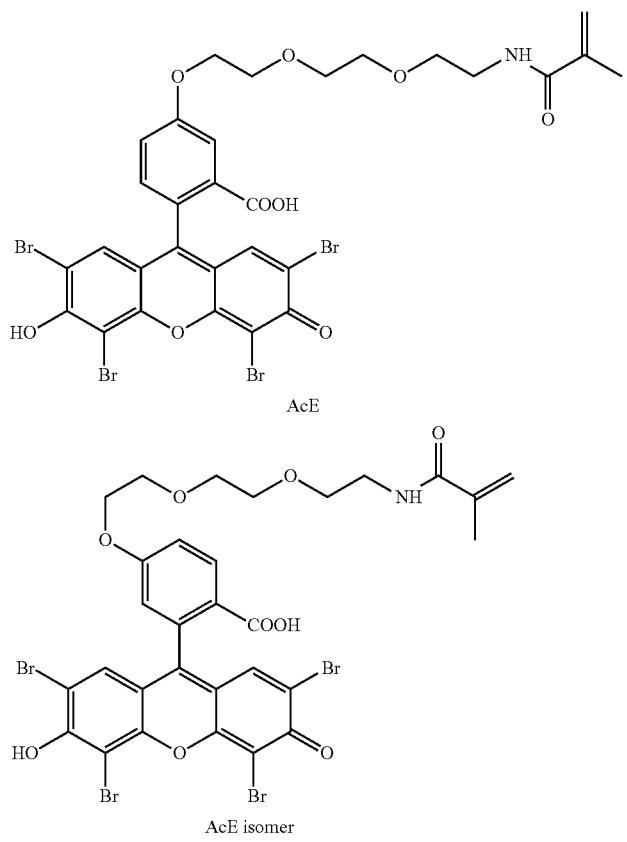
AcE
AcE isomer

EXPERIMENTAL DETAILS

Synthesis of Mixture of 5-bromo-3',6'-dihydroxy-3H-spiro[isobenzofuran-1,9'-xanthen]-3-one and 6-bromo-3',6'-dihydroxy-3H-spiro[isobenzofuran-1,9'-xanthen]-3-one (31; Mixture of Target Molecule [TM] and Isomer)

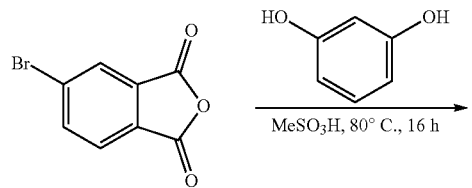

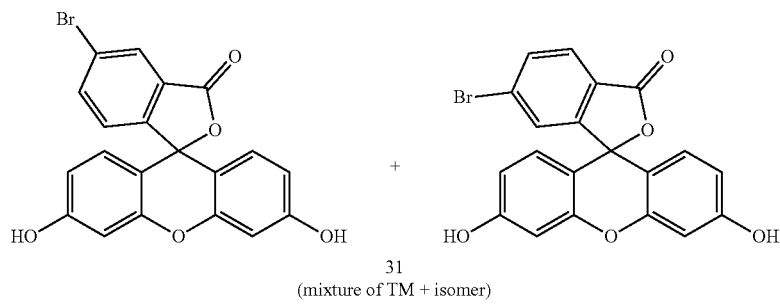

31
(mixture of TM + isomer)

To a solution of 5-bromoisobenzofuran-1,3-dione (45.0 g, 0.20 mol, 1.0 eq) in MeSO₃H (270 mL) was added resorcinol (16.0 g, 0.42 mol, 2.1 eq). The mixture was stirred for 16 h at 80° C. The reaction was cooled to room temperature and poured into a mixture of iced water (1.5 L). The crude product was precipitated. The product was collected by filtration, washed with water (300 mL), drying under vacuum to give 59 g (72.4% yield) of the title mixture as an orange solid.

Synthesis of Mixture of 5-bromo-3',6'-bis((4-methoxybenzyl)oxy)-3H-spiro[isobenzofuran-1,9'-xanthen]-3-one and 6-bromo-3',6'-bis((4-methoxybenzyl)oxy)-3H-spiro[isobenzofuran-1,9'-xanthen]-3-one (32)

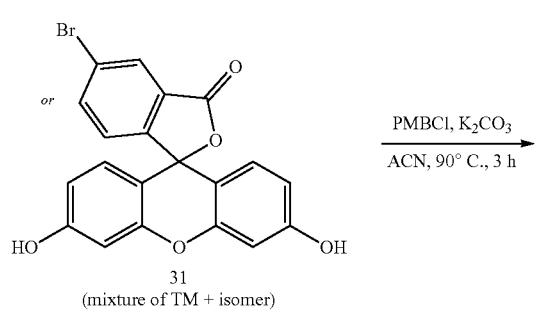

31
(mixture of TM + isomer)

PMBCl, K₂CO₃
ACN, 90° C., 3 h

-continued

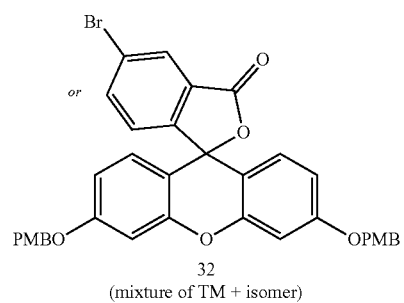

32
(mixture of TM + isomer)

To a solution of 5-bromo-3',6'-dihydroxy-3H-spiro[isobenzofuran-1,9'-xanthen]-3-one and 6-bromo-3',6'-dihydroxy-3H-spiro[isobenzofuran-1,9'-xanthen]-3-one (60 g, 0.15 mol, 1.0 eq) in ACN (600 mL) was added K₂CO₃ (62 g, 0.45 mol, 3.0 eq) and PMBCl (59 g, 0.38 mol, 2.5 eq). The mixture was stirred at 90° C. for 3 h. After cooled to room temperature, the mixture was concentrated in vacuum. The residue was purified by silica column chromatography eluting with PE/EA (1/5) afford 69.6 g (73.3% yield) of the title mixture as yellow oil.

Synthesis of Mixture of 3',6'-bis((4-methoxybenzyl)oxy)-5-(4,4,5,5-tetramethyl-1,3,2-dioxaborolan-2-yl)-3H-spiro[isobenzofuran-1,9'-xanthen]-3-one and 3',6'-bis((4-methoxybenzyl)oxy)-6-(4,4,5,5-tetramethyl-1,3,2-dioxaborolan-2-yl)-3H-spiro[isobenzofuran-1,9'-xanthen]-3-one (51)

Synthesis of Mixture of 5-hydroxy-3',6'-bis((4-methoxybenzyl)oxy)-3H-spiro[isobenzofuran-1,9'-xanthen]-3-one 6-hydroxy-3',6'-bis((4-methoxybenzyl)oxy)-3H-spiro[isobenzofuran-1,9'-xanthen]-3-one (41)

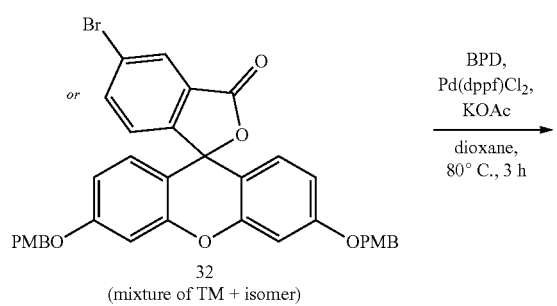

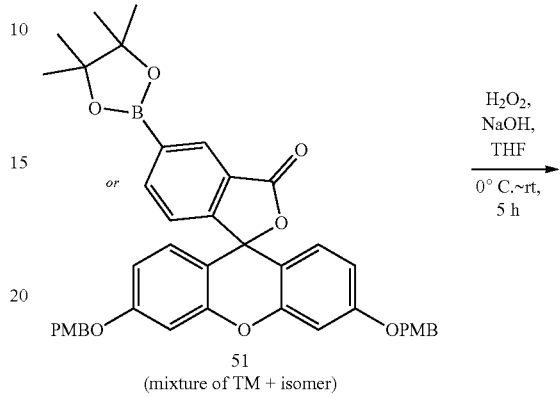

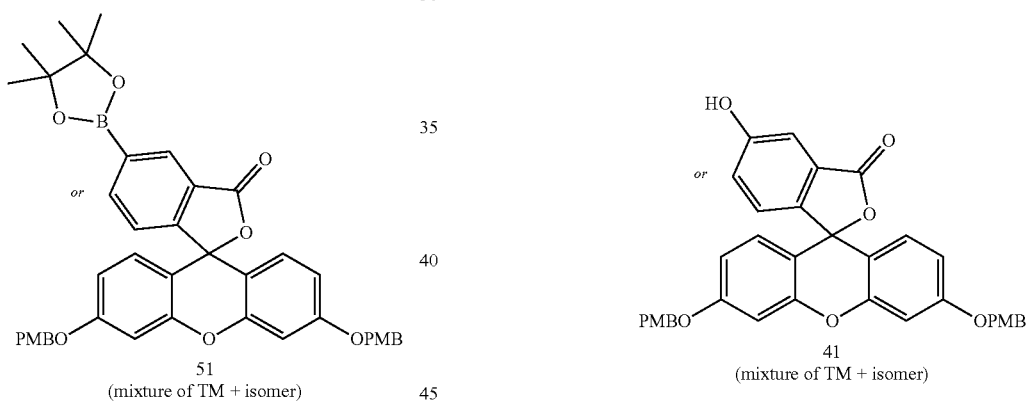

To a solution of 5-bromo-3',6'-bis((4-methoxybenzyl)oxy)-3H-spiro[isobenzofuran-1,9'-xanthen]-3-one and 6-bromo-3',6'-bis((4-methoxybenzyl)oxy)-3H-spiro[isobenzofuran-1,9'-xanthen]-3-one (69.0 g, 0.12 mol, 1.0 eq) in dioxane (1.4 L) was added BPD (61.0 g, 0.24 mol, 2.0 eq), KOAc (35.0 g, 0.36 mol, 3.0 eq) and Pd(dppf)Cl$_2$ (4.4 g, 0.006 mol, 0.05 eq). The flask was evacuated and flushed three times with nitrogen and then stirred at 80° C. for 3 h under N$_2$. After cooled to room temperature, the mixture was concentrated in vacuum, the residue was purified by silica column chromatography eluting with PE/EA (1/1) afford the title compound 39.7 g (57.5% yield) as yellow oil.

To a solution of 3',6'-bis((4-methoxybenzyl)oxy)-5-(4,4,5,5-tetramethyl-1,3,2-dioxaborolan-2-yl)-3H-spiro[isobenzofuran-1,9'-xanthen]-3-one and 3',6'-bis((4-methoxybenzyl)oxy)-6-(4,4,5,5-tetramethyl-1,3,2-dioxaborolan-2-yl)-3H-spiro[isobenzofuran-1,9'-xanthen]-3-one (39.7 g, 57 mmol, 1.0 eq) in THF/H$_2$O (900 ml/300 ml) was added 1 M NaOH (114 mL, 0.29 mol, 5.00 eq) dropwise at 0° C. followed by solution of H$_2$O$_2$ (55.9 ml, 0.57 mol, 10.0 eq) dropwise. The mixture was stirred for 5 h at room temperature. Then pH value was adjusted to 7.0 with 2M HCl aqueous, extracted with EtOAc (3×300 mL). The combined organic layers were dried over anhydrous Na$_2$SO$_4$ and concentrated under reduced pressure. The residue was purified by silica column chromatography eluting with EA to afford the title mixture (7.63 g, 19.2% yield) as yellow oil.

Synthesis of tert-butyl (2-(2-(2-hydroxyethoxy)ethoxy)ethyl)carbamate

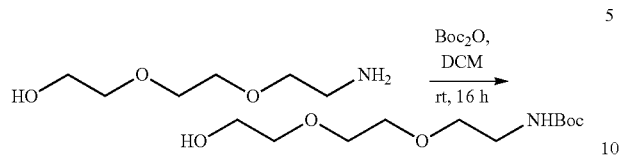

To a solution of 2-(2-(2-aminoethoxy) ethoxy) ethanol (10.0 g, 67 mmol, 1.0 eq) in DCM (150 mL) was added Boc₂O (17.4 g, 80 mmol, 1.2 eq). The mixture was stirred at room temperature for 16 h. The mixture was concentrated in vacuum, the residue was purified by silica column chromatography eluting with PE/EA (2/1) to afford the title compound (11.3 g, 67.7% yield) as colorless oil.

Synthesis of Mixture of tert-butyl (2-(2-(2-((3',6'-bis((4-methoxybenzyl)oxy)-3-oxo-3H-spiro[isobenzofuran-1,9'-xanthen]-5-yl)oxy)ethoxy)ethoxy)ethyl)carbamate and tert-butyl (2-(2-(2-((3',6'-bis((4-methoxybenzyl)oxy)-3-oxo-3H-spiro[isobenzofuran-1,9'-xanthen]-6-yl)oxy)ethoxy)ethoxy)ethyl)carbamate (42)

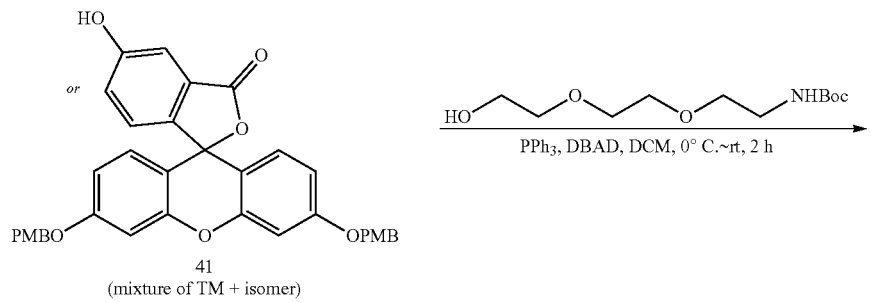

41
(mixture of TM + isomer)

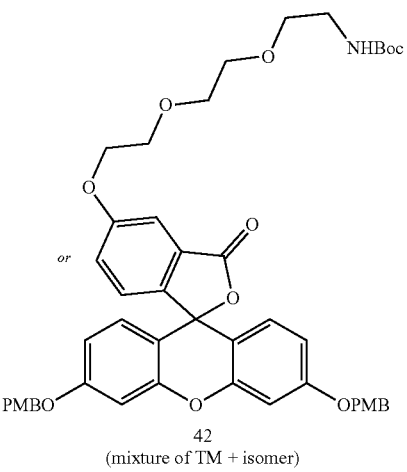

42
(mixture of TM + isomer)

To a solution of 5-hydroxy-3',6'-bis((4-methoxybenzyl)oxy)-3H-spiro[isobenzofuran-1,9'-xanthen]-3-one and 6-hydroxy-3',6'-bis((4-methoxybenzyl)oxy)-3H-spiro[isobenzofuran-1,9'-xanthen]-3-one (8.63 g, 13 mmol, 1.0 eq) in DCM (150 mL) was added tert-butyl (2-(2-(2-hydroxyethoxy)ethoxy)ethyl)carbamate (4.9 g, 19.5 mmol, 1.5 eq) and PPh₃ (5.1 g, 19.5 mmol, 1.5 eq) at 0° C. Then a solution of DBAD (4.9 g, 19.5 mmol, 1.5 eq) in DCM (10 ml) was added dropwise. The mixture was stirred for 2 h at room temperature. The mixture was concentrated in vacuum. The residue was purified by silica column chromatography eluting with PE/EA (1/5) to afford the title compound (3.3 g, 31% yield) as yellow brown oil.

67

Synthesis of Mixture of 5-(2-(2-(2-aminoethoxy)ethoxy)ethoxy)-3',6'-dihydroxy-3H-spiro[isobenzofuran-1,9'-xanthen]-3-one (TFA salt) and 6-(2-(2-(2-aminoethoxy)ethoxy)ethoxy)-3',6'-dihydroxy-3H-spiro[isobenzofuran-1,9'-xanthen]-3-one (TFA Salt) (43)

68

Synthesis of 5-(2-(2-(2-aminoethoxy)ethoxy)ethoxy)-2',4',5',7'-tetrabromo-3',6'-dihydroxy-3H-spiro[isobenzofuran-1,9'-xanthen]-3-one and 6-(2-(2-(2-aminoethoxy)ethoxy)ethoxy)-2',4',5',7'-tetrabromo-3',6'-dihydroxy-3H-spiro[isobenzofuran-1,9'-xanthen]-3-one (44)

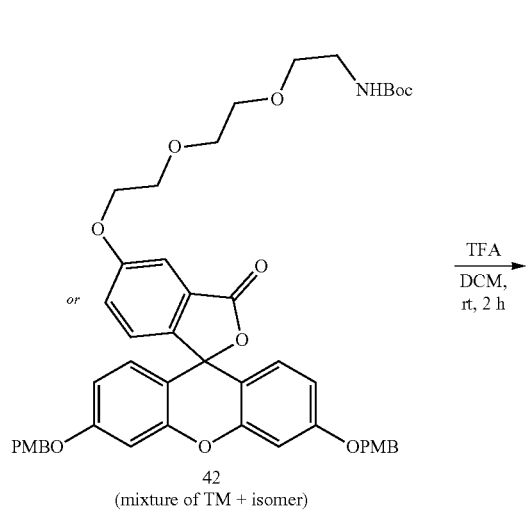

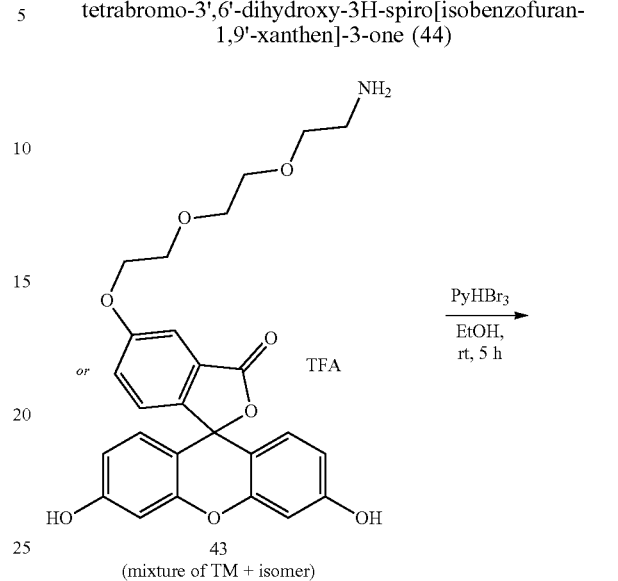

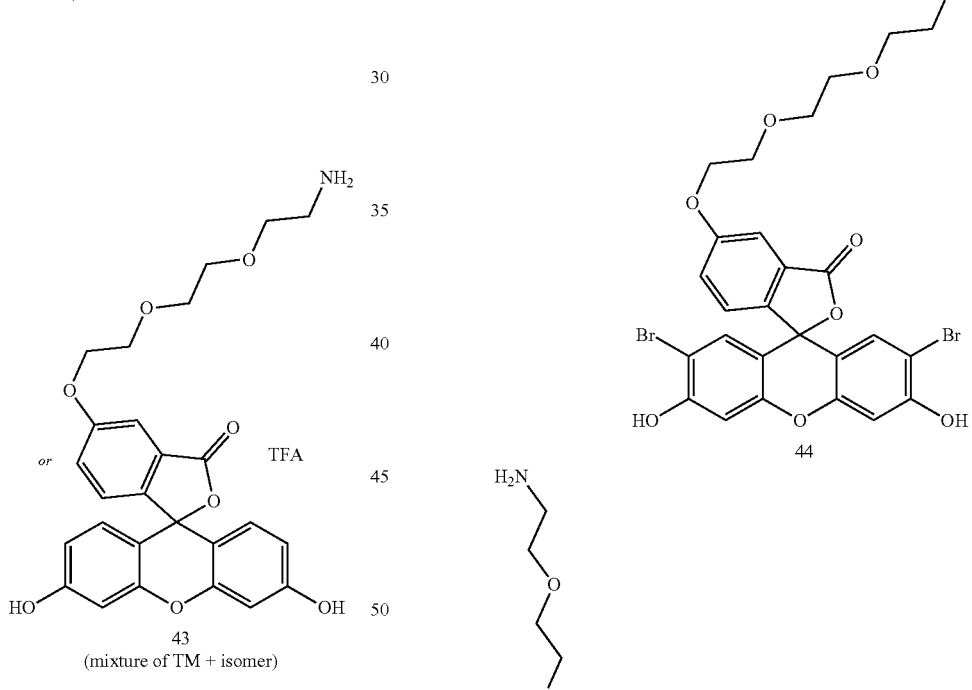

To a solution of 5-(2-(2-(2-aminoethoxy)ethoxy)ethoxy)-3',6'-dihydroxy-3H-spiro[isobenzofuran-1,9'-xanthen]-3-one and 6-(2-(2-(2-aminoethoxy)ethoxy)ethoxy)-3',6'-dihydroxy-3H-spiro[isobenzofuran-1,9'-xanthen]-3-one (3.3 g, 1.2 mol, 1.0 eq) in DCM (150 ml) was added TFA (10 mL). The mixture was stirred at room temperature for 2 h. The mixture was concentrated in vacuum to afford the title mixture (2.8 g, crude) as yellow-brown oil.

To a solution of 5-(2-(2-(2-aminoethoxy)ethoxy)ethoxy)-3',6'-dihydroxy-3H-spiro[isobenzofuran-1,9'-xanthen]-3-one (TFA salt) and 6-(2-(2-(2-aminoethoxy)ethoxy)ethoxy)-3',6'-dihydroxy-3H-spiro[isobenzofuran-1,9'-xanthen]-3-one (2.56 g, 5.3 mmol, 1.0 eq) in EtOH (40 mL) was added pyridinium bromide perbromide (8.5 g, 26.5 mmol, 5.0 eq). The mixture was stirred for 5 h at room temperature. The mixture was concentrated in vacuum. The residue was purified by prep-MPLC to afford the desired compound (2.8 g, 32%) as yellow-brown oil.

Synthesis of 5-(2-(2-(2-methacrylamidoethoxy)ethoxy) ethoxy)-2-(2,4,5,7-tetrabromo-6-hydroxy-3-oxo-3H-xanthen-9-yl) benzoic acid (IIIA [AcE] and IVA [AcE Isomer])

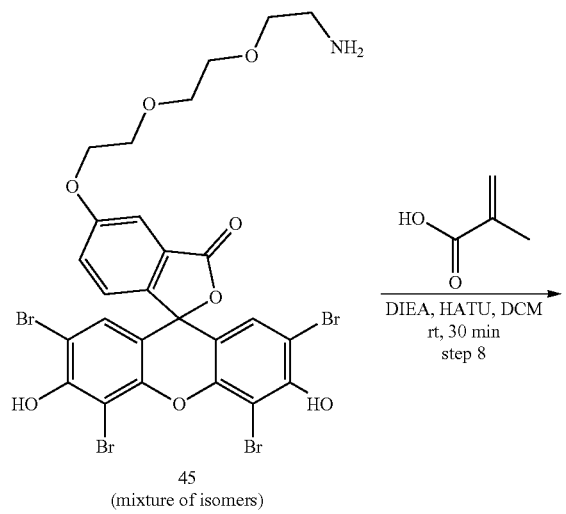

45
(mixture of isomers)

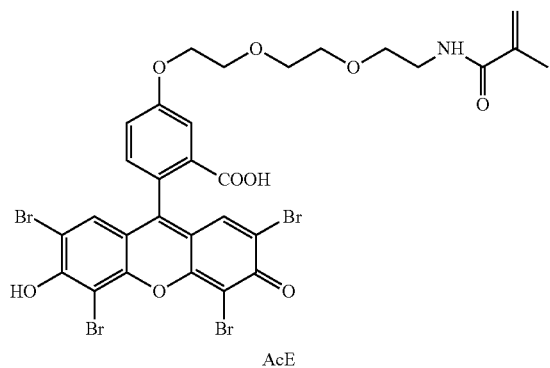

AcE

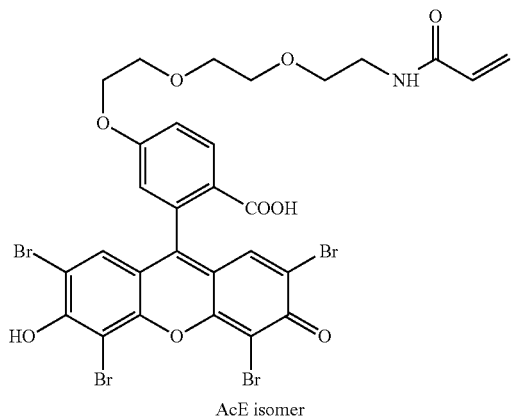

AcE isomer

Compound 45 is shown as a mixture of isomers from the preceding step. To a solution of 5-(2-(2-(2-aminoethoxy)ethoxy)ethoxy)-2',4',5',7'-tetrabromo-3',6'-dihydroxy-3H-spiro[isobenzofuran-1,9'-xanthen]-3-one (850 mg, 1.1 mmol, 1.0 eq) in DCM (20 mL) was added methacrylic acid (284 mg, 3.3 mmol, 3.0 eq), DIEA (426 mg, 3.3 mmol, 3.0 eq) and HATU (495 mg, 1.3 mmol, 1.2 eq). The mixture was stirred at room temperature for 30 min. The mixture was concentrated in vacuum. The residue was purified by silica column chromatography eluting with EtOAc to afford the title compound (504 mg, 59.2% yield) as a red solid.

HNMR (300 MHz, $CD_3OD$-d4) δ 7.80 (d, J=2.4 Hz, 1H), 7.36 (dd, J=8.4 Hz, 2.4 Hz, 1H), 7.32 (s, 2H), 7.29 (d, J=8.4 Hz, 1H), 5.73-5.72 (m, 1H), 5.39-5.36 (m, 1H), 4.36 (t, J=4.5 Hz, 2H), 3.97 (t, J=4.5 Hz, 2H), 3.81-3.77 (m, 2H), 3.73-3.68 (m, 2H), 3.64 (t, J=5.4 Hz, 2H), 3.47 (t, J=5.4 Hz, 2H), 1.95-1.94 (m, 3H).

Example 5. Separation and Purification of Anchorable Compounds and Isomers

Preparative MPLC was used to separate the two isomers described in Example 4 (IIIA and IVA) and >98% purity obtained.

All of the intermediate compounds were purified by silica column chromatography eluting either with individual or mixture of petroleum ether and ethyl acetate. Characterization is done by LCMS and proton NMR spectroscopy. In one embodiment, the compound is IIA described in Example I >98%, or is obtained by additional purification with preparative HPLC. Compounds are characterized by LCMS, HNMR, 13CNMR and HRMS.

Example 6. Synthesis of Compound IIIB

Compound IIIB can be prepared from compound IIIA by one of the following schemes in which the benzoic acid is modified to an NHS ester. Similarly, compound IVB can be prepared from compound IVA. In one embodiment, such compound generates a covalent link between proteins in the tissue and the dye.

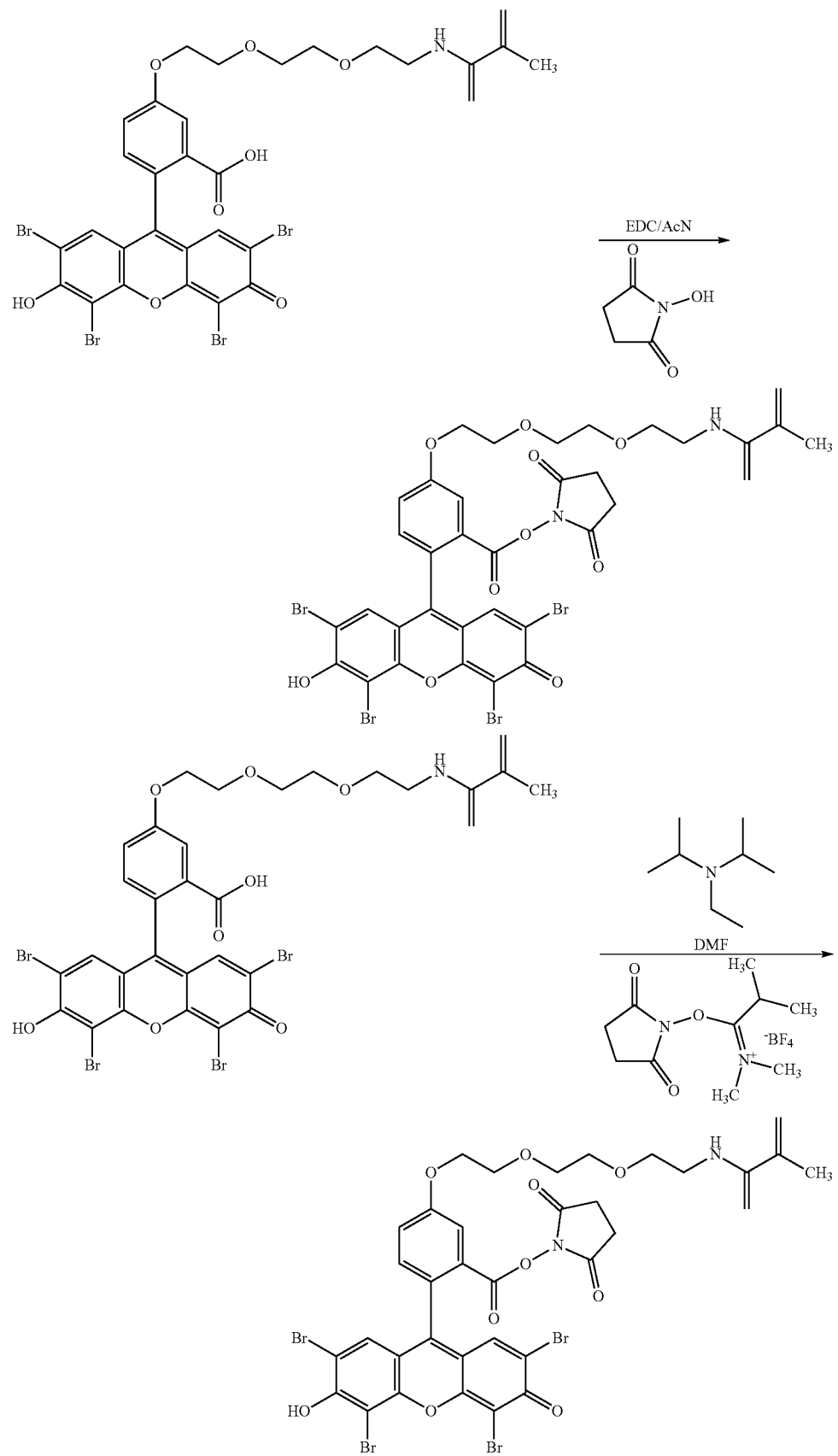

Example 7. Synthesis of Anchorable Eosin Compound IIIC

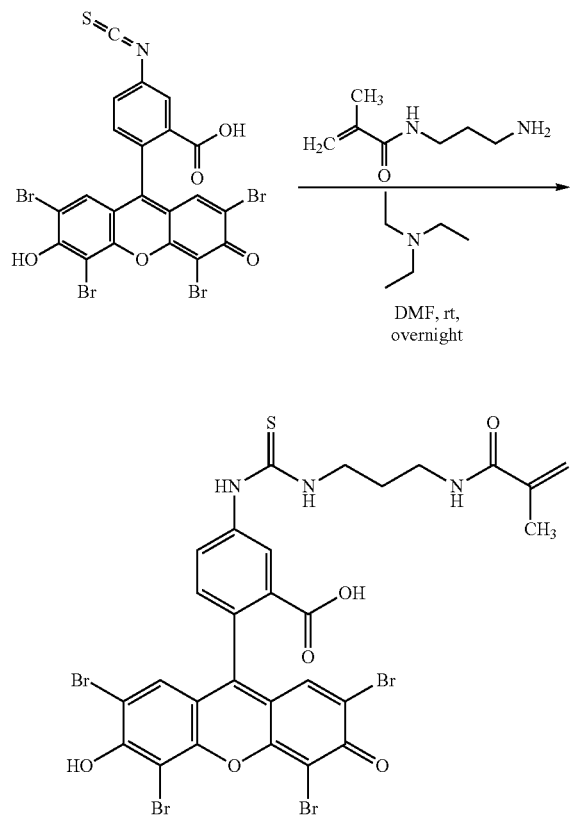

Experimental Procedure. Eosin-5-isothiocyanate (0.14 mmols), N-(3-aminopropyl) methacrylamide hydrochloride (0.17 mmols) and triethylamine (0.22 mmols) were added to a vial in 500 uL DMF and the mixture was vortexed overnight at room temperature. The reaction progress was monitored by TLC (1:9 methanol:chloroform+AcOH drop). Upon completion, the reaction mixture was poured into 150 mL DI water. A bright orange precipitate was observed. The precipitate was filtered, air dried and dried under high vacuum overnight yielding 77.4% of the product Acrylated (acryloyl) Eosin. The product was characterized by 1HNMR, 13CNMR and Mass (LCMS and Highres) spectrometry analysis.

Example 8. Anchorable H&E Based Expansion Microscopy

Figure 2:
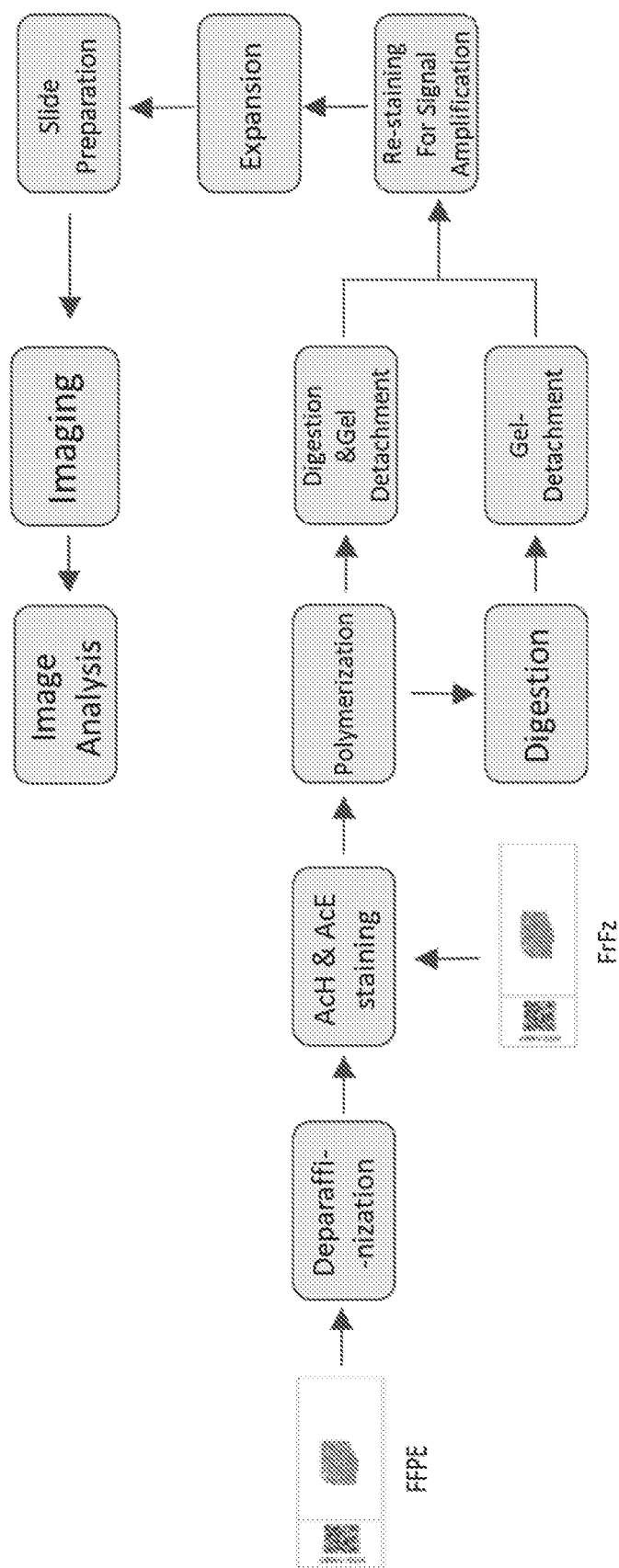
FIG. 2 is a schematic representation of a protocol for expansion microscopy utilizing derivatives of hematoxylin and eosin that can be cross-linked into the hydrogel matrix.

FIG. 1 is a flowchart depicting steps in an exemplary embodiment of the method of the invention wherein the biological sample is stained with H&E before the ExM process is carried out. FFPE refers to formalin-fixed, paraffin embedded specimens; FrFz refers to fresh frozen specimens. Anchorable hematoxylin, anchorable eosin, or both, may be used to enhance the staining of the specimen, as shown in FIG. 2.

In this example, FFPE tissue sections were used as the sample and were first deparaffinized before staining with H&E and undergoing the ExM procedure, using the following protocol. For fresh frozen tissue sections, deparaffinization is not necessary and sample processing can start from step 7.

Anchorable hematoxylin is provided as a 6.4% solution in 6% ammonium alum and 16% glycerol in 20% ethanol. Anchorable eosin is 0.05% diluted from a 0.1% stock in 0.5% glacial acetic acid in 70% ethanol. Clarifier is 1% acetic acid in 100% ethanol. Bluing solution is 0.2% ammonia water.

Deparaffinization
  Wash with 100% xylenes twice 3 min each at room temperature
  Wash with 1:1 100% xylenes: 100% ethanol 3 min at room temperature
  Wash with 100% ethanol twice 3 min each at room temperature
  Wash with 95% ethanol 3 min at room temperature
  Wash with 70% ethanol 3 min at room temperature
  Wash with 50% ethanol 3 min at room temperature
  Wash with cold-tap water 3 min at room temperature Sequential Staining
  Incubate in anchorable hematoxylin solution for 8 min at room temperature
  Wash with cold-tap water 1.5 min at room temperature
  Incubate in Clarifier solution 10 sec at room temperature
  Wash with running tap water 30 sec at room temperature
  Incubate in Bluing solution 20 sec at room temperature
  Wash with running tap water 1.5 min at room temperature
  Wash with 95% ethanol 15 sec min at room temperature
  Incubate in anchorable eosin Y solution 1-5 min at room temperature
  Wash with 95% ethanol 15 sec at room temperature
  Wash with 100% ethanol 1 min at room temperature
  Wash with 100% ethanol 1 min at room temperature
  Wash with 100% ethanol 1 min at room temperature Sequential Anchoring
  Incubate in 0.100 mg/mL Protein (AcX; 6-((acryloyl) amino) hexanoic acid succinimidyl ester) anchoring reagent in 1×PBS for 3 hours at room temperature. In some embodiments, this step may be optional.
  Incubate in 0.100 mg/mL Nucleic acid anchoring reagent (NucliX; 3-acrylamide-N-(3-((4-((2-chloroethyl)(methyl)amino)benzyl)amino)propyl)-N,N-dimethyl-propan-1-ammonium 2,2,2-salt) in 1×PBS for 3 hours at room temperature. In some embodiments, this step may be optional.
  Proceed with expansion microscopy protocol described below (polymerization, digestion, detachment, expansion, etc.).

The sample is then permeated with hydrogel embedding monomer solution. Monomer solution (1×PBS, 2M NaCl, 8.625% (w/w) sodium acrylate, 2.5% (w/w) acrylamide, 0.15% (w/w) N,N'-methylenebisacrylamide is prepared fresh every week. Prior to embedding, monomer solution is cooled to 4° C. to prevent premature gelation. Concentrated stocks (10% w/v) of ammonium persulfate (APS) initiator and tetramethylethylenediamine (TEMED) accelerator are added to the monomer solution up to 0.2% (w/w) each. Stained cells, tissue slices or any other stained samples were incubated with the monomer solution plus APS/TEMED at 4° C. for two minutes (cultured cells) or ten minutes (tissue slices), and then incubated at room temperature for one hour. Gels can be formed in a gelation chamber.

Following polymerization, the sample is subjected to digestion and expansion. Proteinase K (New England Biolabs) is diluted to 200 μg/mL in digestion buffer (50 mM Tris pH 8, 1 mM EDTA, 0.5% Triton-X100, 1M NaCl, 0.8M guanidine HCl) and applied directly to gels in at least ten times volume excess. Gels can be formed in a gelation chamber placed upon the slide over the specimen to confine the reagents to surround and include the specimen, and the chamber removed, the gel is transferred into a well in the glass bottom of a 6 well plate before adding digestion buffer in order to improve access of enzyme to the embedded tissue. (For FFPE tissue sections that are attached a glass slide, after removing the chamber slide is cut into tissue gel composite shape and is transferred into a well of glass bottom 6 well plate). The gels are incubated in digestion buffer for greater than 6 hours to overnight to ensure complete digestion of all proteins (for FFPE tissue sections, slide-attached tissue gel composite was incubated at 60 C overnight in digestion buffer, which will allow the tissue gel composite to detach from the glass slide. In case it is not detached, DI water is heated to 60 C, and is added to the tissue gel composite in the well after removing the digestion buffer then is incubated at 60 C for 5 min, which allows the gel to detach from the glass slide). Digested gels are next placed in excess volume of doubly de-ionized or distilled water for several hours to expanded to ensure the gel reaches equilibrium. The expanded gel is transferred into a specifically designed imaging chamber on glass slide, water is added water and the chamber is sealed which can be imaged on a standard optical microscope, though high light gathering and detector sensitivity are useful due to the volumetric dilution of bound dye molecules.

At this step, before sealing the gel in an imaging chamber, any additional staining or amplification of existing staining can be performed on the specimens, such as using other dyes or stains, antibody-based methods including visible or fluorescently labeled primary or secondary antibodies. Amplification of existing detection may also be performed.

Post-expansion imaging can be performed on a Nikon Ti bright field optical microscope, Perkin Elmer Spinning disk confocal or a Zeiss Laser Scanning Confocal (LSM 710). Briefly, expanded gels were transferred into a specifically designed imaging chamber on glass slide, added water and sealed the chamber before proceeding for imaging. If fluorescent or other labels were used in the process, other microscopic or detection methods may be performed then combined or overlaid with the light microscopic images to interpret the results.

Using this method employing anchorable hematoxylin and eosin derivatives combined with ExM, precise visualization of, for example, molecular features/morphological features of the sample such as size, shape and number of the cells and/or nucleus will be accurately described.

While a preferred embodiment is disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

What is claimed is:

1. An anchorable hematoxylin derivative comprising an anchorable moiety, wherein the hematoxylin is hematein or a hematein analogue.

2. An anchorable hematoxylin derivative comprising a compound of formula (II)

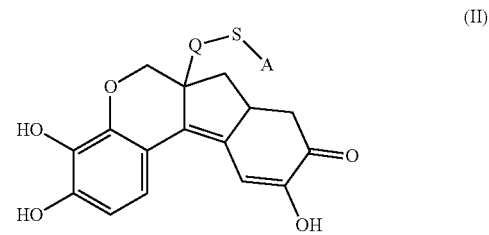

wherein Q is O or NH, S is a spacer or a bond, and A is an anchorable moiety capable of being polymerized into a hydrogel matrix.

3. The hematoxylin derivative of claim 2 wherein S is selected from

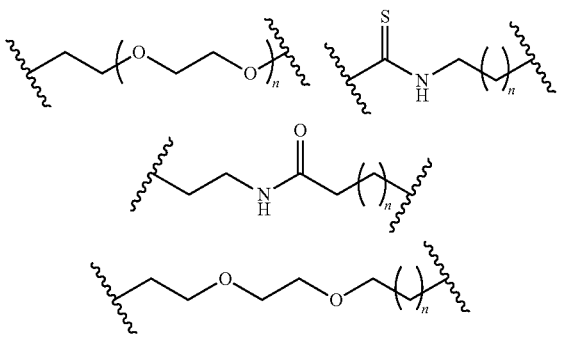

wherein n is an integer from 1 to 10.

4. The hematoxylin derivative of claim 2 wherein A is selected from a methacrylate, an acrylate, an acrylamide, a monoalkylacrylamide, a vinylalcohol, a vinylamine, an allylamine or an allylalcohol moiety.

5. The hematoxylin derivative of claim 2 wherein A is selected from:

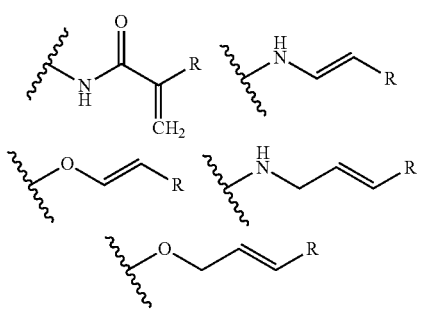

wherein R is H, alkyl, acyl, or nitrile.

6. The hematoxylin derivative of claim 5 wherein the alkyl is a $C_{1-6}$alkyl group.

7. The hematoxylin derivative of claim 5 wherein the acyl is selected from methanoyl, ethanoyl, propanoyl, isopropanoyl, butanoyl, isobutanoyl, t-butanoyl, pentanoyl, isopentanoyl, neopentanoyl or benzoyl.

8. The hematoxylin derivative of claim 2 wherein the anchorable hematoxylin has the structure IIA
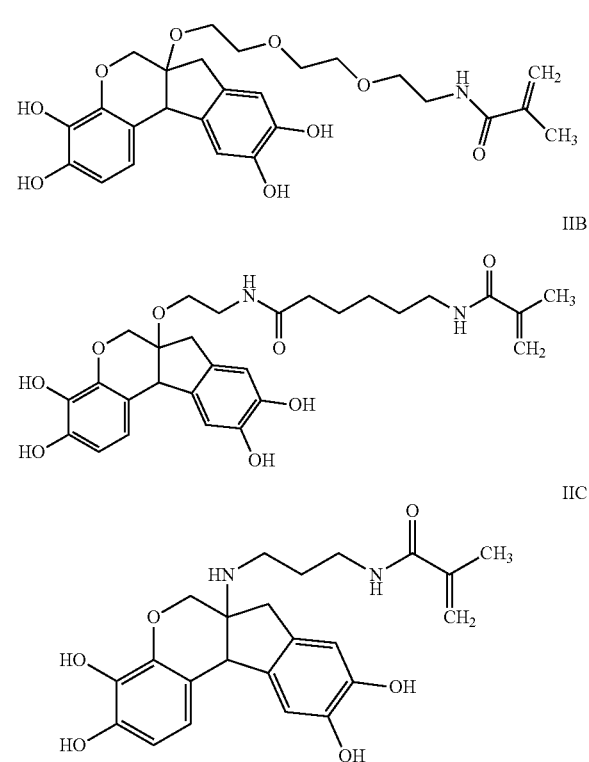
IIB

IIC

IID
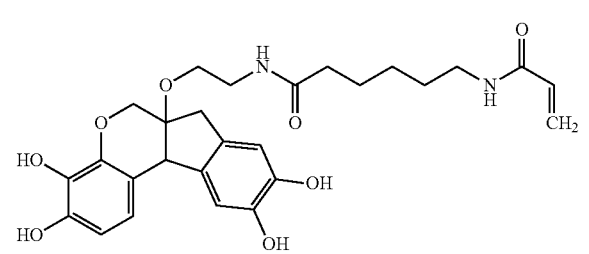
IIE

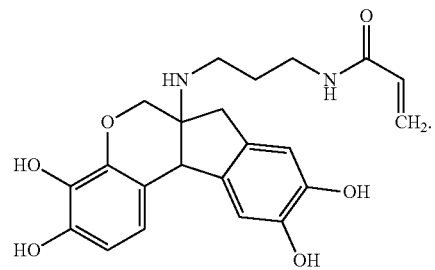

9. An anchorable eosin derivative comprising a compound of formula (III) or (IV)

III
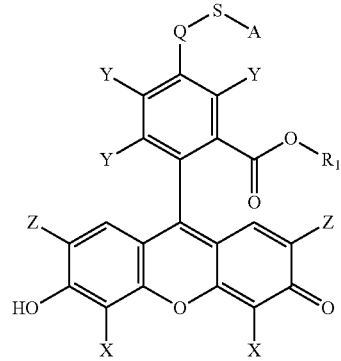

IV
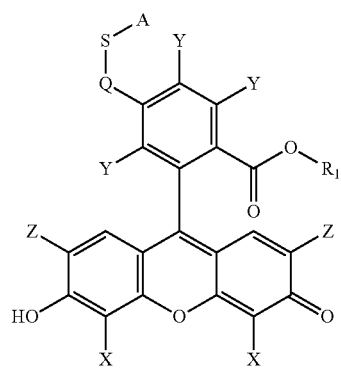

wherein

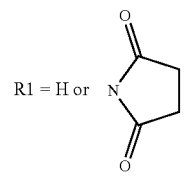

R1 = H or

X = Z = Br, Y = H    Eosin Y
X = Br = NO2, Y = H    Eosin B
X = Z = I, Y = H    Erthrosine B
X = Z = Br, Y = Cl    Phloxine B and wherein Q is O or NH, S is a spacer or a bond, and A is an anchorable moiety capable of being polymerized into a hydrogel matrix.

10. The eosin derivative of claim 9 wherein S is selected from

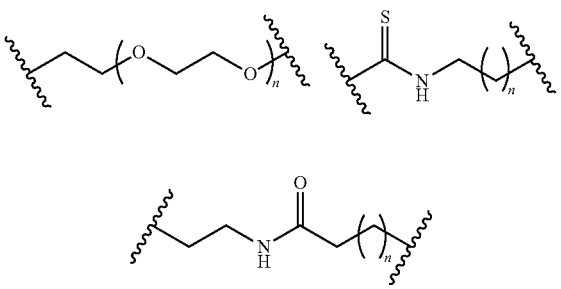

wherein n is an integer from 1 to 10.

11. The cosin derivative of claim 9 wherein A is selected from a methacrylate, an acrylate, an acrylamide, a monoalkylacrylamide, a vinylalcohol, a vinylamine, an allylamine or an allylalcohol moiety.

12. The cosin derivative of claim 9 wherein A is selected from:

wherein R is H, alkyl, acyl, or nitrile.

13. The eosin derivative of claim 12 wherein the alkyl is a $C_{1-6}$alkyl group.

14. The eosin derivative of claim 12 wherein the acyl is selected from methanoyl, ethanoyl, propanoyl, isopropanoyl, butanoyl, isobutanoyl, t-butanoyl, pentanoyl, isopentanoyl, neopentanoyl or benzoyl.

15. The eosin derivative of claim 9 wherein the compound has formula:

IIIA

IIIB

IIIC

IVA

-continued

IVB

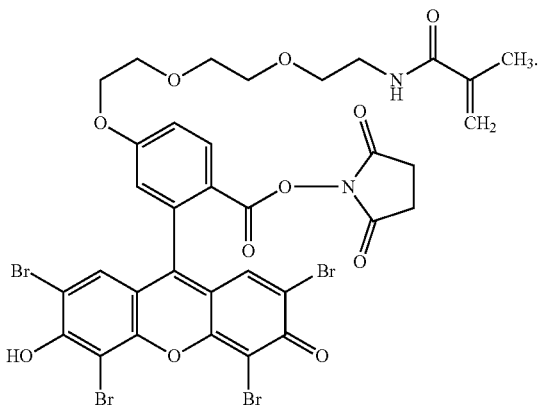

16. A method for high resolution detection of biomolecules in a biological sample comprising the steps of:
   a. labeling biomolecules in the sample with the anchorable hematoxylin derivative of claim 1, the anchorable hematoxylin derivative of claim, or the anchorable eosin derivative of claim 9, or the combination thereof, wherein the anchorable moiety in said anchorable hematoxylin, anchorable eosin, or combination thereof is capable of crosslinking to a swellable material;
   b. permeating the sample with a polymerizable material and polymerizing the material, wherein the polymerizing results in covalent crosslinking of the anchor to the swellable material to form a sample-swellable material complex;
   c. digesting the sample-swellable material complex;
   d. enlarging the sample-swellable material complex by adding an aqueous solvent or liquid to cause the sample to swell, thereby physically expanding the sample-swellable material complex resulting in an enlarged biological sample; and
   e. detecting the biomolecules in the sample under high resolution using conventional diffraction limited light microscopy.

17. The method of claim 16 comprising labeling with an anchorable hematoxylin and an anchorable eosin.

18. The method of claim 16, wherein the sample is exposed to a protein cross-linker, a nucleic acid cross-linker, or the combination thereof, before, during, or after labeling with the anchorable hematoxylin, anchorable eosin, or combination thereof.

19. The method of claim 18 wherein the protein cross-linker is glutaraldehyde or AcX, and the nucleic acid cross-linker is NucliX.

20. A microscopy method for producing a high-resolution or nano-scale resolution image of a sample of interest, the method comprising enlarging the sample of interest in accordance with claim 16, and viewing the enlarged sample under a light microscope.

21. An enlargeable sample of interest produced by the method of claim 16.

* * * * *